(12) United States Patent
Myer et al.

(10) Patent No.: US 11,350,854 B2
(45) Date of Patent: Jun. 7, 2022

(54) AUGMENTED NEUROMUSCULAR TRAINING SYSTEM AND METHOD

(71) Applicants: Children's Hospital Medical Center, Cincinnati, OH (US); University of Cincinnati, Cincinnati, OH (US)

(72) Inventors: Gregory Donald Myer, Cincinnati, OH (US); Michael Alan Riley, Cincinnati, OH (US); Adam Charles Kiefer, Cincinnati, OH (US)

(73) Assignees: Children's Hospital Medical Center, Cincinnati, OH (US); University of Cincinnati, Cincinnati, OH (US)

( * ) Notice: Subject to any disclaimer, the term of this patent is extended or adjusted under 35 U.S.C. 154(b) by 1173 days.

(21) Appl. No.: 15/811,513

(22) Filed: Nov. 13, 2017

(65) Prior Publication Data

US 2018/0125395 A1    May 10, 2018

Related U.S. Application Data

(60) Provisional application No. 62/420,119, filed on Nov. 10, 2016.

(51) Int. Cl.
*A61B 5/11* (2006.01)
*A61B 5/00* (2006.01)
*A61B 5/107* (2006.01)

(52) U.S. Cl.
CPC .......... *A61B 5/1121* (2013.01); *A61B 5/1107* (2013.01); *A61B 5/1118* (2013.01); *A61B 5/1122* (2013.01); *A61B 5/1127* (2013.01); *A61B 5/4533* (2013.01); *A61B 5/4585* (2013.01); *A61B 5/486* (2013.01); *A61B 5/6803* (2013.01); *A61B 5/742* (2013.01);
(Continued)

(58) Field of Classification Search
CPC ... A61B 5/1121; A61B 5/1107; A61B 5/1118; A61B 5/1122; A61B 5/112; A61B 5/4533; A61B 5/4585; A61B 5/486; A61B 5/6803; A61B 5/742; A61B 5/1071; A61B 5/1114; A61B 5/1116; A61B 5/1124; A61B 5/1128; A61B 5/4538; A61B 5/6814; A61B 5/744; A61B 5/7445; A61B 5/0002; A61B 2505/09; G16H 20/30; G09B 19/00; G09B 19/0038; A63B 71/0622; A63B 2220/803; A63B 24/00; A63B 2071/0647
See application file for complete search history.

(56) References Cited

U.S. PATENT DOCUMENTS 5,919,149 A * 7/1999 Allum .................. A61B 5/1116
                                                          600/595
7,643,158 B2   1/2010 Alexander
(Continued)

OTHER PUBLICATIONS

On the Modification of Risk Factors for Anterior Cruicate Ligament Injuries in Female Athletes Through Visual Feedback, Scott H. Bonnette, Oct. 2016, University of Cincinnati, pp. 1-58 (Year: 2016).*

(Continued)

*Primary Examiner* — Patrick Fernandes
(74) *Attorney, Agent, or Firm* — Bose McKinney & Evans LLP

(57) ABSTRACT

An augmented neuromuscular training system and method for providing feedback to a user in order to reduce movement deficits associated with injury risk, prior injury or disease pathology.

24 Claims, 29 Drawing Sheets

(52) U.S. Cl.
CPC ........... *A61B 5/1071* (2013.01); *A61B 5/1114* (2013.01); *A61B 5/1116* (2013.01); *A61B 5/1124* (2013.01); *A61B 5/1128* (2013.01); *A61B 5/4538* (2013.01); *A61B 5/6814* (2013.01); *A61B 5/744* (2013.01); *A61B 5/7445* (2013.01)

(56) References Cited

U.S. PATENT DOCUMENTS

| | | | |
|---|---|---|---|
| 8,223,208 | B2 | 7/2012 | Alexander |
| 8,427,325 | B2 | 4/2013 | Ferguson et al. |
| 8,848,035 | B2 | 9/2014 | Alexander |
| 9,161,708 | B2 | 10/2015 | Elliott et al. |
| 9,589,207 | B2 | 3/2017 | Holohan |
| 9,741,136 | B2 | 8/2017 | Holz |
| 9,741,169 | B1 | 8/2017 | Holz |
| 9,761,011 | B2 | 9/2017 | Utsunomiya et al. |
| 2007/0143177 | A1* | 6/2007 | Graves ............... G06Q 30/0207 705/14.15 |
| 2009/0043170 | A1* | 2/2009 | Sulkin .................. A61B 5/1126 600/300 |
| 2010/0022351 | A1* | 1/2010 | Lanfermann ...... A63B 24/0006 482/1 |
| 2011/0208444 | A1* | 8/2011 | Solinsky .............. A61B 5/1122 702/41 |
| 2011/0270135 | A1* | 11/2011 | Dooley ................. A61B 5/1114 600/595 |
| 2012/0116258 | A1* | 5/2012 | Lee ...................... A61B 5/1071 600/595 |
| 2014/0228985 | A1* | 8/2014 | Elliott ................. G06F 19/3481 700/91 |
| 2015/0004581 | A1* | 1/2015 | Selman .............. G09B 19/0038 434/257 |
| 2018/0020954 | A1* | 1/2018 | Lillie ..................... G16H 50/50 600/476 |

OTHER PUBLICATIONS

Christine D. Pollard, Limited Hip and Knee Flexion During Landing is Associated with Increased Frontal Plane Knee Motion and Moments, 2010, Clin Biomech, 24(2), pp. 1-12 (Year: 2010).*
Timothy E. Hewett, The Mechanistic Connection Between the Trunk, Knee, and Anterior Cruciate Ligament Injury, 2011, Exerc Sport Sci Rev, 39(4), pp. 161-166 (Year: 2011).*
Agel, J., Arendt, E. A., & Bershadsky, B. (2005). Anterior cruciate ligament injury in national collegiate athletic association basketball and soccer: A 13-year review. *The American Journal of Sports Medicine*, 33(4), 524-531.
Besier, T. F., Lloyd, D. G., & Ackland, T. R. (2003). Muscle activation strategies at the knee during running and cutting maneuvers. Medicine and Science in Sports and Exercise, 35(1), 119-127.
Boden, B. P., Dean, G. S., Feagin Jr, J. A., & Garrett Jr, W. E. (2000). Mechanisms of anterior cruciate ligament injury. Orthopedics, 23(6), 573-578.
Boden, B. P., Torg, J. S., Knowles, S. B., & Hewett, T. E. (2009). Video analysis of anterior cruciate ligament injury abnormalities in hip and ankle kinematics. The American Journal of Sports Medicine, 37(2), 252-259.
Carson, D. W., & Ford, K. R. (2011). Sex differences in knee abduction during landing: A systematic review. Sports Health: A Multidisciplinary Approach, 3(4), 373-382.
Center for Disease Control and Prevention. (2010). A national public health agenda for osteoarthritis. Retrieved from http://www.cdc.gov/arthritis/docs/oaagenda.pdf.
Chandy, T. A., & Grana, W. A. (1985). Secondary school athletic injury in boys and girls: A three-year comparison. The Physician and Sportsmedicine, 13, 106-111.
Csintalan, R. P., Inacio, M. C., & Funahashi, T. T. (2008). Incidence rate of anterior cruciate ligament reconstructions. The Permanente Journal, 12(3), 17-21.

De Marche Baldon, R., Lobato, D. F. M., Carvalho, L. P., Wun, P. Y. L., Presotti, C. V., & Serrão, F. V. (2012). Relationships between eccentric hip isokinetic torque and functional performance. Journal of Sport Rehabilitation, 21, 26-33.
Dufek, J. S., & Bates, B. T. (1991). Biomechanical factors associated with injury during landing in jump sports. Sports Medicine, 12(5), 326-337.
Emerson, R. J. (1993). Basketball knee injuries and the anterior cruciate ligament. Clinics in Sports Medicine, 12, 317-328.
Ferretti, A., Papandrea, P., Conteduca, F., & Mariani, P. P. (1992). Knee ligament injuries in volleyball players. The American Journal of Sports Medicine, 20(2), 203-207.
Ford, K. R., Myer, G. D., & Hewett, T. E. (2010). Longitudinal effects of maturation on lower extremity joint stiffness in adolescent athletes. The American Journal of Sports Medicine, 38(9), 1829-1837.
Ford, K. R., Myer, G. D., Smith, R. L., Vianello, R. M., Seiwert, S. L., & Hewett, T. E. (2006). A comparison of dynamic coronal plane excursion between matched male and female athletes when performing single leg landings. Clinical Biomechanics, 21(1), 33-40.
Ford, K. R., Myer, G. D., Toms, H. E., & Hewett, T. E. (2005). Gender differences in the kinematics of unanticipated cutting in young athletes. Medicine and Science in Sports and Exercise, 37(1), 124-129.
Freudenheim, A. M., Wulf, G., Madureira, F., Pasetto, S. C., & Corrêa, U. C. (2010). An external focus of attention results in greater swimming speed. International Journal of Sports Science and Coaching, 5(4), 533-542.
Friedman, A., & Kohler, B. (2003). Bidimensional regression: Assessing the configural similarity and accuracy of cognitive maps and other two-dimensional data sets. Psychological Methods, 8(4), 468-491.
Gagnier, J. J., Morgenstern, H., & Chess, L. (2013). Interventions designed to prevent anterior cruciate ligament injuries in adolescents and adults: A Systematic review and meta-analysis. The American Journal of Sports Medicine, 41(8), 1952-1962.
Gerberich, S., Luhmann, S., Finke, C., Priest, J., & Beard, B. (1987). Analysis of severe injuries associated with volleyball activities. The Physician and Sportsmedicine, 15(8), 75-79.
Gibson, J. J. (1966). The senses considered as perceptual systems. Oxford, UK: Houghton-Mifflin.
Gibson, J. J. (1986). The ecological approach to visual perception. Boston, MA: Houghton-Mifflin.
Giza, E., Mithöfer, K., Farrell, L., Zarins, B., & Gill, T. (2005). Injuries in women's professional soccer. British Journal of Sports Medicine, 39(4), 212-216.
Gray, J., Taunton, J. E., McKenzie, D. C., Clement, D. B., McConkey, J. P., & Davidson, R. G. (1985). A survey of injuries to the anterior cruciate ligament of the knee in female basketball players. International Journal of Sports Medicine, 6(6), 314-316.
Hawkins, R. D., Hulse, M. A., Wilkinson, C., Hodson, A., & Gibson, M. (2001). The association football medical research programme: An audit of injuries in professional football. British Journal of Sports Medicine, 35(1), 43-47.
Heidt, R. S., Sweeterman, L. M., Carlonas, R. L., Traub, J. A., & Tekulve, F. X. (2000). Avoidance of soccer injuries with preseason conditioning. The American Journal of Sports Medicine, 28(5), 659-662.
Herman, D. C., Weinhold, P. S., Guskiewicz, K. M., Garrett, W. E., Yu, B., & Padua, D. A. (2008). The effects of strength training on the lower extremity biomechanics of female recreational athletes during a stop-jump task. The American Journal of Sports Medicine, 36(4), 733-740.
Hewett, T. E., Ford, K. R., & Myer, G. D. (2006). Anterior cruciate ligament injuries in female athletes: Part 2, a meta-analysis of neuromuscular interventions aimed at injury prevention. The American Journal of Sports Medicine, 34(3), 490-498.
Hewett, T. E., Lindenfeld, T. N., Riccobene, J. V., & Noyes, F. R. (1999). The effect of neuromuscular training on the incidence of knee injury in female athletes: A prospective study. The American Journal of Sports Medicine, 27(6), 699-706.

(56) References Cited

OTHER PUBLICATIONS

Hewett, T. E., & Myer, G. D. (2011). The mechanistic connection between the trunk, knee, and anterior cruciate ligament injury. Exercise and Sport Sciences Reviews, 39(4), 161-166.

Hewett, T. E., Myer, G. D., & Ford, K. R. (2004). Decrease in neuromuscular control about the knee with maturation in female athletes. The Journal of Bone and Joint Surgery, 86(8), 1601-1608.

Hewett, T. E., Myer, G. D., & Ford, K. R. (2006). Anterior cruciate ligament injuries in female athletes: Part 1, mechanisms and risk factors. The American Journal of Sports Medicine, 34(2), 299-311.

Hewett, T. E., Myer, G. D., Ford, K. R., Heidt, R. S., Colosimo, A. J., McLean, S. G., . . . Succop, P. (2005). Biomechanical measures of neuromuscular control and valgus loading of the knee predict anterior cruciate ligament injury risk in female athletes: A prospective study. The American Journal of Sports Medicine, 33(4), 492-501.

Hewett T. E., Torg J. S., Boden B. P. Video analysis of trunk and knee motion during non-contact anterior cruciate ligament injury in female athletes: lateral trunk and knee abduction motion are combined components of the injury mechanism. Br J Sports Med. 2009;43(6):417-22. Epub Apr. 18, 2009. doi: 10.1136/bjsm.2009.059162. PubMed PMID: 19372088; PubMed Central PMCID: PMCJournal—In Process.

Kiefer, A. W., Kushner, A. M., Groene, J., Williams, C., Riley, M. A., & Myer, G. D. (2015). A commentary on real-time biofeedback to augment neuromuscular training for ACL injury prevention in adolescent athletes. Journal of Sports Science and Medicine, 14, 1-8.

Kim, S., Bosque, J., Meehan, J. P., Jamali, A., & Marder, R. (2011). Increase in outpatient knee arthroscopy in the United States: A comparison of National Surveys of Ambulatory Surgery, 1996 and 2006. The Journal of Bone and Joint Surgery. American vol. 93(11), 994-1000.

Klugman, M. F., Brent, J. L., Myer, G. D., Ford, K. R., & Hewett, T. E. (2011). Does an in-season only neuromuscular training protocol reduce deficits quantified by the tuck jump assessment? Clinics in Sports Medicine, 30(4), 825-840.

Koga, H., Nakamae, A., Shima, Y., Iwasa, J., Myklebust, G., Engebretsen, L., Krosshaug, T. (2010). Mechanisms for noncontact anterior cruciate ligament injuries knee joint kinematics in 10 injury situations from female team handball and basketball. The American Journal of Sports Medicine, 38(11), 2218-2225.

Krosshaug, T., Nakamae, A., Boden, B. P., Engebretsen, L., Smith, G., Slauterbeck, J. R., Bahr, R. (2007). Mechanisms of anterior cruciate ligament injury in basketball video analysis of 39 cases. The American Journal of Sports Medicine, 35(3), 359-367.

LaBella, C. R., Huxford, M. R., Grissom, J., Kim, K.-Y., Peng, J., & Christoffel, K. K. (2011). Effect of neuromuscular warm-up on injuries in female soccer and basketball athletes in urban public high schools: cluster randomized controlled trial. Archives of Pediatrics & Adolescent Medicine, 165(11), 1033-1040.

Lloyd, D. G., & Buchanan, T. S. (2001). Strategies of muscular support of varus and valgus isometric loads at the human knee. Journal of Biomechanics, 34(10), 1257-1267.

Lohmander, L. S., Englund, P. M., Dahl, L. L., & Roos, E. M. (2007). The long-term consequence of anterior cruciate ligament and meniscus injuries osteoarthritis. The American Journal of Sports Medicine, 35(10), 1756-1769.

Malone, T. R., Hardaker, W. T., Garrett, W. E., Feagin, J. A., & Bassett, F. H. (1993). Relationship of gender to anterior cruciate ligament injuries in intercollegiate basketball players. Journal of the Southern Orthopedic Association, 2(1), 36-39.

Mandelbaum, B. R., Silvers, H. J., Watanabe, D. S., Knarr, J. F., Thomas, S. D., Griffin, L. Y., . . . Garrett, W. (2005). Effectiveness of a neuromuscular and proprioceptive training program in preventing anterior cruciate ligament injuries in female athletes: 2-year follow-up. The American Journal of Sports Medicine, 33(7), 1003-1010.

Marr, D. (1982). Vision: A computational investigation into the human representation and processing of visual information. San Francisco, CA: W. H. Freeman and Company.

Kim S., Bosque J., Meehan J. P., Jamali A., Marder R. Increase in outpatient knee arthroscopy in the United States: a comparison of National Surveys of Ambulatory Surgery, 1996 and 2006. The Journal of Bone & Joint Surgery. 2011;93(11):994-1000; PubMed Central PMCID: PMCJournal—In Process.

McNair, P. J., Marshall, R. N., & Matheson, J. A. (1990). Important features associated with acute anterior cruciate ligament injury. The New Zealand Medical Journal, 103(901), 537-539.

Mechsner, F., Kerzel, D., Knoblich, G., & Prinz, W. (2001). Perceptual basis of bimanual coordination , F., Kerzel, D., Knoblich, G & Prinz, W. Nature, 414(6859), 69-73.

Murphy, L., Schwartz, T. A., Helmick, C. G., Renner, J. B., Tudor, G., Koch, G., Jordan, J. M. (2008). Lifetime risk of symptomatic knee osteoarthritis. Arthritis Care and Research, 59(9), 1207-1213.

Myer, G. D., Ford, K. R., Brent, J. L., & Hewett, T. E. (2007). Differential neuromuscular training effects on ACL injury risk factors in "high-risk" versus "low-risk" athletes. BMC Musculoskeletal Disorders, 8(39). http://doi.org/10.1186/1471-2474-8-39.

Myer, G. D., Ford, K. R., Palumbo, J. P., & Hewett, T. E. (2005). Neuromuscular training improves performance and lower-extremity biomechanics in female athletes. The Journal of Strength and Conditioning Research, 19(1), 51-60.

Myer, G. D., Stroube, B. W., DiCesare, C. A., Brent, J. L., Ford, K. R., Heidt, R. S., & Hewett, T. E. (2013). Augmented feedback supports skill transfer and reduces high-risk injury landing mechanics a double-blind, randomized controlled laboratory study. The American Journal of Sports Medicine, 41(3), 669-677.

Myer, G. D., Sugimoto, D., Thomas, S., & Hewett, T. E. (2012). The Influence of Age on the Effectiveness of Neuromuscular Training to Reduce Anterior Cruciate Ligament Injury in Female Athletes: A Meta-Analysis. The American Journal of Sports Medicine, 41(1), 203-215, 363546512460637.

Myklebust, G., Engebretsen, L., Brækken, I. H., Skjølberg, A., Olsen, O.-E., & Bahr, R. (2003). Prevention of anterior cruciate ligament injuries in female team handball players: A prospective intervention study over three seasons. Clinical Journal of Sport Medicine, 13(2), 71-78.

Neisser, U. (1967). Cognitive psychology. New York: Appleton-Century-Crofts.

Nielsen, J. M., & Hammar, M. (1991). Sports injuries and oral contraceptive use. Sports Medicine, 12(3), 152-160.

Olsen O. E., Myklebust G., Engebretsen L., Bahr R. Injury mechanisms for anterior cruciate ligament injuries in team handball: a systematic video analysis. Am J Sports Med. 2004;32(4):1002-12. PubMed PMID: 15150050.

Pappas, E., Nightingale, E. J., Simic, M., Ford, K. R., Hewett, T. E., & Myer, G. D. (2015). Do exercises used in injury prevention programmes modify cutting task biomechanics? A systematic review with meta-analysis. British Journal of Sports Medicine, 49(10), 673-680.

Pfeiffer, R. P., Shea, K. G., Roberts, D., Grandstrand, S., & Bond, L. (2006). Lack of effect of a knee ligament injury prevention program on the incidence of noncontact anterior cruciate ligament injury. The Journal of Bone & Joint Surgery, 88(8), 1769-1774.

Porter, J. M., Anton, P. M., & Wu, W. F. (2012). Increasing the distance of an external focus of attention enhances standing long jump performance. The Journal of Strength and Conditioning Research, 26(9), 2389-2393.

Porter, J. M., Ostrowski, E. J., Nolan, R. P., & Wu, W. F. (2010). Standing long-jump performance is enhanced when using an external focus of attention. The Journal of Strength and Conditioning Research, 24(7), 1746-1750.

Porter, J. M., Wu, W. F., Crossley, R. M., Knopp, S. W., & Campbell, O. C. (2015). Adopting an external focus of attention improves sprinting performance in low-skilled sprinters. The Journal of Strength and Conditioning Research, 29(4), 947-953.

Powers, W. T. (1973). Behavior: The control of perception. Chicago: Aldine.

(56) References Cited

OTHER PUBLICATIONS

Pylyshyn, Z. W. (1989). The role of location indexes in spatial perception: A sketch of the FINST spatial-index model. Cognition, 32, 65-97.
Ramenzoni, V. C., Riley, M. A., Shockley, K., & Baker, A. A. (2012). Interpersonal and intrapersonal coordinative modes for joint and single task performance. Human Movement Science, 31(5), 1253-1267.
Senn, S. (2002). Cross-over trials in clinical research. Hoboken, NJ: John Wiley and Sons.
Söderman, K., Alfredson, H., Pietilä, T., & Werner, S. (2001). Risk factors for leg injuries in female soccer players: A prospective investigation during one out-door season. Knee Surgery, Sports Traumatology, Arthroscopy, 9(5), 313-321.
Soderman K., Werner S., Pietila T., Engstrom B., Alfredson H., Balance board training: Prevention of traumatic injuries of the lower extremities in female soccer players? A prospective randomized intervention study. Knee Surg. Sports Traumatol Arthrosc. 2000; 8(6): 356-363. PubMed PMID: 11147154.
Solomonow, M., Baratta, R., Zhou, B. H., Shoji, H., Bose, W., Beck, C., & D'ambrosia, R. (1987). The synergistic action of the anterior cruciate ligament and thigh muscles in maintaining joint stability. The American Journal of Sports Medicine, 15(3), 207-213.
Steffen, K., Myklebust, G., Olsen, O. E., Holme, I., & Bahr, R. (2008). Preventing injuries in female youth football—a cluster-randomized controlled trial. Scandinavian Journal of Medicine & Science in Sports, 18(5), 605-614.
Stroube, B. W., Myer, G. D., Brent, J. L., Ford, K. R., Heidt Jr, R. S., & Hewett, T. E. (2013). Effects of task-specific augmented feedback on deficit modification during performance of the tuck-jump exercise. Journal of Sport Rehabilitation, 22(1), 7-18.
Sugimoto, D., Myer, G. D., Barber Foss, K. D., & Hewett, T. E. (2014). Dosage effects of neuromuscular training intervention to reduce anterior cruciate ligament injuries in female athletes: Meta- and sub-group analyses. Sports Medicine, 44(4), 551-562.
Sugimoto, D., Myer, G. D., Bush, H. M., Klugman, M. F., McKeon, J. M. M., & Hewett, T. E. (2012). Compliance with neuromuscular training and anterior cruciate ligament injury risk reduction in female athletes: A meta-analysis. Journal of Athletic Training, 47(6), 714-723.
Sugimoto, D., Myer, G. D., McKeon, J. M., & Hewett, T. E. (2012). Evaluation of the effectiveness of neuromuscular training to reduce anterior cruciate ligament injury in female athletes: A critical review of relative risk reduction and numbers needed-to-treat analyses. British Journal of Sports Medicine, 46, 979-988.
Swinnen, S. P., Lee, T. D., Verschueren, S., Serrien, D. J., & Bogaerds, H. (1997). Interlimb coordination: Learning and transfer under different feedback conditions. Human Movement Science, 16(6), 749-785.
Tibone, J. E., Antich, T. J., Fanton, G. S., Moynes, D. R., Perry, J., & others. (1986). Functional analysis of anterior cruciate ligament instability. The American Journal of Sports Medicine, 14(4), 276-284.
Varoqui, D., Froger, J., Pélissier, J. Y., & Bardy, B. G. (2011). Effect of coordination biofeedback on (re) learning preferred postural patterns in post-stroke patients. Motor Control, 15(2), 187-205.
Whiteside, P. A. (1980). Men's and women's injuries in comparable sports. The Physician and Sportsmedicine, 8(3), 130-140.
Winter, D. A. (2009). Biomechanics and motor control of human movement. Hoboken, NJ: John Wiley and Sons.
Wulf, G. (2013). Attentional focus and motor learning: A review of 15 years. International Review of Sport and Exercise Psychology, 6(1), 77-104.
Wulf, G., & Dufek, J. S. (2009). Increased jump height with an external focus due to enhanced lower extremity joint kinetics. Journal of Motor Behavior, 41(5), 401-409.
Wulf, G., Dufek, J. S., Lozano, L., & Pettigrew, C. (2010). Increased jump height and reduced EMG activity with an external focus. Human Movement Science, 29(3), 440-448.
Wulf, G., Höß, M., & Prinz, W. (1998). Instructions for motor learning: Differential effects of internal versus external focus of attention. Journal of Motor Behavior, 30(2), 169-179.
Wulf, G., Zachary, T., Granados, C., & Dufek, J. (2007). Increases in jump-and-reach height through an external focus of attention. International Journal of Sports Science and Coaching, 2(3), 275-284.
Zazulak, B. T., Hewett, T. E., Reeves, N. P., Goldberg, B., & Cholewicki, J. (2007a). Deficits in neuromuscular control of the trunk predict knee injury risk: A prospective biomechanical-epidemiologic study. The American Journal of Sports Medicine, 35(7), 1123-1130.
Zazulak, B. T., Hewett, T. E., Reeves, N. P., Goldberg, B., & Cholewicki, J. (2007b). The effects of core proprioception on knee injury a prospective biomechanical-epidemiological study. The American Journal of Sports Medicine, 35(3), 368-373.
Zelisko, J. A., Noble, H. B., & Porter, M. (1982). A comparison of men's and women's professional basketball injuries. The American Journal of Sports Medicine, 10(5), 297-299.
Joseph A. M., Collins C. L., Henke N. M., Yard E. E., Fields S. K., Comstock R. D. A multisport epidemiologic comparison of anterior cruciate ligament injuries in high school athletics. J Athl Train. 2012; 48(6): 810-7.
Myklebust G., Bahr R. Return to play guidelines after anterior cruciate ligament surgery. Br J Sports Med. 2005; 39(3):127-31. PubMed PMID: 15728687; PubMed Central PMCID: PMC1725142.
Barenius B., Ponzer S., Shalabi A., Bujak R., Norlén L., Eriksson K. Increased Risk of Osteoarthritis After Anterior Cruciate Ligament Reconstruction A 14-Year Follow-up Study of a Randomized Controlled Trial. The American journal of sports medicine. 2014;42(5):1049-57; PubMed Central PMCID: PMCJournal—In Process.
Von Porat A., Roos E. M., Roos H. High prevalence of osteoarthritis 14 years after an anterior cruciate ligament tear in male soccer players: a study of radiographic and patient relevant outcomes. Ann Rheum Dis. 2004;63(3):269-73. PubMed PMID: 14962961.
Lohmander L. S., Ostenberg A., Englund M., Roos H. High prevalence of knee osteoarthritis, pain, and functional limitations in female soccer players twelve years after anterior cruciate ligament injury. Arthritis Rheum. 2004;50(10):3145-52. PubMed PMID: 15476248.
Arthritis Foundation. A National Public Health Agenda for Osteoarthritis 2010, Mar. 11, 2013. Available from: http://www.cdc.gov/arthritis/docs/OAagenda.pdf.
Hootman J. M., Dick R., Agel J. Epidemiology of collegiate injuries for 15 sports: summary and recommendations for injury prevention initiatives. J Athl Train. 2007;42(2):311-9. PubMed PMID: 17710181; PubMed Central PMCID: PMC1941297.
Myer G. D., Ford K. R., McLean S. G., Hewett T.E. The effects of plyometric versus dynamic stabilization and balance training on lower extremity biomechanics. Am J Sports Med. 2006;34(3):445-55. doi: 10.1177/0363546505281241. PubMed PMID: 16282579.
Ford K. R., DiCesare C. A., Myer G. D., Hewett T.E. Real-Time Biofeedback to Target Risk of Anterior Cruciate Ligament Injury: A Technical Report for Injury Prevention and Rehabilitation. J Sport Rehabil. 2015;In Press. doi: 10.1123/jsr.2013-0138. PubMed PMID: 24959871.
Wulf G., McNevin N., Shea C. H. The automaticity of complex motor skill learning as a function of attentional focus. The Quarterly Journal of Experimental Psychology: Section A. 2001;54(4):1143-54.
Wulf G., Mcconnel N., Gärtner M., Schwarz A. Enhancing the learning of sport skills through external-focus feedback. J Mot Behav. 2002;34(2):171-82.
Benjaminse A., Otten E. ACL injury prevention, more effective with a different way of motor learning? Knee Surg Sports Traumatol Arthrosc. 2011;19(4):622-7. Epub Nov. 17, 2010. doi: 10.1007/s00167-010-1313-z. PubMed PMID: 21079917; PubMed Central PMCID: PMC3062033.
Benjaminse A., Gokeler A., Dowling A. V., Faigenbaum A., Ford K. R., Hewett T. E., Onate J. A., Otten B., Myer G. D. Optimization of the Anterior Cruciate Ligament Injury Prevention Paradigm: Novel Feedback Techniques to Enhance Motor Learning and Reduce

(56) References Cited

OTHER PUBLICATIONS

Injury Risk. J Orthop Sports Phys Ther. 2015:1-46. Epub Jan. 30, 2015. doi: 10.2519/jospt.2015.4986. PubMed PMID: 25627151.

Alentorn-Geli E., Mendiguchia J., Samuelsson K., Musahl V., Karlsson J., Cugat R, Myer G. D. Prevention of anterior cruciate ligament injuries in sports. Part I: systematic review of risk factors in male athletes. Knee Surg Sports Traumatol Arthrosc. 2014;22(1):3-15. Epub Jan. 5, 2014. doi: 10.1007/s00167-013-2725-3. PubMed PMID: 24385003; PubMed Central PMCID: PMCJournal—In Process.

Alentorn-Geli E., Mendiguchia J., Samuelsson K., Musahl V., Karlsson J., Cugat R., Myer G. D. Prevention of non-contact anterior cruciate ligament injuries in sports. Part II: systematic review of the effectiveness of prevention programmes in male athletes. Knee Surg Sports Traumatol Arthrosc. 2014;22(1):16-25. Epub Oct. 29, 2013. doi: 10.1007/s00167-013-2739-x. PubMed PMID: 24162718; PubMed Central PMCID: PMCJournal—In Process.

Grooms D. R., Palmer T., Onate J. A., Myer G. D., Grindstaff T.. Soccer-specific warm-up and lower extremity injury rates in collegiate male soccer players. J Athl Train. 2013;48(6):782-9. Epub Jul. 16, 2013. doi: 10.4085/1062-6050-48.4.08. PubMed PMID: 23848519; PubMed Central PMCID: PMC3867089.

Faigenbaum A. D., Farrell A., Fabiano M., Radler T., Naclerio F., Ratamess N. A., Kang J., Myer G. D. Effects of integrative neuromuscular training on fitness performance in children. Pediatr Exerc Sci. 2011;23(4):573-84. Epub Nov. 24, 2011. PubMed PMID: 22109781; PubMed Central PMCID: PMCJournal—In Process.

Faigenbaum A. D., Myer G. D., Farrell A., Radler T., Fabiano M., Kang J., Ratamess N., Khoury J., Hewett T. E. Integrative neuromuscular training and sex-specific fitness performance in 7-year-old children: an exploratory investigation. J Athl Train. 2014;49(2):145-53. Epub Feb. 5, 2014. doi: 10.4085/1062-6050-49.1.08. PubMed PMID: 24490841; PubMed Central PMCID: PMC3975769.

Myer G. D., Faigenbaum A. D., Chu D. A., Falkel J., Ford K. R., Best T. M., Hewett T. E. Integrative training for children and adolescents: techniques and practices for reducing sports-related injuries and enhancing athletic performance. Phys Sportsmed. 2011;39(1):74-84. Epub Mar. 8, 2011. doi: 10.3810/psm.2011.02.1864. PubMed PMID: 21378489; PubMed Central PMCID: PMCJournal—In Process.

Di Stasi S., Myer G. D., Hewett T. E. Neuromuscular training to target deficits associated with second anterior cruciate ligament injury. J Orthop Sports Phys Ther. 2013;43(11):777-92, A1-11. Epub Nov. 2, 2013. doi: 10.2519/jospt.2013.4693. PubMed PMID: 24175599; PubMed Central PMCID: PMC4163697.

Hewett T. E., Di Stasi S. L., Myer G. D. Current concepts for injury prevention in athletes after anterior cruciate ligament reconstruction. Am J Sports Med. 2013;41(1):216-24. Epub Oct. 9, 2012. doi: 10.1177/0363546512459638. PubMed PMID: 23041233; PubMed Central PMCID: PMC3592333.

Myer G. D., Paterno M. V., Ford K. R., Hewett T. E. Neuromuscular Training Techniques to Target Deficits Before Return to Sport After Anterior Cruciate Ligament Reconstruction. J Strength Cond Res. 2008;22(3):987-1014. doi: 10.1519/JSC.0b013e31816a86cd. PubMed PMID: 18438211.

Myer G. D., Schmitt L. C., Brent J. L., Ford K. R., Barber Foss K. D., Scherer B. J., Heidt R. S., Jr., Divine J. G., Hewett T. E. Utilization of modified NFL combine testing to identify functional deficits in athletes following ACL reconstruction. J Orthop Sports Phys Ther. 2011;41(6):377-87. Epub Feb. 4, 2011. doi: 10.2519/jospt.2011.3547. PubMed PMID: 21289456; PubMed Central PMCID: PMC3439811.

Myer G. D., Martin L., Jr., Ford K. R., Paterno M. V., Schmitt L. C., Heidt R. S., Jr., Colosimo A., Hewett T. E. No association of time from surgery with functional deficits in athletes after anterior cruciate ligament reconstuction: evidence for objective return-to-sport criteria. Am J Sports Med. 2012;40(10):2256-63. Epub Aug. 11, 2012. doi: 10.1177/0363546512454656. PubMed PMID: 22879403; PubMed Central PMCID: PMC4168970.

Gokeler A., Benjaminse A., Hewett T. E., Paterno M. V., Ford K. R., Otten E., Myer G. D. Feedback techniques to target functional deficits following anterior cruciate ligament reconstruction: implications for motor control and reduction of second injury risk. Sports Med. 2013;43(11):1065-74. Epub Sep. 26, 2013. doi: 10.1007/s40279-013-0095-0. PubMed PMID: 24062274; PubMed Central PMCID: PMC4166506.

Gokeler A., Bisschop M., Myer G. D., Benjaminse A., Dijkstra P. U., vanKeeken H. G., vanRaay J. J., Burgerhof J. G., Otten E. Immersive virtual reality improves movement patterns in patients after ACL reconstruction: implications for enhanced criteria-based return-to-sport rehabilitation. Knee Surg Sports Traumatol Arthrosc. 2015. Epub Oct. 15, 2014. doi: 10.1007/s00167-014-3374-x. PubMed PMID: 25311052.

Knowles S. B., Marshall S. W., Miller T., Spicer R., Bowling J., Loomis D., Millikan R., Yang J., Mueller F. Cost of injuries from a prospective cohort study of North Carolina high school athletes. Inj Prev. 2007;13(6):416-21.

Myer G. D., Ford K. R., Hewett T. E.. Rationale and Clinical Techniques for Anterior Cruciate Ligament Injury Prevention Among Female Athletes. J Athl Train. 2004;39(4):352-64. PubMed PMID: 15592608.

Toth A. P., Cordasco F. A. Anterior cruciate ligament injuries in the female athlete. J Gend Specif Med. 2001;4(4):25-34. PubMed PMID: 11727468.

Paterno M. V., Schmitt L. C., Ford K. R., Rauh M. J., Myer G. D., Huang B., Hewett T. E. Biomechanical measures during landing and postural stability predict second anterior cruciate ligament injury after anterior cruciate ligament reconstruction and return to sport. Am J Sports Med. 2010;38(10):1968-78. Epub Aug. 13, 2010. doi: 10.1177/0363546510376053. PubMed PMID: 20702858; PubMed Central PMCID: PMCJournal—In Process.

Ford K. R., Shapiro R, Myer G. D., Van Den Bogert A. J., Hewett T. E. Longitudinal sex differences during landing in knee abduction in young athletes. Med Sci Sports Exerc. 2010;42(10):1923-31. Epub Mar. 23, 2010. doi: 10.1249/MSS.0b013e3181dc99b1. PubMed PMID: 20305577; PubMed Central PMCID: PMC2924455.

Myer G. D., Chu D. A., Brent J. L., Hewett T. E. Trunk and hip control neuromuscular training for the prevention of knee joint injury. Clin Sports Med. 2008;27(3):425-48, ix. Epub May 28, 2008. doi: S0278-5919(08)00022-7 [pii]10.1016/j.csm.2008.02.006 [doi], PubMed PMID: 18503876; PubMed Central PMCID: PMC2586107.

Myer G. D., Brent J. L., Ford K. R., Hewett T.E. A pilot study to determine the effect of trunk and hip focused neuromuscular training on hip and knee isokinetic strength. Br J Sports Med. 2008;42(7):614-9. doi: 10.1136/bjsm.2007.046086. PubMed PMID: 18308886; PubMed Central PMCID: PMC4003571.

Ford K. R., Myer G. D., Hewett T. E. Valgus knee motion during landing in high school female and male basketball players. Med Sci Sports Exerc. 2003;35(10):1745-50. PubMed PMID: 14523314.

Cowley H. R., Ford K. R., Myer G. D., Kernozek T. W., Hewett T. E. Differences in neuromuscular strategies between landing and cutting tasks in female basketball and soccer athletes. J Athl Train. 2006;41(1):67-73. PubMed PMID: WOS:000236595800011; PubMed Central PMCID: PMC1421490.

Imwalle L. E., Myer G. D., Ford K. R., Hewett T. E. Relationship between hip and knee kinematics in athletic women during cutting maneuvers: a possible link to noncontact anterior cruciate ligament injury and prevention. J Strength Cond Res. 2009;23(8):2223-30. Epub Oct. 15, 2009. doi: 10.1519/JSC.0b013e3181bc1a02. PubMed PMID: 19826304; PubMed Central PMCID: PMC3565241.

Alentorn-Geli E., Myer G. D., Silvers H. J., Samitier G., Romero D., Lazaro-Haro C., Cugat R. Prevention of non-contact anterior cruciate ligament injuries in soccer players. Part 1: Mechanisms of injury and underlying risk factors. Knee Surg Sports Traumatol Arthrosc. 2009;17(7):705-29. Epub May 20, 2009. doi: 10.1007/s00167-009-0813-1. PubMed PMID: 19452139; PubMed Central PMCID: PMCJournal—In Process.

Brown T. N., Palmieri-Smith R. M., McLean S. G. Comparative Adaptations of Lower Limb Biomechanics during Uni-Lateral and Bi-Lateral Landings after Different Neuromuscular-Based ACL Injury Prevention Protocols. J Strength CondRes. 2014. Epub Apr.

(56) References Cited

OTHER PUBLICATIONS 10, 2014. doi: 10.1519/jsc.0000000000000472. PubMed PMID: 24714537; PubMed Central PMCID: PMCJournal—In Process.

Sugimoto D., Myer G. D., Bush H. M., Hewett T. E. Effects of compliance on trunk and hip integrative neuromuscular training on hip abductor strength in female athletes. J Strength Cond Res. 2014;28(5):1187-94. Epub Apr. 23, 2014. doi: 10.1097/JSC. 0000000000000228. PubMed PMID: 24751656; PubMed Central PMCID: PMC4170915.

Barber Foss K. D., Myer G. D., Hewett T. E. Epidemiology of basketball, soccer, and volleyball injuries in middle-school female athletes. Phys Sportsmed. 2014;42(2):146-53. doi: 10.3810/psm. 2014.05.2066. PubMed PMID: 24875981; PubMed Central PMCID: PMC4217285.

Chaudhari A. M., Lindenfeld T. N., Andriacchi T. P., Hewett T. E., Riccobene J., Myer G. D., Noyes F. R. Knee and hip loading patterns at different phases in the menstrual cycle: implications for the gender difference in anterior cruciate ligament injury rates. Am J Sports Med. 2007;35(5):793-800. Epub Feb. 20, 2007. doi: 0363546506297537 [pii]10.1177/0363546506297537 [doi]. PubMed PMID: 17307891.

Hewett T. E, Zazulak B. T., Myer G. D. Effects of the menstrual cycle on anterior cruciate ligament injury risk: a systematic review. Am J Sports Med. 2007;35(4):659-68. Epub Feb. 13, 2007. doi: 0363546506295699 [pii]10.1177/0363546506295699 [doi]. PubMed PMID: 17293469.

Myer G. D., Ford K. R., Paterno M. V., Nick T. G., Hewett T. E. The effects of generalized joint laxity on risk of anterior cruciate ligament injury in young female athletes. Am J Sports Med. 2008;36(6):1073-80. Epub Mar. 11, 2008. doi: 0363546507313572 [pii]10.1177/0363546507313572. PubMed PMID: 18326833; PubMed Central PMCID: PMC3407802.

Myer G. D., Ford K. R., Divine J. G., Wall E. J., Kahanov L., Hewett T. E. Longitudinal assessment of noncontact anterior cruciate ligament injury risk factors during maturation in a female athlete: a case report. J Athl Train. 2009;44(1):101-9. Epub Jan. 31, 2009. doi: 10.4085/1062-6050-44.1.101. PubMed PMID: 19180226; PubMed Central PMCID: PMC2629034.

Myer G. D., Ford K. R., Barber Foss K. D., Liu C., Nick T. G., Hewett T. E. The relationship of hamstrings and quadriceps strength to anterior cruciate ligament injury in female athletes. Clin J Sport Med. 2009;19(1):3-8. Epub Jan. 7, 2009. doi: 10.1097/JSM. 0b013e318190bddb00042752-200901000-00002 [pii]. PubMed PMID: 19124976; PubMed Central PMCID: PMCJournal—In Process.

Myer G. D., Ford K. R., Brent J. L., Hewett T. E. An integrated approach to change the outcome part I: neuromuscular screening methods to identify high ACL injury risk athletes. J Strength Cond Res. 2012;26(8):2265-71. Epub May 15, 2012. doi: 10.1519/JSC. 0b013e31825c2b8f. PubMed PMID: 22580976; PubMed Central PMCID: PMC4160042.

Myer G. D., Ford K. R., Brent J. L., Hewett T. E. An integrated approach to change the outcome part II: targeted neuromuscular training techniques to reduce identified ACL injury risk factors. J Strength Cond Res. 2012;26(8):2272-92. Epub May 15, 2012. doi: 10.1519/JSC.0b013e31825c2c7d. PubMed PMID: 22580980; PubMed Central PMCID: PMC4159730.

Decker M. J., Torry M. R., Wyland D. J., Sterett W. I., Richard Steadman J. Gender differences in lower extremity kinematics, kinetics and energy absorption during landing. Clin Biomech. 2003;18(7):662-9. PubMed PMID: 12880714.

Myer G. D., Ford K. R., Di Stasi S. L., Foss K. D., Micheli L. J., Hewett T. E. High knee abduction moments are common risk factors for patellofemoral pain (PFP) and anterior cruciate ligament (ACL) injury in girls: Is PFP itself a predictor for subsequent ACL injury? Br J Sports Med. 2015;49(2):118-22. Epub Apr. 2, 2014. doi: 10.1136/bjsports-2013-092536. PubMed PMID: 24687011; PubMed Central PMCID: PMC4182160.

Lephart S. M., Abt J. P., Ferris C. M., Sell T. C., Nagai T., Myers J. B., Irrgang J. J. Neuromuscular and biomechanical characteristic changes in high school athletes: a plyometric versus basic resistance program. Br J Sports Med. 2005;39(12):932-8. PubMed PMID: 16306502; PubMed Central PMCID: PMC1725089.

Dolak K. L., Silkman C., Medina McKeon J., Hosey R. G., Lattermann C., Uhl T. L. Hip strengthening prior to functional exercises reduces pain sooner than quadriceps strengthening in females with patellofemoral pain syndrome: a randomized clinical trial. J Orthop Sports Phys Ther. 2011;41(8):560-70. doi: 10.2519/ jospt.2011.3499. PubMed PMID: 21654093; PubMed Central PMCID: PMCJournal—In Process.

Khayambashi K., Mohammadkhani Z., Ghaznavi K., Lyle M. A., Powers C. M. The effects of isolated hip abductor and external rotator muscle strengthening on pain, health status, and hip strength in females with patellofemoral pain: a randomized controlled trial. J Orthop Sports Phys Ther. 2012;42(1):22-9. doi: 10.2519/jospt. 2012.3704. PubMed PMID: 22027216; PubMed Central PMCID: PMCJournal—In Process.

Shultz S. J., Nguyen A. D., Schmitz R. J. Differences in lower extremity anatomical and postural characteristics in males and females between maturation groups. J Orthop Sports Phys Ther. 2008;38(3):137-49. Epub Apr. 4, 2008. PubMed PMID: 18383647.

Zazulak B. T., Ponce P. L., Straub S. J., Medvecky M. J., Avedisian L., Hewett T. E. Gender comparison of hip muscle activity during single-leg landing. J Orthop Sports Phys Ther. 2005;35(5):292-9. PubMed PMID: 15966540.

Hewett T. E., Myer G. D., Ford K. R. Reducing knee and anterior cruciate ligament injuries among female athletes: a systematic review of neuromuscular training interventions. J Knee Surg. 2005;18(1):82-8. PubMed PMID: 15742602.

Hewett T. E., Stroupe A. L., Nance T. A., Noyes F. R. Plyometric training in female athletes. Decreased impact forces and increased hamstring torques. Am J Sports Med. 1996;24(6):765-73.

Myer G. D., Ford K. R., Brent J. L., Hewett T. E. The Effects of Plyometric versus Dynamic Balance Training on Power, Balance and Landing Force in Female Athletes. J Strength Cond Res. 2006;20(2):345-53.

Wulf G., Prinz W. Directing attention to movement effects enhances learning: A review. Psychonomic bulletin & review. 2001;8(4):648-60.

McNevin N. H., Shea C. H., Wulf G. Increasing the distance of an external focus of attention enhances learning. Psychol Res. 2003;67(1):22-9.

Shea C. H., Wulf G. Enhancing motor learning through external-focus instructions and feedback. Human Movement Science. 1999;18(4):553-71.

Wulf G., McNevin N. Simply distracting learners is not enough: More evidence for the learning benefits of an external focus of attention. European Journal of Sport Science. 2003 ;3(5):1-13.

Zachry T., Wulf G., Mercer J., Bezodis N. Increased movement accuracy and reduced EMG activity as the result of adopting an external focus of attention. Brain Res Bull. 2005;67(4):304-9.

Wulf G., Shea C., Lewthwaite R. Motor skill learning and performance: a review of influential factors. Med Educ. 2010;44(1):75-84. doi: 10.1111/j.1365-2923.2009.03421.x. PubMed PMID: 20078758; PubMed Central PMCID: PMCJournal—In Process.

Shea C. H., Wulf G., Whitacre C. A., Park J. H. Surfing the implicit wave. The Quarterly Journal of Experimental Psychology: Section A. 2001;54(3):841-62.

Brenner E, Smeets JB. Quickly 'learning' to move optimally. Exp Brain Res. 2011;213(1):153-61; PubMed Central PMCID: PMC3140948.

Wang C. Y., Kennedy D. M., Boyle J. B., Shea C. H. A guide to performing difficult bimanual coordination tasks: just follow the yellow brick road. Exp Brain Res. 2013;230(1):31-40. doi: DOI 10.1007/s00221-013-3628-8. PubMed PMID: WOS:000323739400003; PubMed Central PMCID: PMCJournal—In Process.

Fernandez L., Bootsma R. J. Non-linear gaining in precision aiming: making Fitts' task a bit easier. Acta Psychol (Amst). 2008;129(2):217-27. doi: 10.1016/j.actpsy.2008.06.001. PubMed PMID: 18632086; PubMed Central PMCID: PMCJournal—In Process.

Kovacs A. J., Buchanan J. J., Shea C. H. Bimanual 1:1 with 90 degrees continuous relative phase: difficult or easy ! Exp Brain Res.

(56) References Cited

OTHER PUBLICATIONS

2009;193(1):129-36. doi: 10.1007/s00221-008-1676-2. PubMed PMID: 19093104; PubMed Central PMCID: PMCJournal—In Process.
Kovacs A. J., Buchanan J. J., Shea C. H. Perceptual influences on Fitts' law. Exp Brain Res. 2008;190(1):99-103. doi: 10.1007/s00221-008-1497-3. PubMed PMID: 18648783; PubMed Central PMCID: PMCJournal—In Process.
Mechsner F. A psychological approach to human voluntary movements. J Mot Behav. 2004.
Pawlak W. S., Vicente K. J. Inducing effective operator control through ecological interface design. International Journal of Human-Computer Studies. 1996;44(5):653-88.
Fowler C. A., Turvey M. Skill acquisition: An event approach with special reference to searching for the optimum of a function of several variables. Information processing in motor control and learning. 1978:1-40.
Faugloire E., Bardy B. G., Merhi O., Stoffregen T. A. Exploring coordination dynamics of the postural system with real-time visual feedback. Neurosci Lett. 2005;374(2):136-41.
Paterno M. V., Myer G. D., Ford K. R., Hewett T. E. Neuromuscular training improves single-limb stability in young female athletes. J Orthop Sports Phys Ther. 2004;34(6):305-17.
Filipa A., Byrnes R., Paterno M. V, Myer G. D. , Hewett T. E. Neuromuscular training improves performance on the star excursion balance test in young female athletes. J Orthop Sports Phys Ther. 2010;40(9):551-8. Epub Aug. 17, 2010. doi: 2475 [pii]10.2519/jospt.2010.3325. PubMed PMID: 20710094; PubMed Central PMCID: PMC3439814.
Ford K. R., Manson N. A., Evans B. J., Myer G. D., Gwin R. C., Heidt R. S., Jr., Hewett T. E. Comparison of in-shoe foot loading patterns on natural grass and synthetic turf. J Sci Med Sport. 2006;9(6):433-40. doi: 10.1016/j.jsams.2006.03.019. PubMed PMID: 16672191.
Ford K. R., Myer G. D., Hewett T. E. Reliability of landing 3D motion analysis: implications for longitudinal analyses. Med Sci Sports Exerc. 2007;39(11):2021-8. Epub Nov. 8, 2007. doi: 10.1249/mss.0b013e318149332d00005768-200711000-00018 [pii], PubMed PMID: 17986911.
Ford K. R., Myer G. D., Smith R. L., Byrnes R. N., Dopirak S. E., Hewett T. E. Use of an overhead goal alters vertical jump performance and biomechanics. Journal of Strength and Conditioning Research. 2005;19(2):394-9. PubMed PMID: 15903381.
Ford K. R., Myer G. D., Brent J. L., Hewett T. E. Hip and knee extensor moments predict vertical jump height in adolescent girls. J Strength Cond Res. 2009;23(4):1327-31. Epub Jun. 17, 2009. doi: 10.1519/JSC.0b013e31819bbea4. PubMed PMID: 19528842; PubMed Central PMCID: PMC4010199.
Myer G. D., Brent J. L., Ford K. R., Hewett T. E. Real-time assessment and neuromuscular training feedback techniques to prevent ACL injury in female athletes. Strength Cond J. 2011;33(3):21-35. Epub Jun. 7, 2011. doi: 10.1519/SSC.0b013e318213afa8. PubMed PMID: 21643474; PubMed Central PMCID: PMC3105897.
McCutcheon A. L. Latent Class Analysis. Newbury Park, Calif: Sage; 1987. 96 p.
McLachlan G. J., Peel D. Finite mixture models. New York: Wiley; 2000. xxii, 419 p. p.
Muthen L., Muthen B. Mplus User's Guide. 3rd ed. Los Angeles, CA: Muthen & Muthen; 1998-2008.
Lo Y., Mendell N., Rubin D. Testing the number of components in a normal mixture. Biometrika. 2001;88:767-78.
Nylund K. L., Asparouhov T., Muthen B. O. Deciding on the number of classes in latent class analysis and growth mixture modeling: A Monte Carlo simulation study. Structural Equation Modeling 2007;14:535-69.
Little R. J., D'Agostino R., Cohen M. L., Dickersin K., Emerson S. S., Farrar J. T., Frangakis C., Hogan J. W., Molenberghs G., Murphy S. A., Neaton J. D., Rotnitzky A., Scharfstein D., Shih W. J., Siegel J. P., Stern H. The prevention and treatment of missing data in clinical trials. N Engl J Med. 2012;367(14):1355-60. Epub Oct. 5, 2012. doi: 10.1056/NEJMsr1203730. PubMed PMID: 23034025; PubMed Central PMCID: PMC3771340.
Little R. J., Rubin D. B. Statistical analysis with missing data 2002.
Rosenbaum P. R., Rubin D. B. The central role of the propensity score in observational studies for causal effects. Biometrika. 1983;70(1):41-55.
Myer G. D., Ford K. R., Khoury J., Succop P., Hewett T. E. Biomechanics laboratory-based prediction algorithm to identify female athletes with high knee loads that increase risk of ACL injury. Br J Sports Med. 2011;45(4):245-52. Epub Jun. 19, 2010. doi: 10.1136/bjsm.2009.069351. PubMed PMID: 20558526; PubMed Central PMCID: PMC4019975.
Piazza S. J., Cavanagh P. R. Measurement of the screw-home motion of the knee is sensitive to errors in axis alignment. J Biomech. 2000;33(8):1029-34. PubMed PMID: 10828334.
Ramakrishnan H. K., Kadaba M. P. On the estimation of joint kinematics during gait. JBiomech. 1991;24(10):969-77. PubMed PMID: 1744154.
Delecluse C., Van Coppenolle H., Willems E., VanLeemputte M., Diels R., Goris M. Influence of high-resistance and high-velocity training on sprint performance. Med Sci Sports Exerc. 1995;27(8):1203-9. PubMed PMID: 7476066.
Rimmer E., Sleivert G. Effects of a plyometrics intervention program on sprint performance. The Journal of Strength & Conditioning Research. 2000;14(3):295-301.
Campo S. S., Vaeyens R., Philippaerts R. M., Redondo J. C., de Benito A. M., Cuadrado G. Effects of lower-limb plyometric training on body composition, explosive strength, and kicking speed in female soccer players. The Journal of Strength & Conditioning Research. 2009;23(6):1714-22; PubMed Central PMCID: PMCJournal—In Process.
Shallaby H. K. The Effect of Plyometric Exercises Use on the Physical and Skillful Performance of Basketball Players. World. 2010;3(4):316-24; PubMed Central PMCID: PMCJournal—In Process.
Sharma D., Kaur Multani N. Effectiveness of Plyometric Training in the Improvement of Sports Specific Skills of Basketball Players. Indian Journal of Physiotherapy & Occupational Therapy. 2012;6(1); PubMed Central PMCID: PMCJournal—In Process.
Caraffa A., Cerulli G., Projetti M., Aisa G, Rizzo A. Prevention of anterior cruciate ligament injuries in soccer. A prospective controlled study of proprioceptive training. Knee Surg Sports Traumatol Arthrosc. 1996;4(1):19-21.
Gilchrist J., Mandelbaum B. R., Melancon H., Ryan G. W, Silvers H. J., Griffin L. Y., Watanabe D. S., Dick R. W., Dvorak J. A randomized controlled trial to prevent noncontact anterior cruciate ligament injury in female collegiate soccer players. Am J Sports Med. 2008;36(8):1476-83. PubMed PMID: 18658019; PubMed Central PMCID: PMCJournal—In Process.
Bonnechere B., Jansen B., Salvia P., Bouzahouene H., Omelina L., Moiseev F., Sholukha V., Cornelis J., Rooze M., Van Sint Jan S. Validity and reliability of the Kinect within functional assessment activities: comparison with standard stereophotogrammetry. Gait Posture. 2014;39(1):593-8. Epub Nov. 26, 2013. doi: 10.1016/j.gaitpost.2013.09.018. PubMed PMID: 24269523.
Smith H. C., Johnson R. J., Shultz S. J., Tourville T., Holterman L. A., Slauterbeck J., Vacek . M, Beynnon B. D. A prospective evaluation of the Landing Error Scoring System (LESS) as a screening tool for anterior cruciate ligament injury risk. Am J Sports Med. 2012;40(3):521-6. Epub Nov. 26, 2011. doi: 10.1177/0363546511429776. PubMed PMID: 22116669.
Bideau B., Multon F., Kulpa R., Fradet L., Arnaldi B., Delamarche P. Using virtual reality to analyze links between handball thrower kinematics and goalkeeper's reactions. Neurosci Lett. 2004;372(1-2):119-22. Epub Nov. 9, 2004. doi: 10.1016/j.neulet.2004.09.023. PubMed PMID: 15531100.
Watson G., Brault S., Kulpa R., Bideau B., Butterfield J, Craig C. Judging the 'passability' of dynamic gaps in a virtual rugby environment. Human Movement Science. 2011;30(5):942-56; PubMed Central PMCID: PMCJournal—In Process.
Kulpa R., Bideau B., Brault S. Displacements in Virtual Reality for sports performance analysis. Human walking in virtual environments: Springer; 2013. p. 299-318.

(56) References Cited

OTHER PUBLICATIONS

Bideau B., Kulpa R., Vignais N., Brault S., Multon F., Craig C. Using virtual reality to analyze sports performance. IEEE computer graphics and applications. 2010;30(2):14-21. Epub Jul. 24, 2010. doi: 10.1109/MCG.2009.134. PubMed PMID: 20650707; PubMed Central PMCID: PMCJournal—In Process.

Bliss J. P., Tidwell P. D., Guest MA. The effectiveness of virtual reality for administering spatial navigation training to firefighters. Presence-Teleoperators and Virtual Environments. 1997;6(1):73-86.

Lintern G., Roscoe S. N., Koonce J. M., Segal L. D. Transfer of landing skills in beginning flight training. Human Factors: The Journal of the Human Factors and Ergonomics Society. 1990;32(3):319-27.

Rose F., Attree E., Brooks B., Parslow D., Penn P. Training in virtual environments: transfer to real world tasks and equivalence to real task training. Ergonomics. 2000;43(4):494-511.

Seymour N. E., Gallagher A. G., Roman S. A., O'Brien M. K., Bansal V. K., Andersen D. K., Satava R. M. Virtual reality training improves operating room performance: results of a randomized, double-blinded study. Ann Surg. 2002;236(4):458.

Fink P. W., Foo P. S., Warren W. H. Obstacle avoidance during walking in real and virtual environments. ACM Transactions on Applied Perception (TAP). 2007;4(1):2.

Arendt, E., & Dick, R. (1995), Knee injury patterns among men and women in collegiate basketball and soccer: NCAA data and review of literature. The American Journal of Sports Medicine, 23(6), 694-701.

Barrios, J. A., Crossley, K. M., & Davis, I.S. (2010). Gait retraining to reduce the knee adduction moment through real-time visual feedback of dynamic knee alignment. Journal of Biomechanics, 43(11), 2208-2213.

Benjaminse, A., Welling, W., Otten, B., & Gokeler, A. (2017). Transfer of improved movement technique after receiving verbal external focus and video instuction. Knee Surgery, Sports Traumatology, Arthroscopy, 1-8.

Crowell, H. P., & Davis, I. S. (2011). Gait retraining to reduce lower extremity loading in runners. Clinical Biomechanics, 26(1), 78-83.

Ericksen, H. M., Thomas, A. C., Gribble, P. A., Armstrong, C., Rice, M., & Pietrosimone, B. (2016). Jump-landing biomechanics following a 4-week real-time feedback intervention and retention. Clinical Biomechanics, 32, 85-91.

Ericksen, H. M., Thomas, A. C., Gribble, P. A., Doebel, S. C., & Pietrosimone, B. G. (2015). Immediate effects of real-time feedback on jump-landing kinematics, Journal of Orthopaedic and Sports Physical Therapy, 45(2), 112-118.

Gokeler, A., Benjaminse, A., Welling, W., Alferink, M., Eppinga, P., & Otten, B. (2015). The effects of attentional focus on jump performance and knee joint kinematics in patients after ACL reconstruction. Physical Therapy in Sport 16(2), 114-120.

Kushner, A. M., Brent, J. L., Schoenfeld, B. J., Hugentobler, J., Lloyd, R. S., Vermeil, A., Myer, G. D. (2015). The back squat part 2: Target training techniques to correct functional deficits and technical factors that limit performance. Strength and conditioning journal, 37(2), 13-60.

Myer, G. D., Kushner, A. M., Brent, J. L., Schoenfeld, B. J., Hugentobler, J., Lloyd, R. S., McGill, S. M. (2014). The back squat: A proposed assessment of functional deficits and technical factors that limit performance. Strength and conditioning journal, 36(6), 4.

Noehren, B., Scholz, J., & Davis, I. (2010). The effect of real-time gait retraining on hip kinematics, pain and function in subjects with patellofemoral pain syndrome. British Journal of Sports Medicine, bjsports69112.

Waynes, G., & Klippel, J. (2010). A National Public Health Agenda for Osteoarthritis. Centers for Disease Control and Prevention and the Arthritis, 1-62.

Yoo, J. H., Lim, B. O., Ha, M., Lee, S. W. Oh, S. J., Lee, Y. S., & Kim, J. G. (2010). A meta-analysis of the effect of neuromuscular training on the prevention of the anterior cruciate ligament injury in female athletes. Knee Surgery, Sports Traumatology, Arthroscopy, 18(6), 824-830.

Gibson JJ. The ecological approach to the visual perception of pictures. Leonardo. 1978: 227-235.

Warren WH. The dynamics of perception and action. Psychol Rev. 2006: 113(2): 358.

Motion Analysis Corporation, Kestrel Digital RealTime System, printed on Nov. 8, 2017 from www.motionanalysis.com.

Motion Analysis Corporation, Cortex, printed on Nov. 8, 2017 from www.motionanalysis.com.

Gibson J. J. The perception of the visual world. Boston: Houghton Mifflin 1950. 235 p.

\* cited by examiner

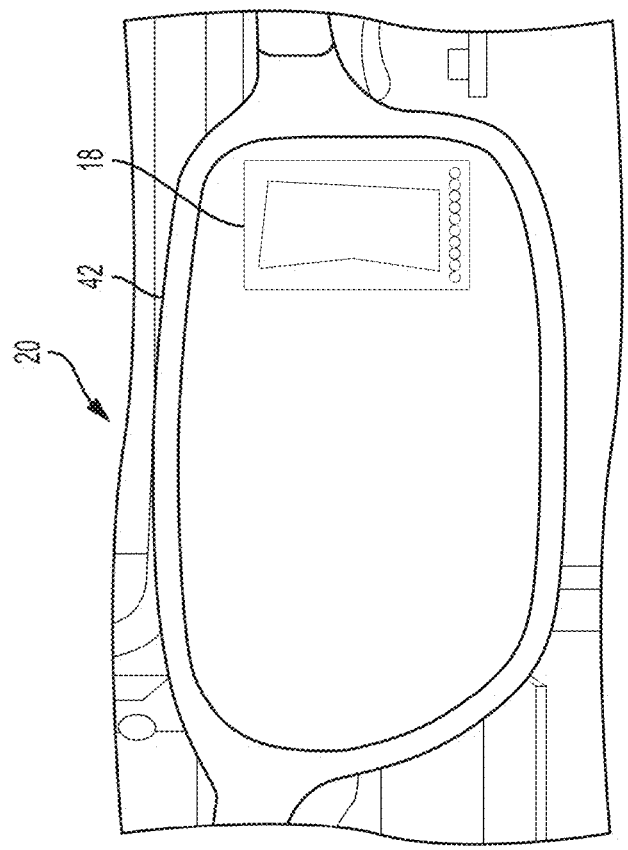
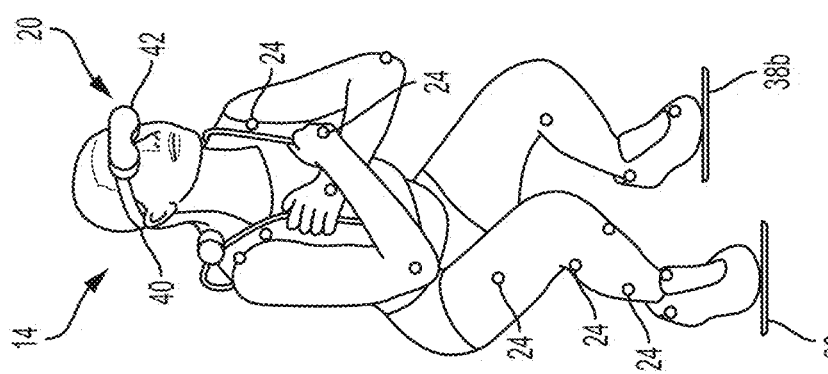

| STEP | FILES |
|---|---|
| PROGRAM START | "STIMULUSXML.CS" |
| 1 | "POINT.CS" "USERHANDLER.CS" |
| INPUT STREAM | "ANMT.CS" |
| 2/3 | "AUDIOHANDLER.CS" "TRACKER.CS" "REPCOUNTER.CS" "SCORE.CS" |

| STEP | FILES |
|---|---|
| 4 | "OH_SQUATS.CS" "PISTOL_SQUATS.CS" "SQUAT_JUMP.CS" |
| 5 | "SHAME.CS" "IMPORTSHAM.CS" |
| 6 | "DEFORMATIONHANDLER.CS" |

Figure 13

| FILE/CLASS | FUNCTION | LABEL | DESCRIPTION |
|---|---|---|---|
| AudioHandler.cs | - | - | - |
| XMLMap.cs | - | - | - |
| anm.cs | start() | 1.A | INITIALIZES CONNECTION TO BIOMECHANICAL DATA STREAM SOURCE |
| | update() | 1.B | READS NEW BIOMECHANICAL DATA FRAME |
| | onApplicationQuit() | 1.C | END CONNECTION TO BIOMECHANICAL DATA STREAM SOURCE |
| importSham.cs | loadFile() | 2.A | IMPORTS SHAM DATA FROM RANDOM TEXT FILE |
| math_F.cs | norm() | 3.A | RETURNS NORM OF A VECTOR |
| | cross() | 3.A | RETURNS CROSS PRODUCT OF TWO VECTORS |
| OH_Squat.cs | calc_OH_Squat() | 4.A | CALLS ALL SUBFUNCTIONS BELOW (4.B-4.L) |
| | calc_trunkMod() | 4.B | CALCULATES TRUNK POSITION VARIABLE VALUE |
| | calc_Arm() | 4.C | CALCULATES THE ARM VARIABLE VALUE |
| | calc_TrnkLn() | 4.D | CALCULATES TRUNK VARIABLE VALUE |
| | calc_vGRF() | 4.E | CALCULATES GROUND REACTION FORCE VARIABLE VALUE |
| | calc_Knee() | 4.F | CALCULATES THE KNEE VARIABLE VALUE |
| | calc_KneeHip() | 4.G | CALCULATES THE KNEE/HIP VARIABLE VALUE |
| | disp_TrnkLn() | 4.H | MODIFIES STIMULUS BASED ON TRUNK VARIABLE VALUE |
| | disp_Arm() | 4.I | MODIFIES STIMULUS BASED ON ARM VARIABLE VALUE |
| | disp_Knee() | 4.J | MODIFIES STIMULUS BASED ON KNEE VARIABLE VALUE |
| | disp_vGRF | 4.K | MODIFIES STIMULUS BASED ON GROUND REACTION FORCE VARIABLE VALUE |
| | disp_Hip() | 4.L | MODIFIES STIMULUS BASED ON KNEE/HIP VARIABLE VALUE |
| Sham.cs | calc_Rect() | 5.A | CALCULATES MAX RANGE OF SHAM VALUES |
| | add_Sham() | 5.B | MODIFIES STIMULUS BY INTEGRATING THE SHAM FEEDBACK |
| | disp_Sham() | 5.C | DISPLAYS SHAM FEEDBACK |
| | calc_vGRF() | 5.F | CALCULATES GROUND REACTION FORCE VARIABLE VALUE |
| | calc_TrnkLn() | 5.G | CALCULATES TRUNK POSITION VARIABLE VALUE |
| | disp_Sham_TrnkLn() | 5.E | MODIFIES STIMULUS BASED ON TRUNK VARIABLE VALUE & LOCATION |
| | disp_vGRF | 5.D | MODIFIES STIMULUS BASED ON GROUND REACTION FORCE VARIABLE VALUE & LOCATION |

*Figure 14*

| FILE/CLASS | FUNCTION | LABEL | DESCRIPTION |
|---|---|---|---|
| Squat.cs | calc_Squat() | 6.A | CALLS ALL SUBFUNCTIONS BELOW (6.B-6.J) |
| | calc_trunkMod() | 6.B | CALCULATES TRUNK POSITION VARIABLE VALUE |
| | calc_TrnkLn() | 6.C | CALCULATES TRUNK VARIABLE VALUE |
| | calc_vGRF() | 6.D | CALCULATES THE FORCES PRODUCED AT EACH FOOT |
| | calc_Knee() | 6.E | CALCULATES THE KNEE VARIABLE VALUE |
| | calc_KneeHip() | 6.F | CALCULATES THE KNEE/HIP VARIABLE VALUE |
| | disp_TrnkLn | 6.G | MODIFIES STIMULUS BASED ON TRUNK VARIABLE VALUE |
| | disp_vGRF | 6.H | MODIFIES STIMULUS BASED ON KNEE VARIABLE VALUE |
| | disp_Knee() | 6.I | MODIFIES STIMULUS BASED ON GROUND REACTION FORCE VARIABLE VALUE |
| | disp_Hip() | 6.J | MODIFIES STIMULUS BASED ON KNEE/HIP VARIABLE VALUE |
| Pistol_Squat.cs | calc_PistSquat | 7.A | CALLS ALL SUBFUNCTIONS BELOW (7.B-7.I) |
| | calc_TrnkLn | 7.B | CALCULATES TRUNK VARIABLE VALUE |
| | calc_KneeVal() | 7.C | CALCULATES THE KNEE VARIABLE VALUE |
| | calc_Hip_PS | 7.D | CALCULATES THE HIP VARIABLE VALUE |
| | calc_PelvisDrop | 7.E | CALCULATES THE PELVIS VARIABLE VALUE |
| | disp_HipAdd | 7.F | MODIFIES STIMULUS BASED ON HIP VARIABLE VALUE |
| | disp_PelDrp | 7.G | MODIFIES STIMULUS BASED ON PELVIS VARIABLE VALUE |
| | disp_Knee_P | 7.H | MODIFIES STIMULUS BASED ON KNEE VARIABLE VALUE |
| | disp_TrnkLn | 7.I | MODIFIES STIMULUS BASED ON TRUNK VARIABLE VALUE |
| Squat_Jump.cs | calc_Squat_Jump() | 8.A | CALLS ALL SUBFUNCTIONS BELOW (8.B-8.J) |
| | calc_trunkMod() | 8.B | CALCULATES TRUNK POSITION VARIABLE VALUE |
| | calc_TrnkLn() | 8.C | CALCULATES TRUNK VARIABLE VALUE |
| | calc_vGRF() | 8.D | CALCULATES THE FORCES PRODUCED AT EACH FOOT |
| | calc_Knee() | 8.E | CALCULATES THE KNEE VARIABLE VALUE |
| | calc_KneeHip() | 8.F | CALCULATES THE KNEE/HIP VARIABLE VALUE |
| | disp_TrnkLn | 8.G | MODIFIES STIMULUS BASED ON TRUNK VARIABLE VALUE |
| | disp_vGRF | 8.H | MODIFIES STIMULUS BASED ON KNEE VARIABLE VALUE |

*Figure 14 Continued*

| FILE/CLASS | FUNCTION | LABEL | DESCRIPTION |
|---|---|---|---|
| Tracker.cs | disp_Knee() | 8.I | MODIFIES STIMULUS BASED ON GROUND REACTION FORCE VARIABLE VALUE |
| | disp_Hip() | 8.J | MODIFIES STIMULUS BASED ON KNEE/HIP VARIABLE VALUE |
| | calc_Depth() | 9.A | CALCULATES RANGE OF MOTION FOR AN EXERCISE |
| | calc_InAir() | 9.B | DETERMINES IF A USER IS JUMPING |
| | calc_FootWidth() | 9.C | CALCULATES CORRECT POSITIONING OF FEET |
| | calc_Newtons() | 9.D | CALCULATES A USERS FORCE IN NEWTONS |
| | calc_Height() | 9.E | CALCULATES USERS HEIGHT IN METERS |
| | chck_Foot() | 9.F | CHECKS FOR CORRECT FOOT POSITIONING |
| Point.cs | avgWindow() | 10.A | AVERAGES LAST SET OF POINT VALUES INTO A SINGLE FRAME |
| | updatePoint() | 10.B | UPDATES INFORMATION ABOUT POINTS |
| | ToString() | 10.C | CONVERTS NUMERICAL VALUE TO STRING VALUE |
| | Point() | 10.D | INITIALIZES INFORMATION ABOUT POINTS |
| RepCounter.cs | countReps() | 11.A | TRACKS NUMBER OF REPETITIONS COMPLETED |
| | failedReps() | 11.B | DETERMINES IF USER PERFORMED A FAILED REPETITION |
| | squatStart() | 11.C | DETERMINES IF USER HAS STARTED EXERCISE |
| Score.cs | getScore() | 12.A | CALCULATES USER SCORE |
| | saveScore() | 12.B | EXPORTS SCORE TO AN EXTERNAL TEXT FILE |
| GUIManager.cs | OpenSelected() | 13.A | CONTROLS GUI CALLS FOR INDIVIDUAL EXERCISES |
| | onEnable() | 13.B | CHECK FOR SELECTED EXERCISE |
| | ConnectToggle() | 13.C | CONNECT TO BIOMECHANICAL DATA SOURCE |
| | DisplayButtonClicked() | 13.D | CONNECT TO DISPLAY DEVICE |
| | ClosePrevious() | 13.E | CLOSES PREVIOUS CONNECTIONS |
| | sideToggle() | 13.F | DETERMINES LEG FOR PISTOL SQUAT |
| | nextSet() | 13.G | RESETS DATA FOR NEXT EXERCISE SET |
| | Update() | 13.H | UPDATE INFORMATION ABOUT GUI |
| stimulusXML.cs | Start() | 14.A | STARTS PROGRAM |
| | FixedUpdate() | 14.B | UPDATES ENTIRE PROGRAM ON FIXED INTERVAL |

*Figure 14 Continued*

| FILE/CLASS | FUNCTION | LABEL | DESCRIPTION |
|---|---|---|---|
| UserHandler.cs | getID() | 15.A | LOADS USER IDENTIFICATION NUMBER |
| | load_info() | 15.B | LOADS USER INFORMATION |
| | save_info() | 15.C | SAVES USER INFORMATION |
| | new_part() | 15.D | CREATES NEW USER |
| | edit_part() | 15.E | EDITS EXISTING USER |
| TCPServerXML.cs | onApplicationQuit() | 16.A | TERMINATES CONNECTIONS |
| | Update() | 16.B | UPDATES CONNECTIONS |
| | checkConnections() | 16.C | CHECK FOR EXISTING CONNECTIONS |
| | SerializeObject() | 16.D | PREPARES XML DATA FRAME FOR TRANSMISSION TO DISPLAY DEVICE |
| | Start() | 16.E | INITIALIZES CONNECTION |

*Figure 14 Continued*

| DATA STRUCTURES | | |
|---|---|---|
| DATA STRUCTURE | FUNCTIONS INVOLVED | DESCRIPTION |
| bioM_Data | 1, 4, and 7-11 | CONTAINS ALL BIOMECHANICAL DATA |
| stim_XML | 4-8, 10, 12, 14, & 16 | CONTAINS ALL INFORMATION FOR CREATING AND CONTROLLING STIMULUS |
| user_Data | 15 | CONTAINS INFORMATION ABOUT USER |

*Figure 15*

AUGMENTED NEUROMUSCULAR TRAINING SYSTEM AND METHOD

CROSS-REFERENCE TO RELATED APPLICATION

The present application claims priority to U.S. Provisional Patent Application Ser. No. 62/420,119, filed Nov. 10, 2016, the disclosure of which is expressly incorporated herein by reference.

STATEMENT OF GOVERNMENT INTEREST

This invention was made with government support under NIH AR067997 awarded by the National Institutes of Health. The Government has certain rights in the invention.

BACKGROUND OF THE DISCLOSURE

The present disclosure relates to an augmented neuromuscular training system and method, and more particularly, to a system and method for modifying movement deficits associated with injury risk, prior injury or disease pathology, such as risk factors for anterior cruciate ligament injuries in athletes through real-time visual feedback.

Movement deficits associated with injury risk, prior injury or disease pathology present a significant medical concern. For example, anterior cruciate ligament (ACL) injuries are a growing public health problem in the United States, with associated healthcare costs exceeding $2 billion annually. Females are more likely to incur an ACL injury, and in recent years adolescent females (i.e., 14-17 year olds) have experienced the largest increase in ACL injury rate. A large amount of research has investigated and identified several potential risk factors for ACL injuries in females. Prevention of ACL injuries has emerged as a priority, but current injury prevention programs suffer from several problems, such as noncompliance and limited reductions in injury risk, and thus fail to adequately address the rising rates of ACL injuries.

A long-term goal is to reduce injuries due to movement deficits and restore the debilitating sequelae associated with prior injury or disease. Experience supports that there is a potential to reduce and repair aberrant biomechanics via regimented (i.e., non-targeted) neuromuscular training combined with subjective, delayed (i.e., delivered after the movement or exercise) verbal feedback. More particularly, experience indicates that objective, real-time, individualized (i.e., targeted), analytic-driven biofeedback improves on previous methods by inducing immediate neuromuscular adaptations that transfer across tasks. The system and method of the present disclosure supports the central tenant that sensorimotor biofeedback will improve localized joint mechanics and reduce global injury risk in evidence-based measures collected in laboratory tasks and in realistic, sport-specific virtual reality scenarios. The overall objective of this present disclosure is to implement and test innovative augmented neuromuscular training (aNMT) techniques to enhance sensorimotor learning and more effectively reduce movement deficits including, for example, biomechanical risk factors for ACL injury. Such aNMT biofeedback illustratively integrates biomechanical screening with a user display of real-time feedback. The feedback maps complex biomechanical variables onto simple visual stimuli that participants intuitively "control" via their own movements. The rationale is that effective biofeedback will improve the potential to decelerate injury rates.

An objective of the system of the present disclosure is to determine the efficacy of aNMT biofeedback to improve movement deficits associated with realistic tasks of daily living and human performance. More particularly, an objective of the illustrative system including aNMT (neuromuscular training+targeted, real-time biofeedback) is to yield a greater response as assessed through enhanced adaptation relative to a sham cohort (neuromuscular training exercises but with sham biofeedback).

A further objective of the system of the present disclosure is to demonstrate the efficacy of aNMT biofeedback to improve transfer of biomechanical adaptations to realistic human movement with actions performed in fully immersive virtual reality. More particularly, an objective of the illustrative system is to aim tests for improved mechanics during realistic, sport-specific actions performed in high-fidelity, free-ambulatory, immersive virtual environments. A further objective is to demonstrate that aNMT biofeedback produces greater transfer of improved mechanics in realistic immersive virtual reality scenarios compared to sham biofeedback.

Additional features and advantages of the present invention will become apparent to those skilled in the art upon consideration of the following detailed description of the illustrative embodiment exemplifying the best mode of carrying out the invention as presently perceived.

SUMMARY OF THE DISCLOSURE

The present disclosure relates to a real-time feedback system and method that targets and improves the movement biomechanics associated with desirable movement techniques and human performance. The real-time feedback system of the present disclosure is configured to overcome problems associated with prior injury prevention programs by utilizing objective feedback that: (1) can be provided largely independent of an expert's (e.g., a physical therapist) presence and active involvement with individual athletes, (2) is interactive and personalized which may enhance athlete motivation and compliance, (3) may improve learning and performance by directing athletes' attentional focus to an external source, and (4) engages implicit motor learning strategies that may result in faster learning and improved transfer.

The illustrative real-time visual feedback system of the present disclosure is designed so that objective information about multiple biomechanical variables related to ACL injury risk can be displayed concurrently in real-time to participants. These biomechanical variables are illustratively an assortment of kinematic and kinetic variables, some which are determined through inverse dynamics, and may be known as related to injury risk. As these variables change dynamically throughout participant movements, the feedback display is updated relative to these movements and displayed to participants in real time. The display essentially uses the current values of the biomechanical variables and maps them to the display through a predetermined influence on a geometric stimulus shape and a set gain parameter that determines the magnitude of the influence of the biomechanical variable on the change in the shape. Participants receive this real-time feedback during the performance of simple exercise (e.g., bodyweight squats), with their instruction being to perform the squat in such a way as to make the stimulus shape as rectangular as possible. The system and method of the present disclosure includes not only pragmatic advantages such as removing the need for detailed feedback from an expert, but the feedback design and presentation is based on fundamental theoretical principles in perception-action that may be promising for injury prevention, human performance and rehabilitation interventions.

The illustrative aNMT system and method of the present disclosure takes advantage of well-studied linkages between sensory perception and motor control to enable athletes to achieve complex movements by "controlling" the shape of a feedback stimulus. aNMT biofeedback is created by calculating kinematic and kinetic data in real-time from the athlete's own movements. These values determine real-time transformations of the stimulus shape the participant views via a user interface during movement performance. The participant's task is to move so as to create ("animate") a particular stimulus shape that corresponds to desired values of the biomechanical parameters targeted by the intervention. Further, the illustrative aNMT system and method is a self-guided, self-organized process; it is not explicitly coached and the sensorimotor adaptations are learned implicitly. Additionally, the illustrative aNMT system and method automates the delivery of targeted and analytic-driven biofeedback. This will remove reliance on specific injury prevention and biomechanical specialists to support feedback delivery. The cumulative advancements are expected to significantly enhance the effectiveness and efficiency of current injury prevention approaches.

Based on principles of motor learning, aNMT biofeedback is expected to improve retention and transfer of desired adaptations to injury prevention adaptations to realistic human performance and activities of daily living.

The illustrative aNMT system and method is significant, innovative and represents a new and substantive departure from the status quo through the introduction of real-time, analytic-driven, personalized, visual biofeedback optimized for neuromuscular training. By targeting the underlying sources of maladaptive movement strategies with prophylactic biofeedback interventions during the periods when biomechanical deficits evolve, it is expected to improve movement and/or reduce the occurrence of bodily injuries. The illustrative aNMT system and method illustratively utilizes rapidly processed visual feedback and effective implementation strategies, based on individualized movement deficit biomechanical profiles. The logical connection of individualized movement deficits with the most beneficial intervention will optimize injury prevention and rehabilitation strategies of the future. The use of scientifically validated, objective biofeedback positions us to make a large impact on sport injury prevention training and rehabilitation for all movement disorders, and has utility for preventive strategies related to other common injuries. Beyond the benefits of immediate reduction in health care costs, reduced injuries and better rehabilitation would promote continued health benefits achieved through active lifestyles and avoid subsequent complications of osteoarthritis in all ages and populations.

According to an illustrative embodiment of the present disclosure, an augmented neuromuscular training system for providing real-time feedback to a participant performing exercises includes a biomechanical acquisition system, and a motion analysis and feedback system in communication with the biomechanical acquisition system. The biomechanical acquisition system is configured to track movement of the participant and generate a biomechanical data structure including position data indicative of the movement of the participant. The motion analysis and feedback system includes a controller configured to receive the biomechanical data structure from the biomechanical acquisition system. The controller includes an exercise processing sequence for generating a stimulus data structure in response to the biomechanical data structure. A user interface is in communication with the motion analysis and feedback system and includes a display visible to the participant. This display includes a goal reference and a graphical stimulus having a boundary that is defined by the plurality of stimulus coordinate points. The plurality of stimulus coordinate points are defined by the stimulus data structure.

According to another illustrative embodiment of the present disclosure, a motion analysis and feedback system is in communication with the biomechanical acquisition system, and includes a controller configured to receive a biomechanical data structure from the biomechanical acquisition system. The controller includes an exercise processing sequence for generating a stimulus data structure in response to the biomechanical data structure, and for defining a plurality of stimulus coordinate points. A user interface is in communication with the controller and includes a display visible to the participant, the display including a goal reference and a graphical stimulus having a boundary that is defined by the plurality of stimulus coordinate points.

According to another illustrative embodiment of the present disclosure, a user interface for use with a motion analysis and feedback system includes a display visible to the participant, the display including a goal reference and a graphical stimulus having a boundary that is defined by at least six stimulus coordinate points. A stimulus data structure includes a plurality of biomechanical variables identified as injury risk factors and/or aberrant movement strategies. The graphical stimulus is a rectangle in an initial configuration. The relative positions of at least one of the stimulus coordinate points is configured to vary relative to the goal reference in response to the biomechanical variables, such that a size and the shape of the graphic stimulus varies in response to the biomechanical variables.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures, in which:

FIG. 3 is a perspective view of a participant wearing representative markers and user interface of FIG. 1;

FIG. 4 is a partial participant view through the representative user interface of FIG. 3;

FIG. 13 is a table of representative function modules of the motion analysis and feedback system of FIG. 1;

FIG. 14 is a table of illustrative function calls executed by the motion analysis and feedback system of FIG. 1;

FIG. 15 is a table of illustrative data structures of the motion analysis and feedback system of FIG. 1;

DETAILED DESCRIPTION OF THE DRAWINGS

Figure 1:
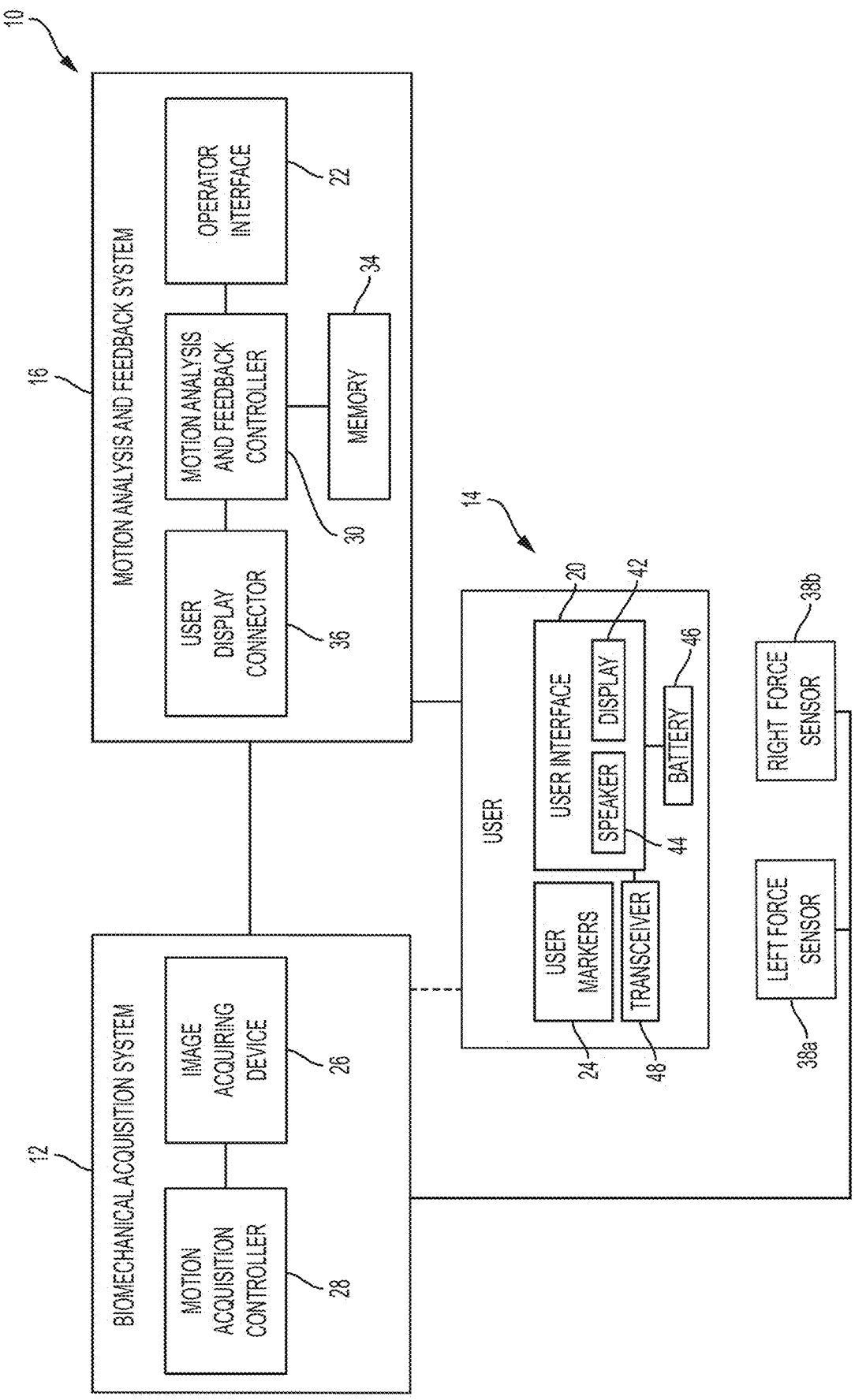
FIG. 1 is a block diagram of an illustrative augmented neuromuscular training system of the present disclosure.

For the purposes of promoting an understanding of the principles of the present disclosure, reference will now be made to the embodiments illustrated in the drawings, which are described herein. The embodiments disclosed herein are not intended to be exhaustive or to limit the invention to the precise form disclosed. Rather, the embodiments are chosen and described so that others skilled in the art may utilize their teachings. Therefore, no limitation of the scope of the claimed invention is thereby intended. The present invention includes any alterations and further modifications of the illustrated devices and described methods and further applications of principles in the invention which would normally occur to one skilled in the art to which the invention relates.

Augmented Neuromuscular Training System

With initial reference to FIG. 1, an illustrative augmented neuromuscular training system 10 of the present disclosure is configured to provide real time visual feedback to a participant. More particularly, the training system 10 is illustratively configured to provide a method for modifying movement deficits associated with injury risk, prior injury or disease pathology, such as modifying risk factors for anterior cruciate ligament (ACL) injuries in athletes, through real-time visual feedback of biomechanical data.

Illustratively, the augmented neuromuscular training system 10 includes a biomechanical acquisition system 12 configured to receive a biomechanical data from a user or participant 14, and in communication with a motion analysis and feedback system 16. As further detailed herein, the motion analysis and feedback system 16 receives signals representative of motion of the user 14 and provides real-time visual feedback to the user 14 in the form of a stimulus 18 on a user interface 20. As further detailed herein, the stimulus 18 may be simultaneously displayed on an operator interface 22.

The biomechanical acquisition system 12 illustratively comprises a motion analysis system including a plurality of user markers 24 worn by the participant 14 and configured to be detected by an image acquiring device 26. A motion acquisition controller 28 receives the relative positions of the markers 24 as detected by the image acquiring device 26, and is configured to generate a biomechanical data structure (e.g., a three dimensional (3D) model) based upon such position data.

The motion acquisition controller 28 is illustratively operably coupled with a motion analysis and feedback controller 30. The motion analysis and feedback controller 30 is in communication with a memory 34 and illustratively includes a microprocessor configured to executed machine readable instructions stored in the memory 34. A user display connector 36, illustratively a wireless transceiver, provides communication between the motion analysis and feedback controller 30 and the motion acquisition controller 28.

Figure 2:
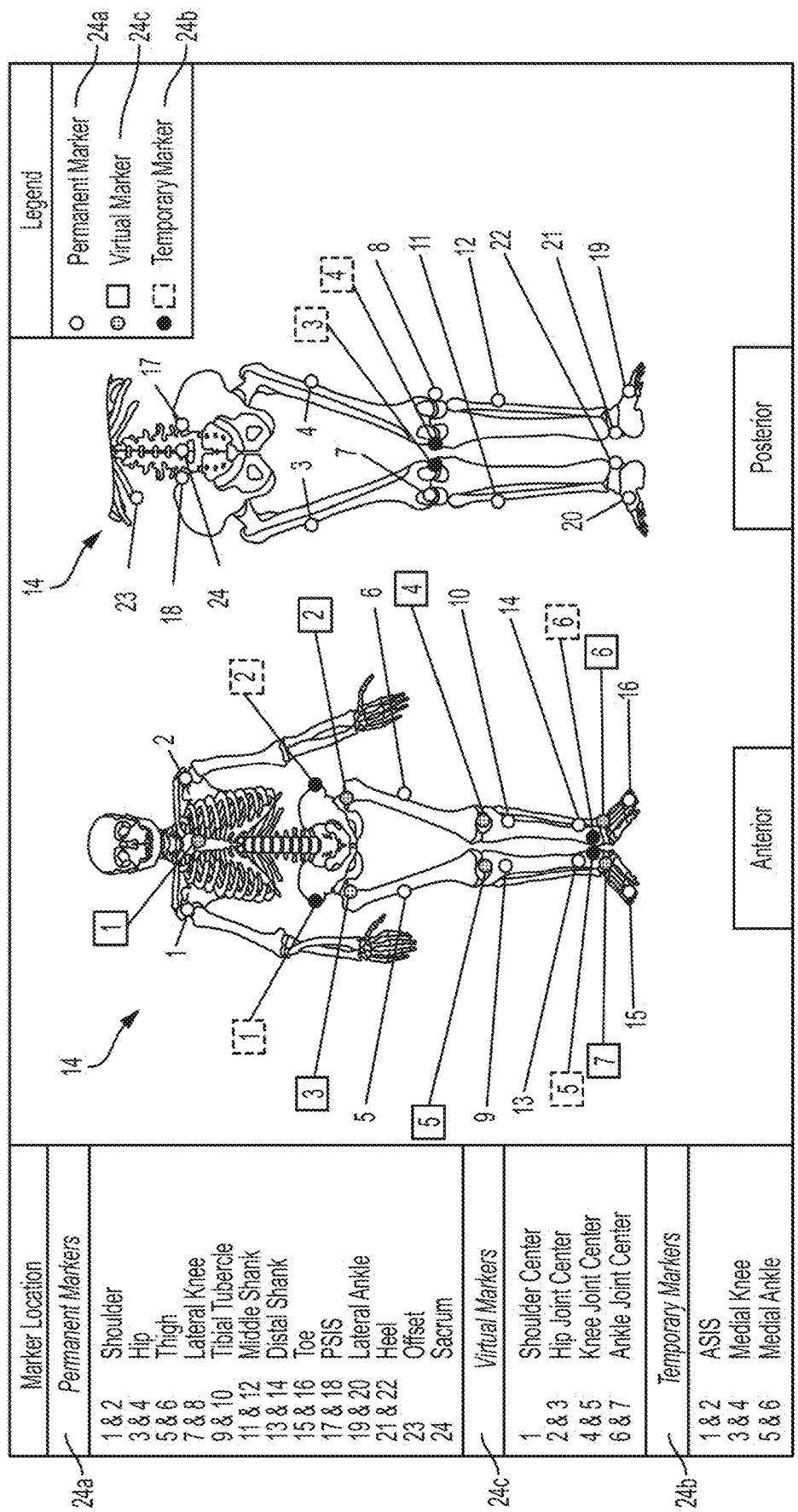
FIG. 2 is view of representative markers for tracking participants' movements by the illustrative biomechanical acquisition system of FIG. 1.

The illustrative visual feedback stimulus 18 may be constructed and presented to participants in real time using an assortment of hardware and software (see FIGS. 1 and 2). Illustratively, the thirty reflective markers 22 were supported on, or worn by, each participant 14. The image acquisition device 24 illustratively comprises a multi-camera Raptor-E motion capture system (available from Motion Analysis Corp. of Santa Rosa, Calif.). Each cameral illustratively includes a flash or strobe that emits light to reflect off of the markers 22. It should be appreciated that the type of image acquisition device 24 may vary, including video cameras that do not require markers 22 to be worn by the participant 14. Additionally, the number and placement of cameras may vary.

With reference to FIGS. 2 and 3, illustrative markers 24 may consist of a variety of permanent markers 24a, temporary markers 22b and virtual markers 22c. Permanent markers 22a are fixed to the participant 14 during the duration of the exercise. Temporary markers 22b are removed from the participant 14 before the end of the exercise. An illustrative procedure for generating the biomechanical data structure includes constructing a biomechanical model consisting of a static motion capture lasting approximately 1 second, during which specific landmarks on the body were identified by placement of the permanent and temporary markers 24a and 24b (see FIG. 2). The landmarks, when paired with permanent markers 24a that remained on the body during the squat movement, were used to create virtual markers 24c through simple geometrical offsets performed in the Cortex 5.3 program (Motion Analysis Corp., Santa Rosa, Calif.). The virtual markers 24c may replace markers 24 that were frequently occluded during participant movements. During the squat motion for example, the torsos of participants may occlude the two anterior superior iliac spine (ASIS) markers 24 required for calculating the hip joint centers. Using the location of the posterior superior iliac spine (PSIS) markers 24 (which were very rarely occluded) and the biomechanical model, the program was able to interpolate the position of the ASIS markers, and subsequently, the centers of the hip joints. This process increases the quality and robustness of the real-time feedback, as this illustratively permits the feedback to be updated at a rate of 20 Hz (every 50 ms) without any detectable problems in the responsiveness of the display relative to participant movement.

The biomechanical acquisition system 12 illustratively further includes left and right load or force sensors 38a and 38b. Illustratively, the force sensors 28a and 28b comprise two embedded BP600900 force platforms (available from AMTI of Watertown, Mas.) to collect separate ground reaction forces from each foot of the participant 14. The data recorded by the sensors 28a and 28b may be integrated and synchronized via Cortex (available from Motion Analysis Corp. of Santa Rosa, Calif.). The synchronized data (i.e., biomechanical data structure) is then relayed to the motion analysis and feedback system 16 for generating the visual feedback or stimulus 18 on the user interface 20. An illustrative program used to generate the visual feedback display, including stimulus 18, is a custom-written C++ program designed in Microsoft Visual Studio Professional 2015 (Microsoft Corp., Redmond, Wash.) and incorporating OpenGL (Khronos Group, Beaverton, Oreg.) as the graphics application interface. This program, as further detailed herein, is stored in memory 34 and is responsible for importing the live data stream from the Cortex SDK and exporting the finished visual display on the user interface 20 to participants 14.

The user interface 20 illustratively includes goggles or glasses 40 including a visor or display screen 42 configured to be supported on the head the participant 14 and provide visible instructions or feedback to the participant 14 (including the stimulus 18). A speaker 44 may also be supported by the googles 40 to provide audible feedback to the participant 14. The user interface 20 further illustratively includes a battery 46 configured to supply power to the display 42 and the speaker 44. A transceiver 48 is illustratively supported by the user interface 20 and is configured to provide wireless communication between the user interface 14 and the user display connector 36, and thereby the motion analysis and feedback controller 30, of the motion analysis and feedback system 16. One illustrative user interface 20 may be Holo-Lens, mixed reality smartglasses available from Microsoft of Redman, Wash. While the illustrative user interface 20 is shown being worn by the participant 14, it should be appreciated that other types of displays may be utilized, including a TV screen, a projector screen, a monitor, a smart phone, a tablet, a laptop screen, a virtual reality headset, an augmented reality headset, etc.

Visual Feedback Stimulus

Figure 5A:
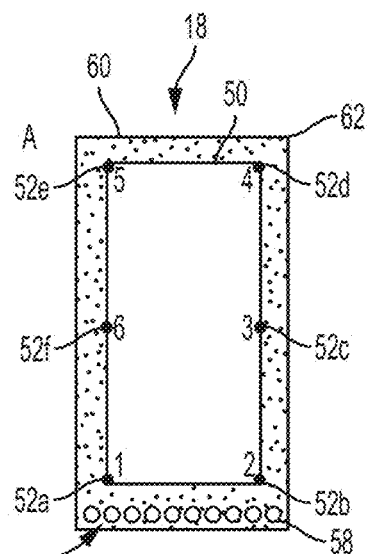
FIGS. 5A-5F are views of representative stimulus outputs displayed on the user interfaces in the system of FIG. 1.

With reference to FIGS. 5A-5F, the illustrative real-time visual feedback display or stimulus 18 is shown in the form of a geometric shape, illustratively a boundary 50 in the form of a rectangle defined by six stimulus coordinate points (50a-50f) when the stimulus is in an initial or default configuration (FIG. 5A). The coordinates of the points 50 are illustratively defined as a function of kinematic and kinetic variables identified as ACL-injury risk factors. The biomechanical variables illustratively may include trunk lean, knee-to-hip moment ratio (KHIVIr), knee abduction moment (KAM), and vertical ground reaction force (vGRF) ratio. Each variable has a specific effect on the feedback display or stimulus 18. The task of the participant 14 is to keep the shape of the boundary 50 as close to a rectangle as possible. A reference goal 54 is also illustratively provided on the display to provide a reference for the participant and aid her in maintaining the rectangular shape of the stimulus 18. More particularly, an outline of the shape's corners as defined by coordinate points one, two, four, and five (52a, 52b, 52d, and 52e) remain while participants perform the exercise and are shown as the reference goal 54 in FIGS. 5B-5F.

During the start of an exercise, the stimulus 18 is in an initial or default configuration. Illustratively, the stimulus 18 in this initial configuration has the shape of a rectangle. This shape is depicted in FIG. 5A and is illustratively defined by stimulus coordinate points one through six (52a-52f). It should be appreciated that more or fewer stimulus coordinate points 52 may be used based upon the desired feedback and resolution thereof.

The display 42 also illustratively also includes a count or repetition (rep) indicator 56. The rep indicator 56 illustratively includes a plurality (e.g., ten) of grey circles 58 towards the bottom of the stimulus 18. The circles 58 are used for counting the number of exercises (e.g., squats) within a block or set. As participants performed each exercise (e.g., squat), the circles 58 change appearance (e.g., from grey to green).

Figure 5B:
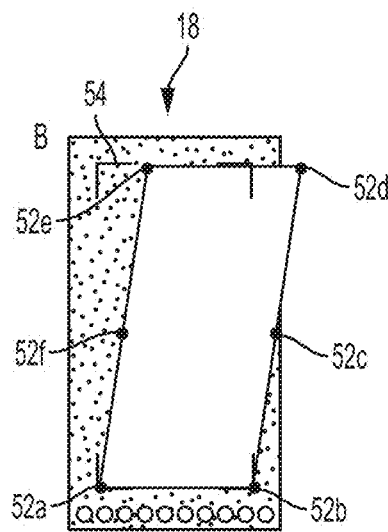
Figure 5C:
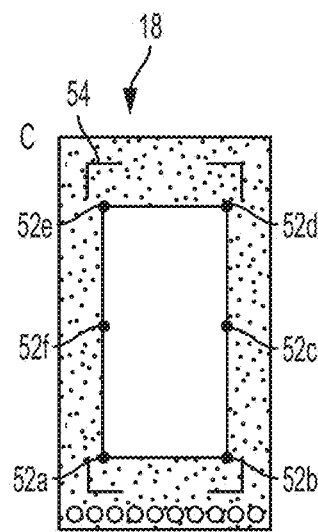
Figure 5D:
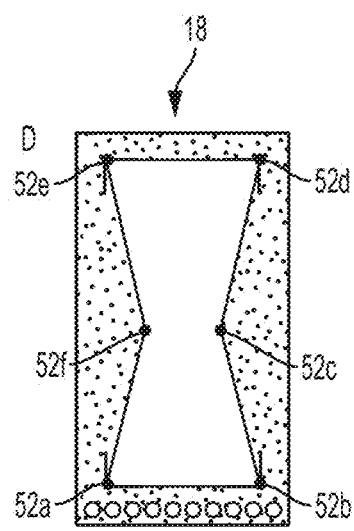
Figure 5E:
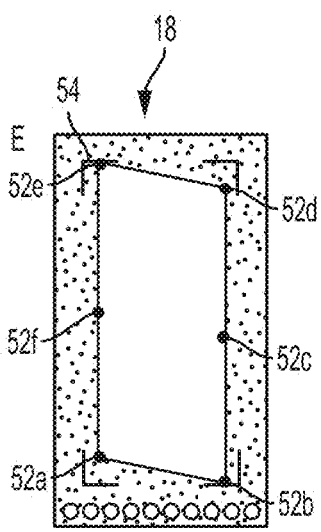
Figure 5F:
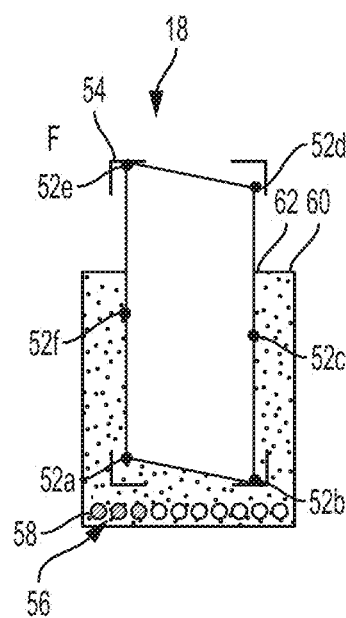

A height indicator 60 may also be shown on the display 42 in cooperation with the stimulus 18. The height indicator 60 may be a background rectangle including an upper edge 62 that may be raised and lowered as the biometric data structure process by the motion analysis and feedback system 16 indicates that the participant is lowering her body. Depicted in FIGS. 5B-5E are the illustrative effects of the trunk lean, KHMr, KAM, and vGRF variables, respectively. In FIG. 5F, the upper edge 62 of the lighter background rectangle or height indicator 60 is shown lowered from its maximum height (displayed in FIGS. 5A-5E) as a participant 14 performs the downward movement of a squat exercise. Accordingly, the upper edge 62 of the height indicator 60 will move upward as the participant 14 begins to rise back up.

Trunk lean is illustratively defined as the angle of deviation from the midline of the body. Changes in trunk lean cause the stimulus 18 to lean to the respective side (FIG. 5B). The KHMr variable is illustratively defined as the ratio of the knee inverse dynamics moment to the hip inverse dynamics moment. Ratios with values larger than 1 (i.e., knee moment>hip moment) resulted in the stimulus increasing in overall size (the desired outcome). The opposite was true for ratios smaller than 1—the stimulus 18 decreased in overall size (see FIG. 5C). The overall value of the KHMr variable was determined by averaging the KHMr value of the right and left sides of the body. The KAM variable was defined as the knee inverse dynamics moment and would cause the stimulus to pinch in the middle when there was excessive valgus and to expand in the middle when there was excessive varus (see FIG. 5D); however, the stimulus 18 displayed a greater sensitivity to the knee moments with excessive valgus, as it has been shown to be a greater risk factor than excessive varus. Unlike the averaged effect of the KHMr variable, the KAM value of each knee separately affected their corresponding side of the stimulus. The vGRF ratio variable was defined as the ratio of the amount of force measured by the left and right force platforms in the vertical directions. A greater force magnitude measured by either platform caused the respective bottom and top corners to lower while the corners on the side with a lower force magnitude rose proportionally (see FIG. 5F).

In addition to the previously described variables, the number of exercises (e.g., squats) performed by a participant may be tracked by a variable measuring the knee flexion-extension. For example, a squat may be considered complete when a participant 14 achieves a knee angle below 90° during the squat and then returns to the original standing position (see FIG. 5F). This variable may be visually displayed to participants (separately from the rectangular feedback stimulus 18) through the movement of a lighter-colored rectangle 60 behind the primary feedback display shape 50. As a participant 14 squats into a lower position, the height of the background rectangle 60 decreases. Upon completing a squat, the counter 56 was incremented by changing the color of a successive circle 58 on the display 42. A target line for participants' knee angles may also be displayed at the bottom of the background rectangle 60.

Real-Time Biofeedback Trials

An exemplary study was conducted to determine the effectiveness of a real-time biofeedback stimulus 18 that maps to a comprehensive movement profile for reducing biomechanics related to ACL injury risk. The stimulus 18 maps on to a wider range of biomechanical variables (e.g., knee, trunk, hip, etc.) than previous biofeedback investigations (e.g., knee only). To compare real-time biofeedback to traditional interventions, a novel sham feedback apparatus was designed to limit the amount of useful feedback information available to participants during training of squat movements. It was hypothesized that participants would elicit significantly greater squatting performance, as indexed through a novel heat map analysis, throughout acquisition and during retention (mid and post testing) when using real-time biofeedback compared to the sham feedback stimulus. This heat map system can be used to provide participant with a movement score for each of the exercises. In this example, the area that is not captured with desired movement over the period of exercise would be deducted from a referenced perfect score and provide an objective assessment of the movement quality for particular set of exercise. This information would be following a movement training session with the aNMT system 10.

Twenty participants were recruited to participate in the exemplary study (M age=19.7±1.34 yrs; M height=1.74±0.09 m; M weight=72.16±12.45 kg). All participants were female collegiate athletes Participants had no history of neurological disorders (including any neuromuscular disabilities), musculoskeletal disabilities or disorders, or balance problems. Participants were free of any injuries within the last five years that impaired movement or the ability to stand.

The provided example of real-time feedback display used in the study was designed so that objective information about multiple kinematic and kinetic variables related to ACL injury risk could be displayed concurrently and in real time to participants. The stimulus was designed specifically to map onto a wider range of biomechanical variables (e.g., knee, trunk, hip, etc.) than previous biofeedback investigations that were isolated to a single variable (e.g., knee only). The shape of the display was a simple, two-dimensional rectangle defined by six points (see FIG. 5A). The vertical and horizontal coordinates of these points were defined as a function of four kinematic and kinetic variables previously identified as ACL-injury risk factors, each having a unique effect on the feedback display (see FIGS. 5B-5E): (1) lateral trunk flexion, (2) knee-to-hip joint moment of force ratio (KHIVIr), (3) knee abduction moment of force (KAM), and (4) vertical ground reaction force ratio (vGRF). The current values of the biomechanical variables were mapped via the geometric shaped stimulus 18 of the display (i.e., a rectangle), and as these variables changed dynamically throughout the participants' movements, the feedback display was updated relative to these changes and displayed to the participants in real time. The feedback shape of the stimulus 18 was thus not only changing in real-time but was interactive in that it responded immediately and reliably to participants' movements.

Table 1 below summarizes each variable's definition, optimal value, and effect on the stimulus 18:

TABLE 1

Description of the biomechanical variables and their effects on the feedback stimulus

| Variable | Acronym | Definition | Effect on Stimulus | Goal Values |
|---|---|---|---|---|
| Lateral Trunk Flexion | — | The angular deviation of the trunk in the frontal plane from the midline of the body | The stimulus "leans" to the respective side | 0° |
| Knee-to-Hip Joint Moment of Force | KHMr | The ratio of the internal knee extensor joint moment of force to the internal hip extensor joint moment | The stimulus decreases in size for ratios larger than 1 and increases for ratios smaller than 1 | 1 |
| Knee Abduction Moment of Force | KAM | The external knee abduction joint moment of force | The stimulus "pinches" in the middle as the moment increase and expands when it decreases | 0N |
| Vertical Ground Reaction Force Ratio | vGRF | The ratio of the amount of force measured by the left and right force platforms in the vertical directions | Imbalances in force cause the stimulus to lower and raise the appropriate corresponding sides | 1 |

TABLE 1-continued

Description of the biomechanical variables and their effects on the feedback stimulus

| Variable | Acronym | Definition | Effect on Stimulus | Goal Values |
|---|---|---|---|---|

The participants 14 in the study were instructed to squat so as to keep the stimulus shape as close to a perfect, symmetrical rectangle as possible. This was achieved by moving so as to produce optimum values (i.e., values associated with low ACL injury risk) of the aforementioned variables, but participants were not told that and the biomechanical variables and their optimum values were not explained to them. As the values of the variables neared or fell within optimum ranges specific to the given variable(s), a more symmetric rectangle was obtained; alternatively, the rectangle became systematically distorted by increasing amounts as the values of the variables deviated from the optimum values.

The number of squats performed by the participant 14 was tracked by a variable measuring knee flexion angle. A squat was considered "complete" when a participant 14 achieved a knee flexion angle below 90° during the squat and then returned to the original standing position (see FIG. 5F). This variable was visually displayed to participants (separately from the feedback rectangle just described) through the movement of a lighter-colored rectangle behind the primary feedback display shape. As a participant 14 squatted into a lower position, the height of the background rectangle decreased. Ten circles situated below the rectangle served as a counter representing the number of "completed" squats, which would change colors from grey to green once participants had completed a full squat motion (i.e., participants were standing upright after performing the squat).

Figure 6A:
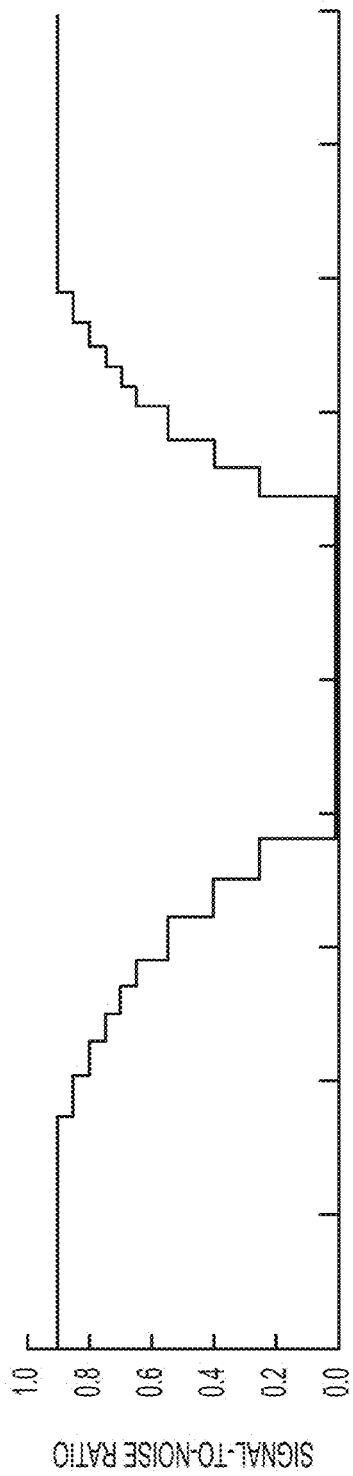
FIGS. 6A and 6B are plots of illustrative output used to derive sham feedback.
Figure 6B:
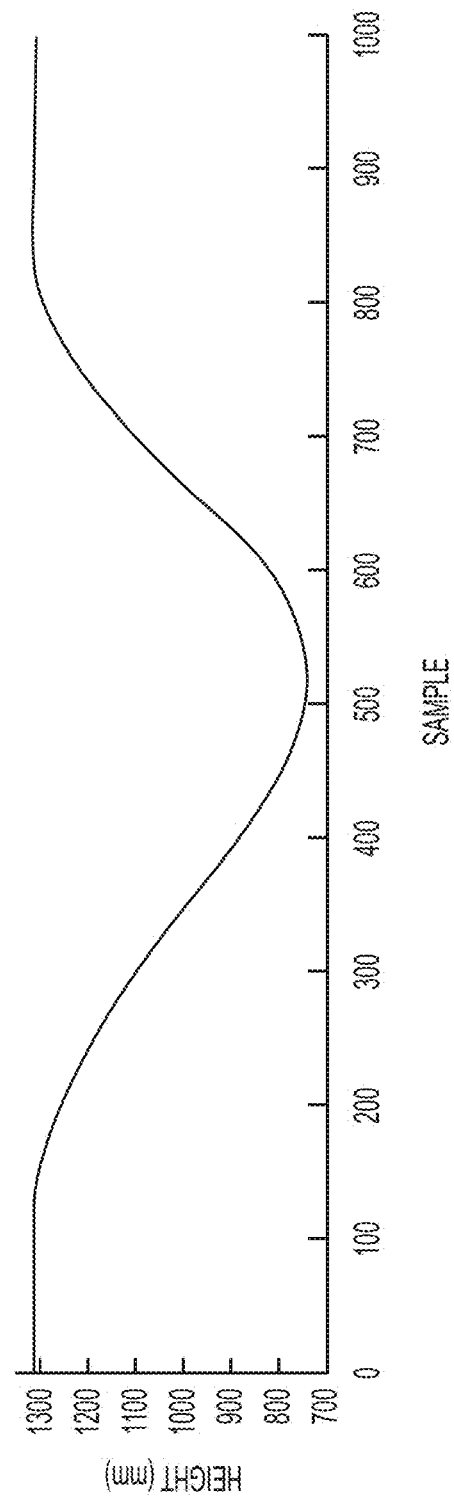

In addition to the real-time feedback display just described, a feedback display was also developed for the sham condition. The real-time and sham feedback displays presented identical stimulus shapes that responded, at least in part, to the same biomechanical parameters. However, the sham feedback was designed to limit the amount of useful feedback information available to participants during the squat movements. This was accomplished using a stepwise gain manipulation (FIGS. 6A and 6B). Movements not critical to the targeted biomechanical parameters during a squat (i.e., movements occurring close to the start/end points of squat movements) caused the sham display to respond nearly equivalently to participant movement (and thus nearly equivalently to the real feedback condition), but the influence of the biomechanical variables on the stimulus shape during the important phases of the squats were progressively eliminated from the stimulus, such that at the bottom of the squat movement the sham feedback stimulus deviated from the goal shape as a function of random noise, not from the movements of participants (i.e., it provided little to no actual feedback). This specific type of sham feedback was utilized to facilitate similar phenomenological responses to that of the experimental stimulus without promoting movement directly associated with reduced ACL injury risk.

FIGS. 6A and 6B display the technique used to derive the sham feedback. The bottom plot (FIG. 6B) is a sample time series of a single squat rep performed during a sham trial. Specifically, the mid-shoulder marker 24 is illustrated. The top plot (FIG. 6A) depicts how the signal-to-noise ratio (i.e., how much of the stimulus movement was driven by participant movement or noise) corresponds to a particular movement stage of a squat.

Figure 7A:
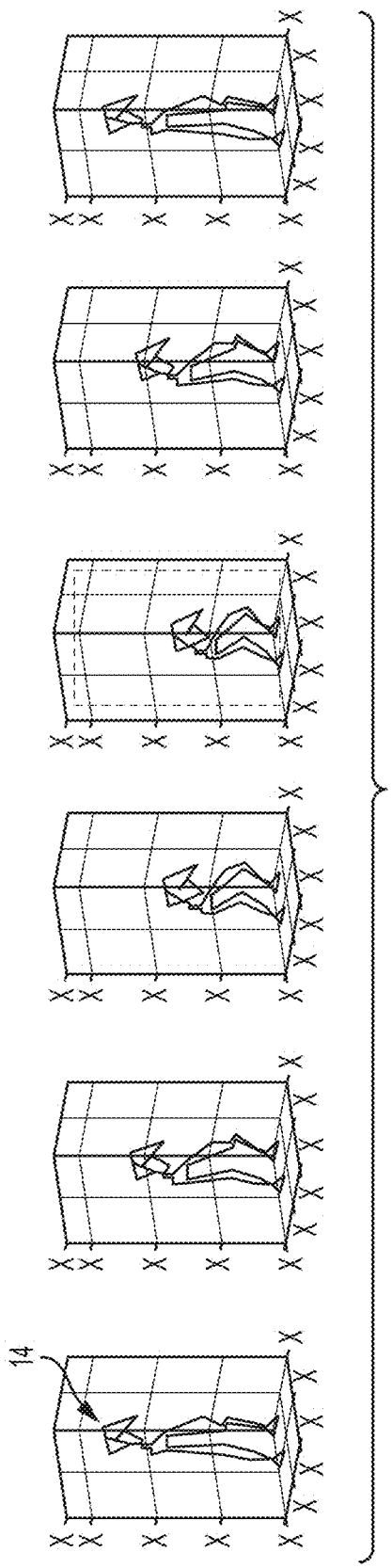
FIG. 7A is a representation of different body positions of a participant during an illustrative squat exercise.

FIG. 7A illustrates a participant 14 performing a single rep of a squat exercise. Shape of the aNMT stimulus 18 corresponds to performance of the repeated squat (stimulus 18 of FIG. 4 corresponds to the fourth skeleton panel of FIG. 7A). Analytic feedback represents undesirable slight lateral trunk flexion, knee valgus and GRF asymmetry (right leg bearing more weight). The feedback is presented as if viewing from behind to avoid the need for mirror-image cognitive processing of the movement.

Participants' movements were recorded using the image acquiring device 26 as detailed above, illustratively a 10-camera motion capture system (Raptor-E, Motion Analysis Corp., Santa Rosa, Calif.) sampling at 240 Hz. In conjunction with the motion capture system, two force sensors 38 as detailed above (embedded force platforms 38 (BP600900, AMTI, Watertown, Mass.) sampling at 1200 Hz) were used to collect ground reaction force from each foot from the participant 14 and were synchronized with the motion system 26. The synchronized marker trajectory and force data were accessed via a custom software program including machine readable instructions stored in memory 34 and executed by controller 30 that was designed to calculate and map the above variables to generate the visual feedback display or stimulus 18.

The visual display 42 was wirelessly transmitted from a desktop computer to participants using an ARIES Pro Wireless HDMI Transmitter and Receiver 36 (Nyrius, Niagara Falls, ON, Canada). The ARIES Pro is capable of transmitting uncompressed 1080 p signals up to 160 feet with a latency of <1 ms, which allowed for maximum mobility of participants without degradation of feedback quality. Participants viewed the real-time feedback through a pair of video eyewear glasses 40 (Wrap 1200 DX-VR; Vuzix Corp., Rochester, N.Y.), which had a 60 Hz screen refresh rate (a new frame appeared approximately every 16.67 ms). The glasses 40 presented the feedback display or stimulus 18 in a fixed position relative to the participants' eyes and encompassed their entire field of view. Both the ARIES Pro and glasses 40 were powered by a portable battery pack 46 (PowerGen Mobile Juice Pack 12000; PowerGen, Kwai Chung, Hong Kong, PRC). The wireless transmitter 48 and battery pack 46 were stored in a modified hydration pack designed for running (CamelBak Products, LLC, Petaluma, Calif.). The backpack provided minimal interference to natural movement as it held the equipment securely against the body and was relatively small (length×width×height: 33 cm×27 cm×7.6 cm).

In order to compare the effects of the real-time and sham feedback displays, an AB/BA or two-treatment crossover design was utilized. As the name implies, half of the participants received one condition first (e.g., 'A') and another condition second (e.g., 'B'), while the other half of participants received the two identical conditions but in the opposite order. We randomly assigned participants to one of two groups: real-time biofeedback first (i.e., 'A') or sham feedback first (i.e., 'B'). First, participants completed a block of 10 squats without any feedback (pre-test). Then, participants completed four blocks of 10 squats using their assigned condition (i.e., real-time biofeedback or sham) (acquisition phase 1). Before switching to the next feedback type, a block with no feedback was administered (mid retention test) followed by four blocks of 10 squats using the opposite feedback type as used in acquisition phase 1 (acquisition phase 2). Finally, participants completed a block of 10 squats without any feedback (post retention test). In total, each participant completed 110 squats-40 training squats for each feedback type (80 total) and 10 squats during each test period (30 total; see FIG. 2). Participants were permitted breaks between blocks as necessary.

Each participant 14 was outfitted with 30 retroreflective markers 24, with a minimum of three tracking markers 24 on each segment, and the backpack containing the wireless transmitter and battery pack. Markers were placed on the sacrum between the L5 and S1 vertebrae, and bilaterally on the acromio-clavicular joint, anterior superior iliac spine, posterior superior iliac spine, greater trochanter, mid-thigh, medial and lateral femoral condyles, tibial tubercle, lateral and distal aspects of the shank, and medial and lateral malleoli, the heel, and central forefoot (between the second and third metatarsals). After the initial experimental preparation, all participants 14 received identical instructions about the squat exercise. The instructions were purposefully kept very basic as to allow for implicit discovery of how their movements related to the stimulus shape during the squat exercise; they were told only to "maintain the goal stimulus shape and size as closely as possible" and, as a secondary instruction, "to squat to sufficient depth", as indicated by the depth indicator and circle counter at the bottom of the stimulus. Participants were also asked to keep their arms crossed in front of their chest and to avoid covering any markers. A set of squats was considered complete once all ten circles' colors changed from grey to green, indicating that ten sufficiently deep squats were performed. If participants were unable to intuitively achieve the appropriate depth, they were explicitly instructed that they must squat lower. This happened solely during the first feedback trial that participants experienced; no participants needed to be reminded again after the first trial. No other instructions were provided regarding the squats or the stimulus 18.

The recorded raw, three-dimensional marker positions, ground reaction forces, and center of pressure acquired from both feet were first exported from Cortex and imported into MATLAB for preprocessing. Preprocessing consisted of visual inspection of a virtual mid-shoulder marker (defined as the averaged position of the left and right shoulder markers) for each squat trial (pre-, mid-, and post-test and training trials). During the visual inspection, time series of the mid-shoulder marker's vertical position were plotted and trimmed. Only the portions of a trial where the participant was performing a squat were retained for analysis. All other marker and force data were trimmed according to the time points that were identified from the mid-shoulder marker. This procedure resulted in a time series for each squat rep across every squat set.

In order to quantify participants' ability to control the stimulus shape, heat map analysis was performed on the squat data during the middle four training sets and on "reconstructed" feedback shapes obtained from the raw position and force data in the pre- and post-test sets. The heat maps provided a global assessment of squatting performance by indicating how the movement patterns of the biomechanical variables associated with ACL injury related to the target feedback shape (i.e., a rectangle). Specifically, the heat maps portrayed the percentage of time a defined space was occupied by the feedback stimulus. The heat map analysis consisted of two steps: (1) the construction of the heat maps and (2) the calculation of each heat map's correctly occupied space. Heat maps were created using the MATLAB function inpolygon. The calculation of each heat map's correctly occupied space consisted of first calculating the proportion of occupied space within the goal stimulus and then calculating the proportion of occupied space outside of the goal shape. The proportion of occupied space outside of the goal shape was finally subtracted from the proportion of occupied space within the goal stimulus. The possible results of this operation range from −1.00 to 1.00. A score of −1.00 indicated that the stimulus never occupied a correct location in the display while always occupying an incorrect location. A score of 1.00 indicated a stimulus shape never deviated from the goal shape and size, which meant that the relevant biomechanical parameters were achieving the desired optimal values associated with lower injury risk. These scores are transformed and presented as percentages in the following sections for ease of interpretation with higher percentages indicating better squatting performance.

In order to test for varying levels of fatigue caused by differences in the number of squats performed by each participant group, the total number of squats performed by the real- and sham-first feedback groups were compared using an independent samples t-test. This step was necessary because participants required a few squat repetitions in order to explore and determine the appropriate squat depth, which may or may not have affected participants' fatigue level and subsequent squatting performance.

To assess squatting performance, each trial block was first averaged to produce a single heat map percentage score. Then, to assess differences in squatting performance during training (i.e., visual feedback present), separate 2 (condition)×4 (trial block [1, 2, 3, 4]) mixed ANOVAs with repeated measures on the last factor were conducted for acquisition phase 1 and acquisition phase 2. To assess learning (i.e., when visual feedback absent), a 2 (order)×3 (test phase; pre-test, mid-test, post-test) mixed ANOVA with repeated measure on the last factor was conducted. Bonferroni adjustments were used when appropriate and an alpha level of $p<0.05$ indicating significance was selected a priori.

Figure 7B:
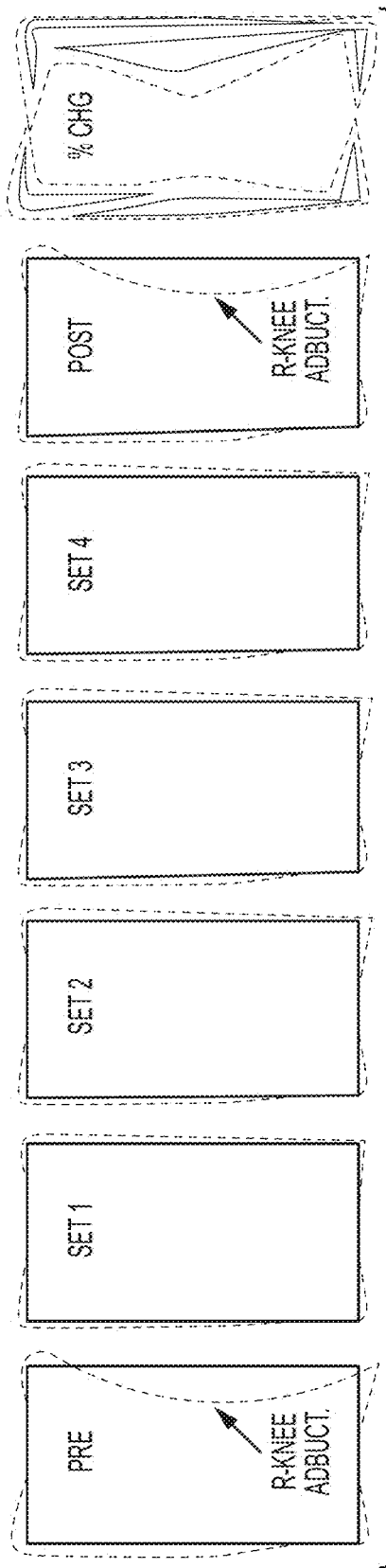
FIG. 7B is a representation of different heat maps showing movement patterns represented by stimulus shapes associated with the body positions of FIG. 7A.
Figure 9:
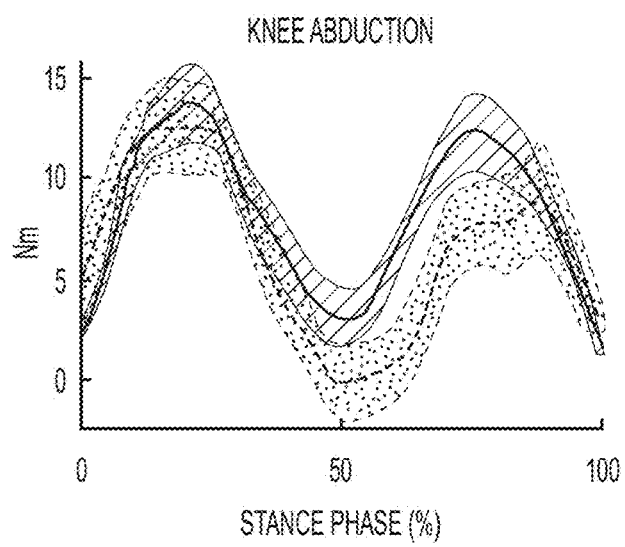
FIG. 9 is a representative output plot of knee abduction as a function of stance.

FIG. 7B are heat maps showing the movement patterns represented as aNMT stimulus shapes. Panels 1-6 (left to right) show proportion of time the feedback shape occupied an area of the total display (white=0, red=1) for a representative subject. Panels 1 & 6 depict the pre- and post-tests, respectively, when no feedback was provided. Panels 2-4 are the four training sets when feedback was provided. Panel 7 shows the group post-pre shape difference (7.7% overall; red=most change)—how and where aNMT improved squatting biomechanics. Trunk lean, VGRF asymmetry, and knee abduction moment improved prominently. The preliminary data using aNMT system 10 indicate an 8% group reduction in stimulus deficit mapping (FIG. 7A) and reduced knee frontal plane load (FIG. 9) can be achieved in a single aNMT session. Importantly, these preliminary data also show significant transfer to positive adaptations (increased knee flexion angle) during a power-based, dynamic jumping task.

Figure 8A:
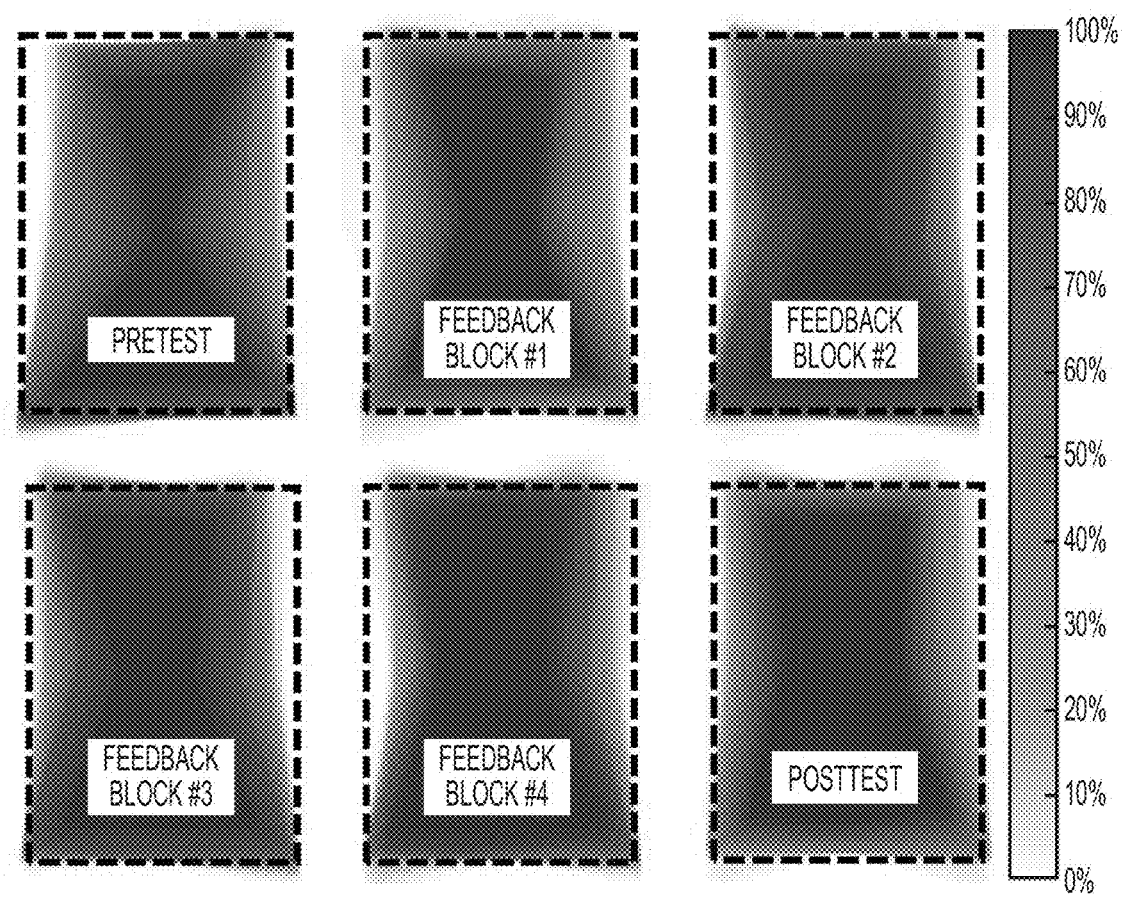
FIG. 8A is a heat map representing squatting performance during real-time biofeedback trials.
Figure 8B:
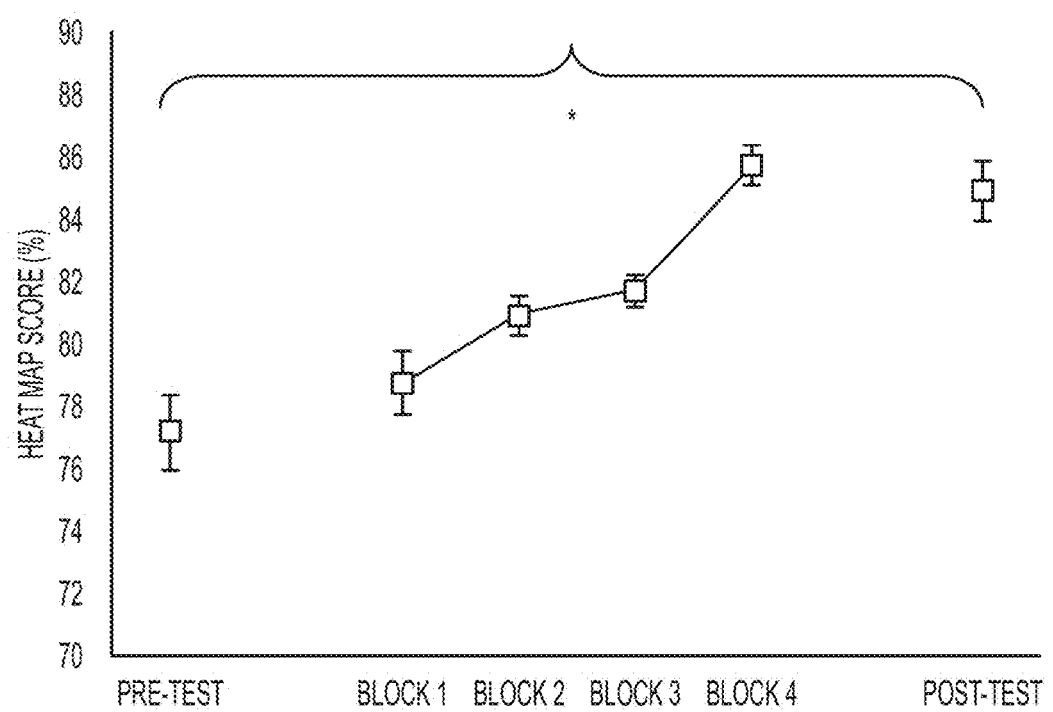
FIG. 8B is a graph showing the heat map scores from the heat map of FIG. 8A.

Heat map analyses have revealed that participants' mean improvement in the produced stimulus shape (i.e., more closely resembled the optimal shape) from the pre- to post-test blocks was 7.70%. This improvement was significant, $t(10)=6.63$, $p<0.01$, with scores rising from an average of 77.17% (SD=3.80%) in the pretest to an average of 84.87% (SD=3.12%) in the posttest. Additionally, participants demonstrated a trend of increasing heat map scores over the four feedback training blocks. Participants produced an average heat map score of 78.76% (SD=3.40%), 80.91% (SD=2.20%), 81.65% (SD=1.57%), and 85.71% (SD=2.11%) for feedback blocks one through four, respectively. See FIG. 8A for a single participant representative example of heat map analysis and FIG. 8B for representative group means.

There were no significant differences in the number of squats performed between the real-first feedback group (M=111.80, SD=7.15) and the sham-first feedback group (M=114.30, SD=5.76), t(18)=0.86, p=0.40. There were no significant differences in overall squatting performance as measured by the heat map percentage scores for condition or trial block, nor a condition×trial block interaction during acquisition phase 1 or phase 2 (all p>0.05). Thus, we averaged the heat map percentage scores across the eight trial blocks for each condition respectively and performed a paired-samples t-test to assess differences during training per feedback type. That test revealed that squatting performance during the real-time biofeedback trials (M=60.73%, SD=6.47%) was better than during the sham feedback trials (M=56.62%, SD=8.42%), t(19)=3.06, p=0.006. There were no significant differences in squatting performance for order or trial block, nor an order×trial block interaction during the three test phases that assessed learning. Thus, the availability of the interactive feedback shape during the squat training trials was beneficial to performance compared to when only the sham stimulus was available.

An objective of the illustrative study was to determine the effectiveness of a real-time biofeedback system compared to a sham feedback system for improving biomechanics related to ACL injury risk. Squatting performance, as measured through heat map analysis, was significantly better when participants interacted with the real-time biofeedback system compared to the sham. The study makes three distinct innovations. First, the illustrative system employed an interactive, real-time stimulus that implicitly guided performance while promoting an external focus of attention, factors which as noted previously have been identified as improving motor performance and learning. Second, the illustrative developed real time biofeedback system mapped multiple biomechanical variables associated with ACL injury risk onto a single stimulus. The illustrative system will be applicable for all similar feedback approaches that target aberrant movement deficits that are associated with other injury risk, prior injury and pathology. Unlike previous systems that are isolated to one factor such as knee abduction/adduction, the system uniquely presents participants with a global biomechanical profile associated with movement deficits and, in this case, ACL injury risk including lateral trunk flexion, knee-to-hip joint moment of force ratio, knee abduction moment of force, and vertical ground reaction force. Third, the inclusion of the sham feedback system demonstrated that any increased engagement or motivation associated with real-time biofeedback is not alone sufficient to improve performance, but an accurate mapping from kinematics and kinetics to the feedback is necessary for performance gains.

The results of this study suggest that ACL injury prevention, rehabilitation programs and human performance could be improved by integrating a real-time, interactive biofeedback stimulus that engages a control of external feedback methodology. Prevention programs could use this stimulus to improve performance of prophylactic exercises, which may lead to decreased ACL injury risk. Likewise, following an ACL injury, our approach may be particularly beneficial as a rehabilitation tool for those in the recovery stages. An external focus of attention has already demonstrated efficacy for those who have undergone ACL reconstruction (Gokeler et al., 2015) and our stimulus elicited a similar benefit without the need for an expert to deliver instruction. The integration of new factors associated with ACL injury risk suggests that it may also be possible to design similar real-time biofeedback systems to target other movement dysfunction. For example, previous investigations using real-time biofeedback for gait retraining may benefit by integrating further factors to supplement previously seen motor skill improvements.

The illustrative method of the present disclosure of delivering augmented feedback departs from traditional methods in that it can be delivered to subjects in real-time through the use of multiple integrated technologies. The force plate data and lower extremity joint position data generated from the 3D passive optical motion capture system are delivered to a central hub for integration. The data are processed via a custom pipeline to determine multi-planar/multi-dimensional biomechanical measures of interest and then telemetrically streamed to the smart-eye headset to optimize system interaction and negate latency between data input and visual display output. The desired outcome for participants to achieve while performing each of the intervention exercises is to move so as to produce a rectangular shape and make the shape as large as possible. This is achieved when each of the targeted biomechanical variables is at the desired value. Deviations of the variables from desired values result in specific and systematic changes to the feedback shape: 1) Lateral trunk flexion causes the object to lean to the respective side (FIG. 10A), 2) Inverse dynamics were used in this example to determine the hip to knee sagittal plane moment ratio; reduced relative hip moment contributions shrink the shape and larger ratios make it bigger (FIG. 10B), 3) Knee abduction moment changes cause the stimulus to pinch (excessive valgus) or expand (excessive varus) at the middle (FIG. 10C), 4) Foot position changes the width of the stimulus base; feet too close together cause the base to be narrower than the top and too far apart cause it to be wider than the top (FIG. 10D), 5) VGRF asymmetry causes the corner of increased load to drop (FIG. 10E), and 6) The stimulus translates left or right if landing position deviates laterally from a target on the floor (FIG. 10F). The feedback stimulus appearance changes in real-time according to the values of these biomechanical variables as the athlete performs the exercise.

Figure 10A:
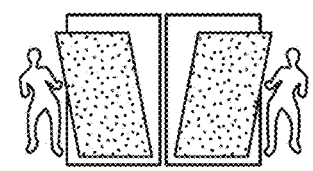
FIGS. 10A-10F are illustrative views of calculation of biomechanical deficits and associated biofeedback represented for each specific calculated input.
Figure 10B:
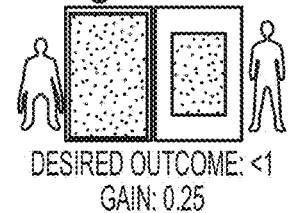
Figure 10C:
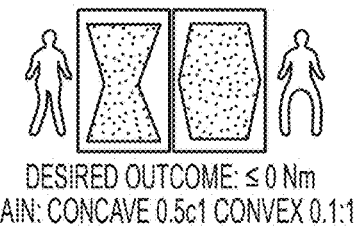
Figure 10D:
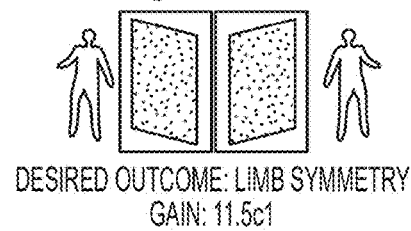
Figure 10E:
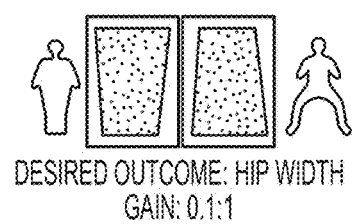
Figure 10F:
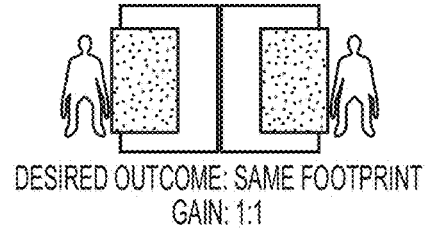

FIGS. 10A-10F illustrate the calculation of biomechanical deficits and the associated biofeedback represented for each specific calculated input. The trunk lean configuration of the stimulus 18 as shown in FIG. 10A is a result of angular displacement of the acromioclavicular joint marker relative to the anterior superior iliac spine marker in the frontal plane. The knee to hip moment configuration of the stimulus 18 as shown in FIG. 10B is a result of inverse dynamics moment ratio calculated as hip to knee sagittal plane moment. The knee abduction moment configuration of the stimulus 18 as shown in FIG. 10C is a result of inverse dynamics moment determination from the magnitude and direction of the ground reaction force relative to the knee joint center in the frontal plane. FIG. 10D illustrates the foot placement configuration of the stimulus 18 which results from the width between the right and left ankle joint centers relative to the width between hip joint centers in the frontal plane. Finally, the landing position configuration of the stimulus of FIG. 10F is displacement of the ankle joint centers from the starting position in the frontal plane.

After receiving basic instruction about how to accomplish the exercises, athletes must discover the movement pattern that produces a stimulus shape as close to the desired rectangle as possible and maintain the stimulus in a large rectangular shape as best as she can on each repetition. No explicit directions will be provided to athletes on their movement other than instruction to achieve the goal "rectangle" shape. Based on our preliminary studies, we expect that the aNMT protocol will be especially beneficial to an athlete who can respond to self-guided, implicit learning strategies to correct multiple deficits that are likely cumulative in the exacerbation of injury risk. Given the automated, objectively prescribed mapping between the athlete and the stimulus, there is no interaction between the technician and the stimulus during aNMT delivery. This ensures blinding of the technician.

Virtual Reality (VR) may be an effective tool utilized with the system and method of the present disclosure to analyze training transfer to realistic motion, including sport related, performance. Unlike outdoor motion capture solutions, VR offers a fully standardized, controlled environment and, in combination with untethered/unencumbered freedom of movement, can induce a sense of immersion to facilitate athlete responses that parallel real-world sport responses. VR scenarios may provide controlled environments uniquely equipped to test sport-specific skill transfer following aNMT intervention. These scenarios utilize sport-specific tasks in virtual environments, embedded in the sport's context, that require strings of neuromuscular training-specific movements to accomplish sport-relevant task goals. This allows assessment of training transfer to the biomechanics of maneuvers that map onto specific neuromuscular training tasks. It also enables systematic development of biomechanical profiles across a variety of sport-specific events and stimuli.

System Operation and Operator Interface

In the following description, reference will be made to the operator interface 22 of FIG. 11, the system flow chart of FIG. 12, the file modules or processing sequences of FIG. 13, the executable files or functions of FIG. 14, and the data structures of FIG. 15. Software, including machine readable code, is executed within processors of the motion acquisition controller 28 and the motion analysis and feedback controller 30. With reference to FIG. 12, the illustrative process starts at the program start step (block 110), where the controller 30 executes processing sequence "stimulusXML.cs". This file module serves as the main entry point for the software and is responsible for main logic and program organization.

The process continues to block 112, where the controller 30 executes processing sequences "Point.cs" and "UserHandler.cs". Processing sequence "Point.cs" is responsible for manipulations preformed on the stimulus coordinate points, such as resetting them to original valves and/or averaging multiple frames. Processing sequence "UserHandler.cs" is responsible for tracking individual user information, such as group assignment, demographic and anthropometric data, exercise progression, individual gains, scores, etc. The executable files are further shown as labels 15.A through 15.E in FIG. 14.

At the input stream step (block 114), the biomechanical data structures are received from the biomechanical acquisition system 12. More particularly, the biomechanical acquisition system samples data at block 116 from the imaging acquiring device 26 and the force sensors 38. The controller 28 then generates the biomechanical data structures ("bioM Data"). These biomechanical data structures are then transmitted at block 118 to the motion analysis and feedback system 16 at block 114. As noted above, the motion acquisition controller 28 may be Cortex. Processing sequence "amnt.cs" is responsible for establishing a connection to the source of the biomechanical data structures, importing the data structures, and terminating the connection to the data source (i.e., biomechanical acquisition system). The executable files are further shown as labels 1.A through 1.C in FIG. 14.

At step 2 (block 120), the process continues by executing processing sequences "AudioHandler.cs" and "tracker.cs". Processing sequence "AudioHandler.cs" is responsible for audio control of the program. For example, this processing sequence illustratively selects a random encouragement audio clip and/or an appropriate warning audio clip to be broadcast by the speaker of the user interface. The audio clip is illustratively played based upon input from the "Tracker.cs" processing sequence, which is responsible for tracking participant movements and calculating anthropometric data. Illustratively, input to the "Tracker.cs" processing sequence includes biometric data structures, while output includes data about participants and their respective movements. The executable files are further shown as labels 9.A through 9.F in FIG. 14, with the associated source code shown in Appendix A1.

At step 3 (block 122), the process continues by executing processing sequences "RepCounter.cs" and "Score.cs". Processing sequence "RepCounter.cs" is responsible for tracking the number of completed successful and unsuccessful exercise repetitions. Input to this processing sequence includes the biometric data structures, while output includes the number of completed successful and unsuccessful exercise repetitions. The executable files are further shown as labels 11.A through 11.C in FIG. 14. Processing sequence "Score.cs" is responsible for tracking an individual participant's score. Input to this processing sequence includes current stimulus coordinates, while output is the total deviation of the current stimulus coordinates from the goal position. The executable files are further shown as labels 12.A and 12.B in FIG. 14.

At step 4 (block 124), the illustrative process continues based upon input from the operator interface 22. As further detailed herein, one of a plurality of different exercises may be selected, including overhead squat, pistol squat, squat and/or squat jump. In response, the controller 30 executes an exercise processing sequence associated with the selected exercise. All of the illustrative exercise processing sequences share a majority of the same source code (e.g., around 80%). There are additional functions between exercises and sham, for example, that will have some additional functions specific to that particular exercise/condition.

If the overhead squat exercise is selected at the operator interface 22, then the processing sequence "OH Squat.cs" is executed. This processing sequence generates the stimulus for training the overhead squat. Input to this processing sequence includes variables to generate the stimulus (e.g., biomechanical data structures) along with gains input by the operator. Output from this processing sequence includes the current stimulus coordinates. The executable files are further shown as labels 4.A through 4.L in FIG. 14, with the associated source code shown in Appendix A2.

If the pistol squat exercise is selected at the operator interface, then the processing sequence "Pistol Squat.cs" is executed. This processing sequence generates the stimulus for training the pistol squat. Input to this processing sequence includes variables to generate the stimulus (e.g., biomechanical data structures) along with gains input by the operator. Output from this processing sequence includes the current stimulus coordinates. The executable files are further shown as labels 7.A through 7.I in FIG. 14, with the associated source code shown in Appendix A3.

If the squat exercise is selected at the operator interface, then the processing sequence "Squat.cs" is executed. This processing sequence generates the stimulus for training the squat. Input to this processing sequence includes variables to generate the stimulus (e.g., biomechanical data structures) along with gains input by the operator. Output from this processing sequence includes the current stimulus coordinates. The executable files are further shown as labels 6.A through 6.J in FIG. 14, with the associated source code shown in Appendix A4.

If the squat jump exercise is selected at the operator interface, then the processing sequence "Squat Jump.cs" is executed. This processing sequence generates the stimulus for training the squat jump. Input to this processing sequence includes variables to generate the stimulus (e.g., biomechanical data structures) along with gains input by the operator. Output from this processing sequence includes the current stimulus coordinates. The executable files are further shown as labels 8.A through 8.J in FIG. 14. The associated source code is the same as that for the squat exercise, with an added inAir tracker variable (returned from the function in the tracker class ("tracker.cs")) to render its display.

The sham function is illustratively executed at step 5 (block 126). More particularly the processing sequences "Sham.cs" and "ImportSham.cs" are executed. The "Sham.cs" processing sequence modifies the stimulus coordinates by adding noise to the signal representing the biometric data structure. Input to this processing sequence includes the stimulus coordinates and a noise level input. Output from this processing sequence includes current sham stimulus coordinates. The executable files are further shown as labels 5.A through 5.D in FIG. 14, with the associated source code shown in Appendix A5.

The "ImportSham.cs" processing sequence is responsible for importing a randomly selected text file consisting of the numerical values used to create sham feedback. Values from this processing sequence are used in creating the sham stimulus. The executable files are further shown as label 2.A in FIG. 14.

The process then continues to step 6 (block 128) by executing processing sequences "XMLMap.cs" and "TCPServerXML.cs". The "XMLMap.cs" processing sequence defines and constructs data structure to be used in communicating between the displays of the operator interface and the user interface and other portions of the program. Output from this processing sequence are illustratively data structure used to communicate and operate the displays. The "TCPServerXML.cs" processing sequence is responsible for integrating and maintaining a connection with the displays of the operator interface and the user interface. Input includes information used in making a connection to the displays of interfaces 20 and 22, while output includes stimulus values sent to the displays of interfaces 20 and 22. The display connection is shown as block 128 and is facilitated by execution of the processing sequence "DeformationHandler.cs" (which helps display the stimulus 18, but has a primary function of interacting with the interfaces 20 and 22).

As further detailed herein, the stimulus coordinates as determined by the exercise processing sequences will define the graphical stimulus 18 shown on the displays of the interfaces 20 and 22. A participant 14 will attempt to maintain the stimulus 18 within the goal reference on the display 42.

Figure 16A:
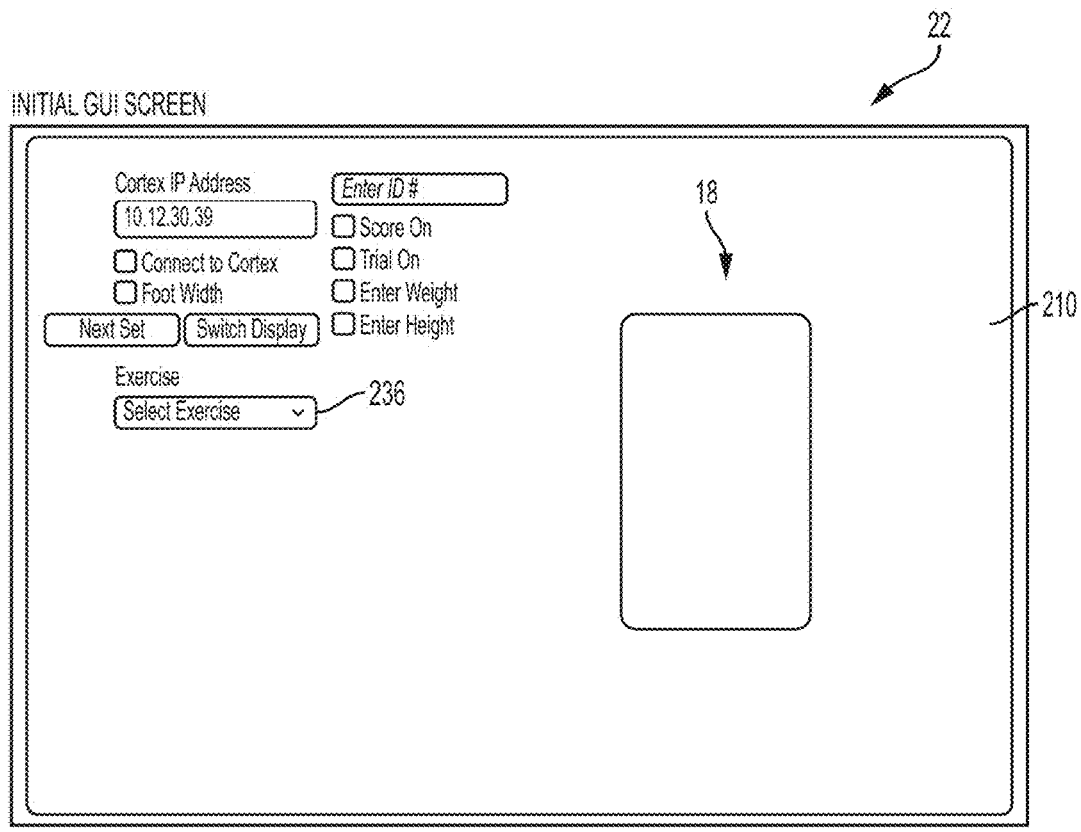
FIG. 16A is a plan view of the illustrative graphical user interface (GUI) screen of the operator interface of FIG. 11 in an initial configuration.

The illustrative operator interface 22 is shown in different configurations in FIGS. 16A-21A. FIG. 16A is a plan view of the illustrative graphical user interface (GUI) screen 210 of the operator interface of FIG. 11 in an initial configuration. FIG. 16B is a flowchart representing operation of the illustrative GUI screen of FIG. 16A in the initial configuration. As shown in FIG. 11, the illustrative operator interface 22 includes a display 210 including the stimulus 18, replicating that shown on the user display 42. A manager or configuration panel 212 includes options controlled by the processing sequence "GUIManager.cs" and corresponding executable instructions (functions 13.A-13.H and 15.A). The configuration panel 212 allows the operator to modify gains and used exercise variables. A general option panel 214 includes options for connecting to the biomechanical acquisition system 12 and the external display 42. The general option panel 214 also includes additional options for initializing calculation of anthropometric data (functions 9.A-9.G and 13.A-13.H). For example, the general option panel 214 includes buttons 238, 240, 242, 244, and 246 for selecting different variables for use, and inputs 248, 250, 252, 254, and 256 (including transform buttons and slide bars) for altering gain of the selected variables.

As further shown in FIG. 16A, the operator interface 22 includes a plurality of options for connecting to the biomechanical acquisition system 12 and user interface 20. More particularly, an address field 216 is provided for entering the IP address of the biomechanical acquisition system 12, illustratively the Cortex IP Address. A connect button 218 is provided to connect the motion analysis and feedback system 16 to the biomechanical acquisition system 12. An ID field 220 is provided for entering participant identification (e.g., number or name). A score on button 222 is provided for activating scoring of the stimulus, and a trial on button 224 is provided for starting the selected exercise. A next set button 226, resets the system for a next set of exercises. A switch display button 228 may be provided to switch output between different displays 42 (should multiple displays 42 be available for use). Any one of the plurality of different exercises may be entered by a drop down exercise field 236 (e.g., overhead squat, pistol squat, squat and/or squat jump).

Additional options are provided for initializing the calculation of anthropometric data (functions: 9.A-9.G and 13.A-13.H). A foot width button 230 is provided for calculating relative foot width of the participant 14 based on input from the force sensors 38. An enter weight button 232 and an enter height button 234 are provided for calculating the weight and the height of a participant 14, based on input from the force sensors 38 and markers 24, respectively. More particularly, weight is measured from the force sensors 38, while height is determined by the position (x, y, z) of the markers 24 attached to a participant's body. This information is illustratively provided by the biomechanical acquisition system 12. While this is illustratively the Cortex program, it could be from any source capable of 3D tracking. The processing sequence "Tracker.cs" manipulates this data. These are generally algorithms contained in machine executable code to calculate the various variables.

Figure 16B:
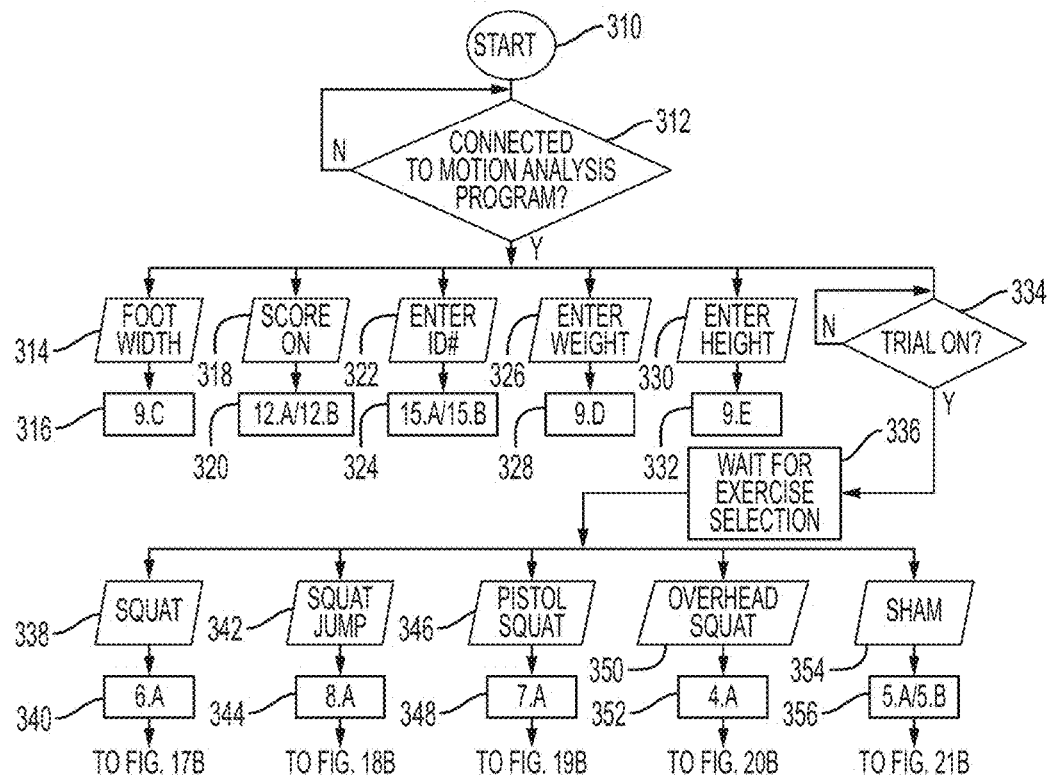
FIG. 16B is a flowchart representing operation of the illustrative GUI screen of FIG. 16A in the initial configuration.

With reference now to FIG. 16B, a method of operating the operator interface 22 in the initial configuration starts a block 310. At decision block 312, the controller 30 decides whether a connection has been established with the biomechanical acquisition system 12. If not, the controller 30 returns and waits for such a connection. If a connection has been made, then the process continues to a branch, where various inputs may be received from the operator interface 22 shown in FIG. 16A. For example, input from the foot width button 230 may be received at block 314, where the program proceeds to function 9.c (FIG. 14) at block 316. If input from the score on button 222 is received at block 318, then the process proceeds to functions 12.a/12.b (FIG. 14) at block 320. If an ID is entered in the field 220 at block 322, then the controller 30 continues to functions 15.a/15.b (FIG. 14) at block 324. If input is received by the enter weight button 232 at block 326, then the controller 30 continues to function 9.d at block 328. Similarly, if input is received by the enter height button 234 at block 330, then the controller 30 continues to function 9.e at block 332.

At decision block 334, the controller 30 determines whether the trial on button 224 has been activated. If no, then the controller 30 waits for further input. If yes, then the controller 30 waits for an exercise selection at block 336. The exercise selection may be made at field 236 shown in FIG. 16A. Exercise selections may include, for example, squat, squat jump, pistol squat, overhead squat, and/or sham.

If the squat exercise is selected at block 338, then the controller 30 proceeds to function 6.a at block 340. If the squat jump is selected at block 342, then the controller 30 continues to function 8.a at block 344. If the pistol squat is selected at block 346, then the controller 30 continues to function 7.a at block 348. If the overhead squat is selected at block 350, then the controller 30 continues to function 4.a at block 352. Finally, if sham is selected at block 354, then the controller 30 proceeds to functions 5.a/5.b at block 356.

Figure 11:
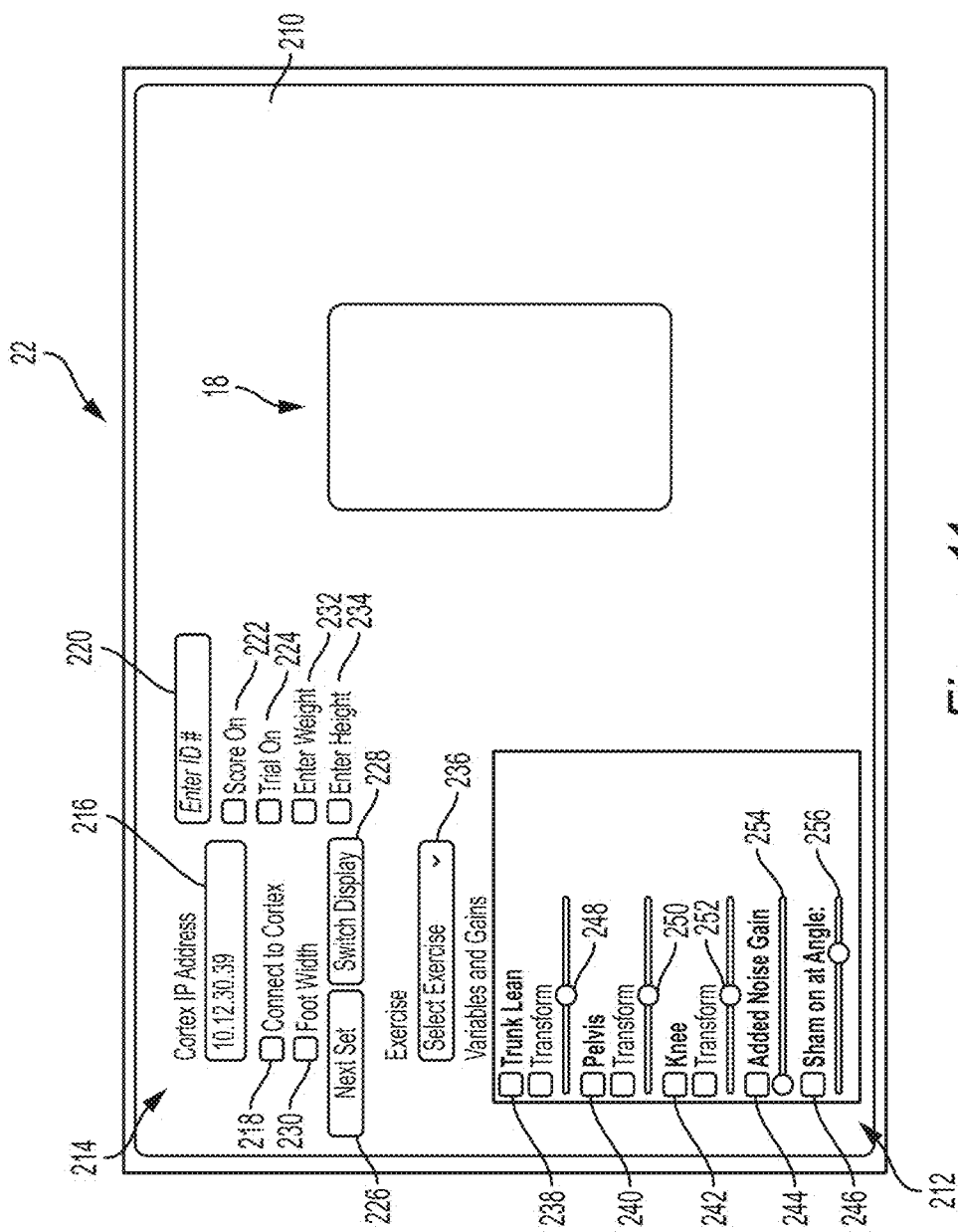
FIG. 11 is a plan view of an illustrative graphical user interface (GUI) screen of the operator interface of FIG. 1.
Figure 12:
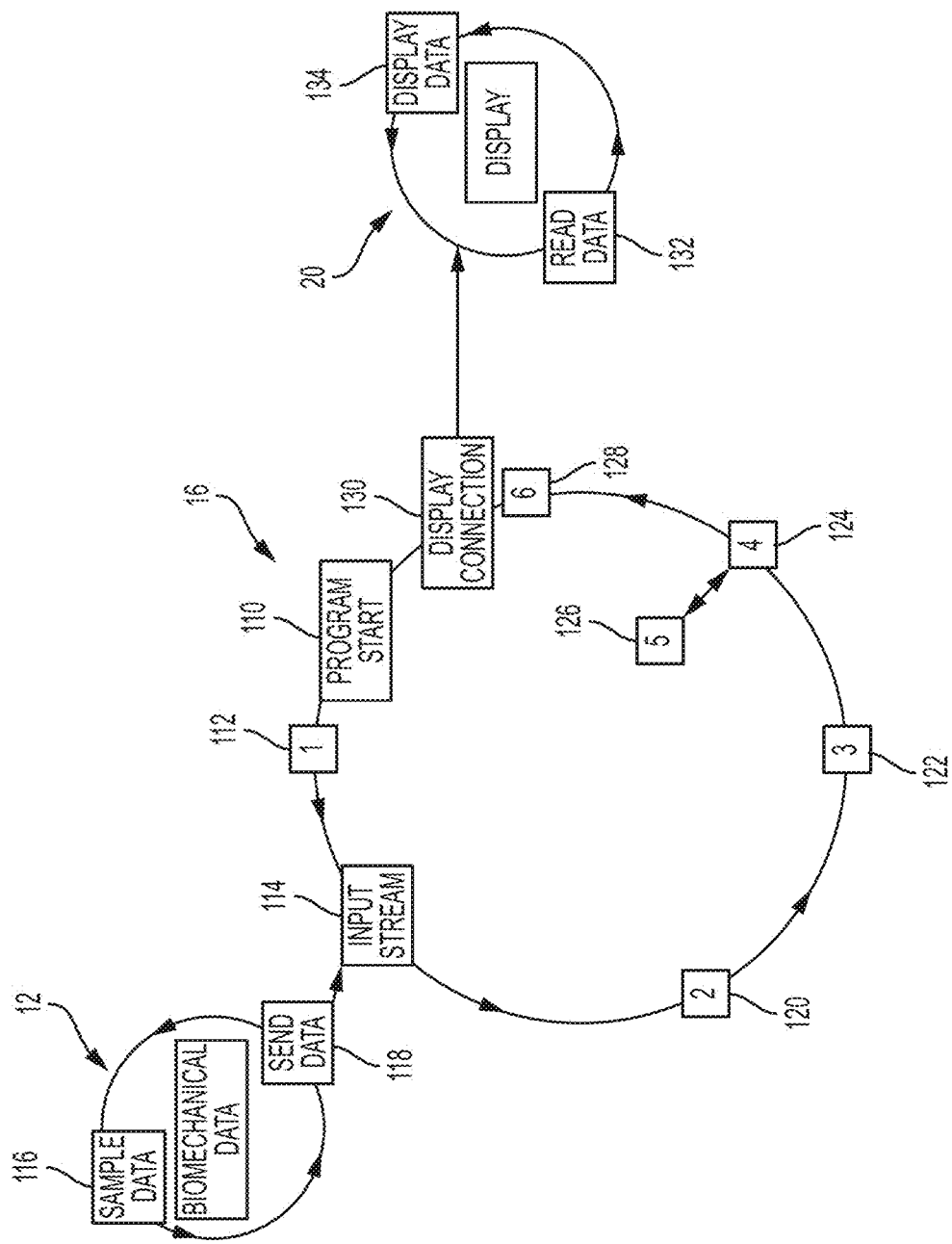
FIG. 12 is a flow chart of an illustrative operation of the illustrative augmented neuromuscular training system of FIG. 1.
Figure 17A:
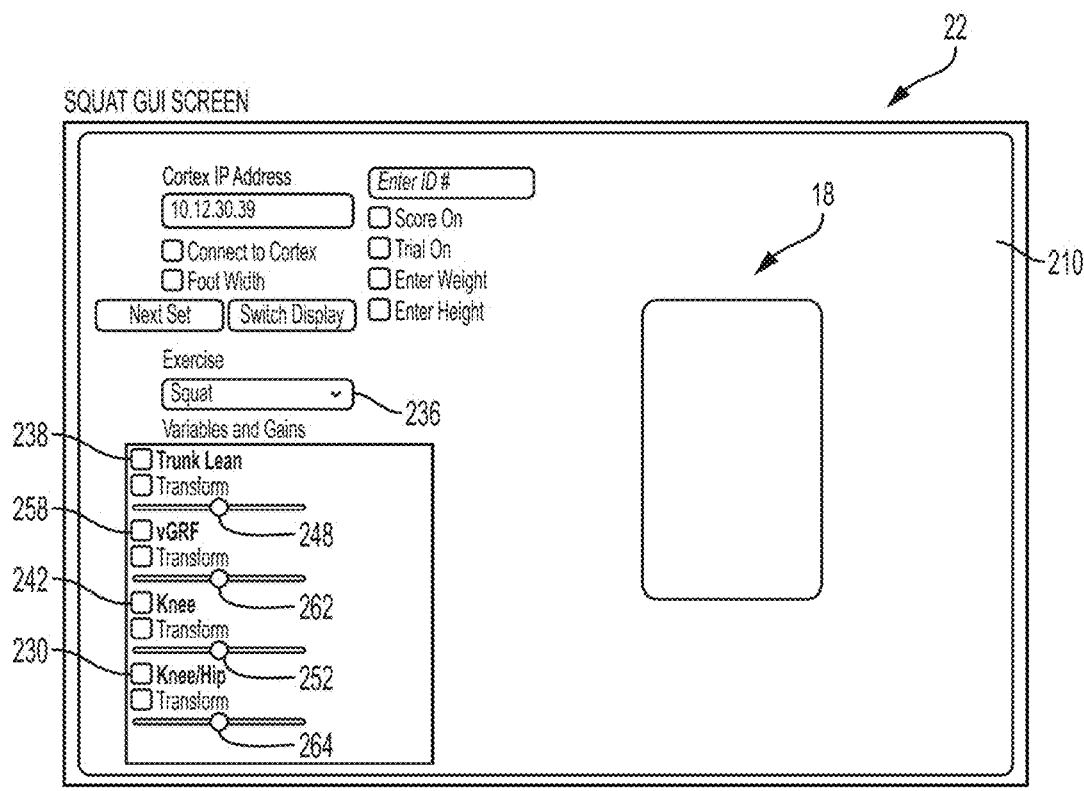
FIG. 17A is a plan view of the illustrative graphical user interface (GUI) screen of the operator interface of FIG. 11 in an squat exercise configuration.
Figure 17B:
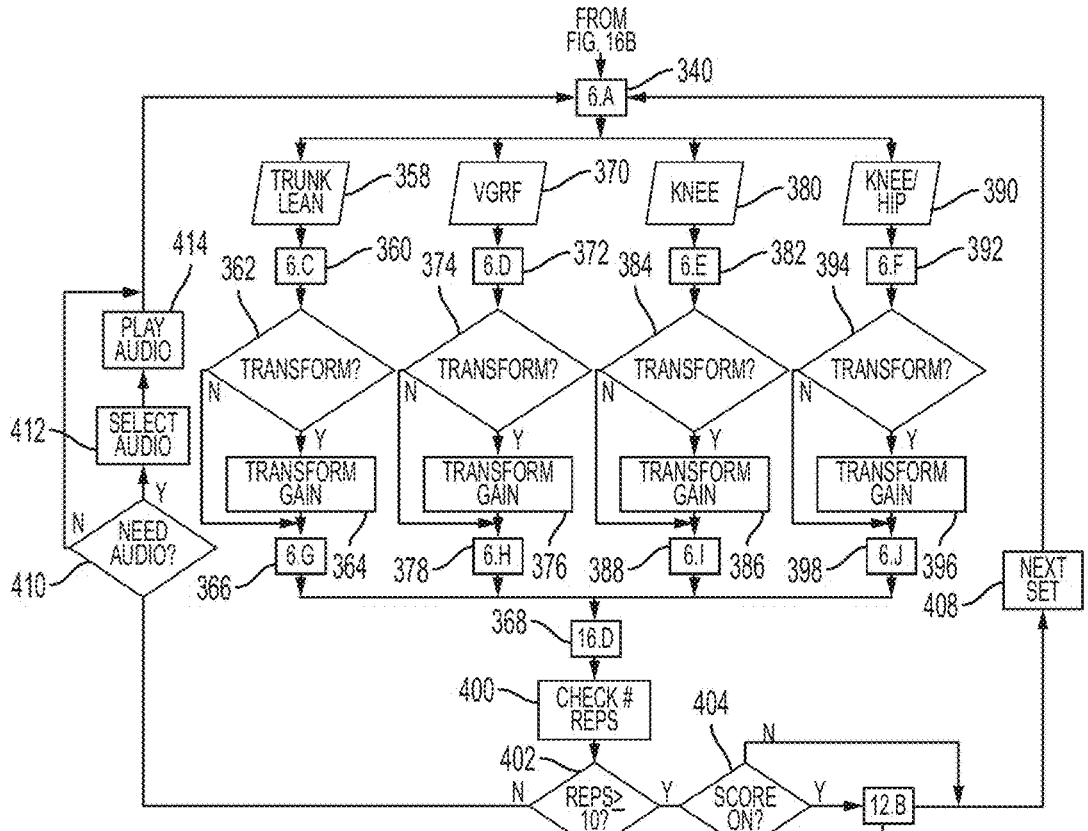
FIG. 17B is a flowchart representing operation of the illustrative GUI screen of FIG. 17A in the squat exercise configuration.

FIG. 17A is a plan view of the illustrative graphical user interface (GUI) screen of the operator interface of FIG. 11 in a squat exercise configuration. FIG. 17B is a flowchart representing operation of the illustrative GUI screen 210 of FIG. 17A in the squat exercise configuration.

If the squat exercise is selected, the process continues to function 6.a at block 340. The controller 30 then looks for input from the variables and gain section 212 of the operator interface 22. If trunk lean is entered at block 358, then a new function 6.c is executed at block 360. The controller 30 then inquires at block 362 if the transform button of input 248 has been activated. If not, the process continues to function 6.g at block 366. If the transform button of input 248 has been activated, then the gain is transformed or modified at block 364. More particularly, by activating the transform button of input 248 the controller 30 may make the feedback gains linear, quadratic or cubic. Additionally, manipulation of the slide bar of input 248 varies the amount of gain applied to the trunk lean variable. The process then continues to function 6.g at block 366.

At block 370, the controller 30 looks for VGRF input 258. If so, then the controller 30 continues to function 6.d at block 372. Again, the controller 30 then inquires at block 374 if the transform function has been activated. If not, the controller 30 continues to function 6.h at block 378. If the transform function has been activated, then the gain is transformed at block 376. The process continues to function 6.h at block 378.

If knee button 242 is activated at block 380, then the controller 30 continues to function 6.e at block 382. Again, the controller 30 then asks at block 384 if the transform function has been activated. If not, the system continues to function 6.i at block 388. If the transform function has been activated, then the gain is transformed at block 386. The process continues to function 6.i at block 388.

Finally, if the knee/hip button 260 has been entered at block 390, then the function continues to block 6.f at block 392. Again, the controller 30 then asks at block 394 if the transform function has been activated. If not, the controller 30 continues to function 6.j at block 398. If the transform function has been activated, then the gain is transformed at block 396. The process continues to function 6.j at block 398.

Following blocks 366, 378, 388 and 398, the process continues at block 368, where function 16.d is executed causing data to be sent to the displays 42 and 210 (via processing sequence "TCPServerXML.cs"). Next, the number of reps are checked at block 400 (functions 11.a-11.c of FIG. 14). At decision block 402, if the reps are greater than or equal to 10 then the controller 30 continues to decision block 404, where the controller 30 inquires whether the score on 222 has been activated. If not, then the controller 30 continues to the next set at block 408 where the number of reps is set to zero and the score is reset. If the score on 222 has been activated, then function 12.b is activated at block 406. Returning to decision block 402, if the number of reps is not greater than or equal to 10, then the controller 30 continues to audio decision block 410. If audio is not needed, then the controller 30 returns to function call 6.a at block 340. If audio is needed, then audio is selected at block 412 and audio is played by speaker 44 at block 414.

Based upon different flagged values in "amnt.cs", Table 2 below illustrates potential audio statements that may be played by speaker 44 at block 414:

TABLE 2

| Audio File | Description |
|---|---|
| Squat_Deeper | Reminds a user to squat deeper (lower) |
| Reset_Feet | Informs users that they need to realign their feet |
| Slow_Down | Informs a user that they are perfomring the exercise too quickly |
| Touch_Lightly | Reminds user to touch the floor as lightly as possible during pistol squat |
| Keep_Bar_Up | Informs user when they are incorrectly holding the bar during overhead squats |
| Encourage#1 | Encourages user |
| Encourage#2 | Encourages user |
| Reminder | Reminds the user to aim for the goal stimulus shape |
| Jump | Informs a user that they need to jump higher during the squat jump |

Figure 18A:
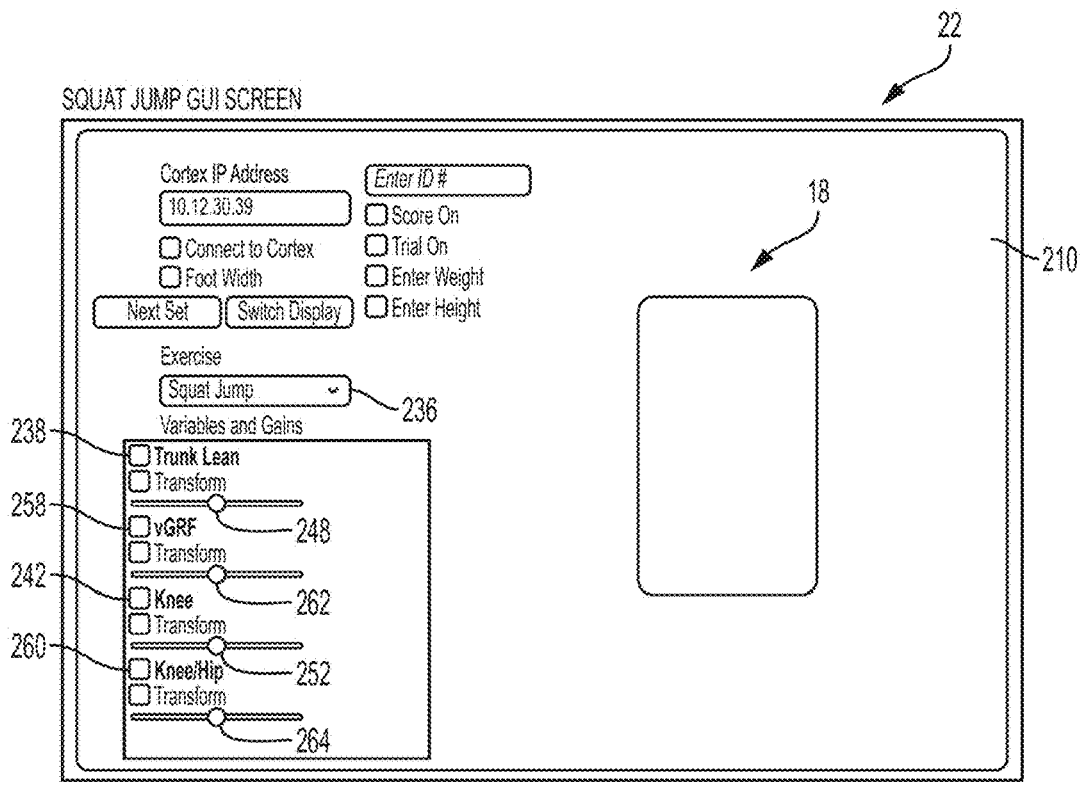
FIG. 18A is a plan view of the illustrative graphical user interface (GUI) screen of the operator interface of FIG. 11 in a squat jump exercise configuration.
Figure 18B:
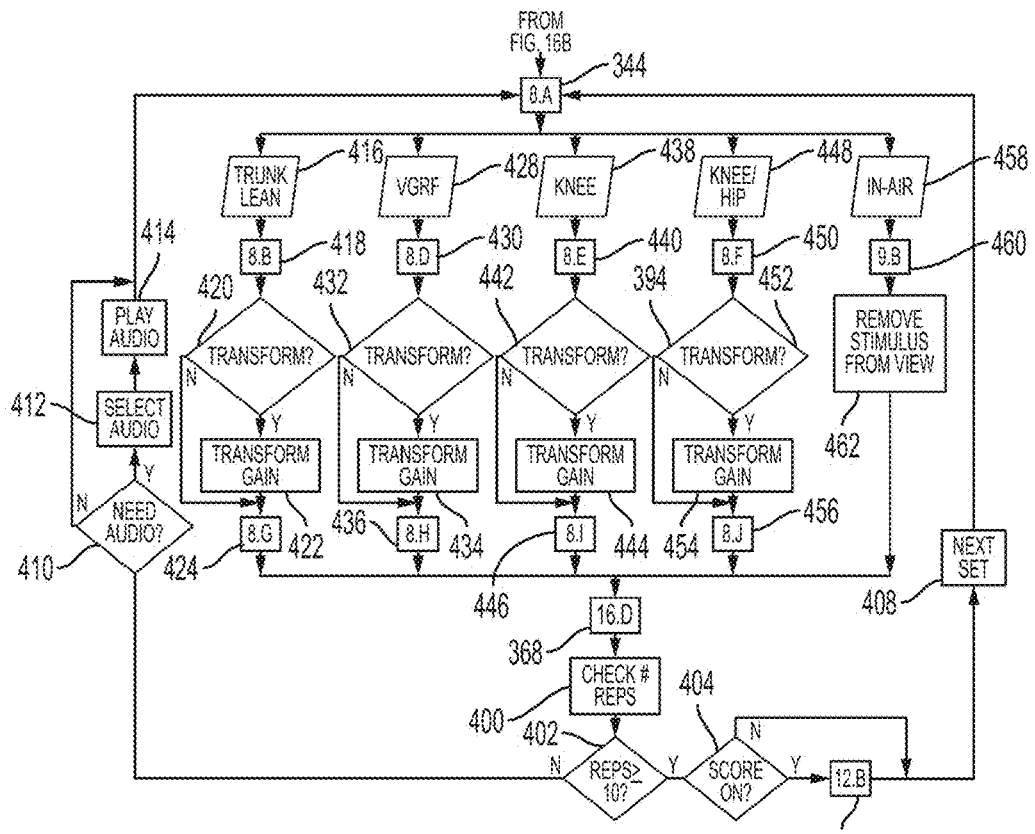
FIG. 18B is a flowchart representing operation of the illustrative GUI screen of FIG. 17A in the squat jump exercise configuration.

Turning now to FIGS. 18A and 18B, if the squat jump exercise is selected at block 342 of FIG. 16B, then the controller 30 continues to function 6.a at block 344. The controller 30 then looks for input from the operator interface 22 in a manner similar to that detailed above in connection with the flow chart of FIG. 16B. If trunk lean button 238 is activated at input 416, then a new function 8.b is executed at block 418. The controller 30 then inquires at block 420 if the transform button 248 has been activated. If not, the process continued to function call 8.g at block 424. If the transform button 248 has been activated, then the gain is transformed at block 422. The process continues to function 8.g at block 424.

If the VGRF button 258 is activated at input 428, then the controller 30 continues to function call 8.*d* at block 430. Again, the controller 30 then asks at block 432 if the transform function has been activated at input 262. If not, the controller 30 continues to function call 8.*h* at block 436. If the transform function has been activated, then the gain is transformed at block 434. The process continues to function call 8.*h* at block 436.

If the knee button 242 is activated at input 438, then the controller 30 continues to function 8.*e* at block 440. Again, the controller 30 then asks at block 442 if the transform function has been activated. If not, the controller 30 continues to function call 8.*i* at block 446. If the transform function has been activated, then the gain is transformed at block 444. The process continues to function call 8.*i* at block 446.

If the knee/hip button 260 is activated at block 448, then the process continues to function 8.*f* at block 450. Again, the controller 30 then asks at block 452 if the transform function has been activated. If not, the controller 30 continues to function 8.*j* at block 456. If the transform function has been activated, then the gain is transformed at block 454. The process continues to function call 8.*j* at block 456.

If in-air input (biometric data from the markers 24 and/or force sensors 38) is received at block 458, then the process continues to function 9.*b* at block 460. At block 462, the stimulus 18 is removed from the display 210 (e.g., during the time that the user is detected as not being in contact with the force sensors 38).

Following blocks 424, 436, 446 and 456, the process continues, as detailed above in connection with FIG. 17B, to block 368 for executing function 16.*d*.

Figure 19A:
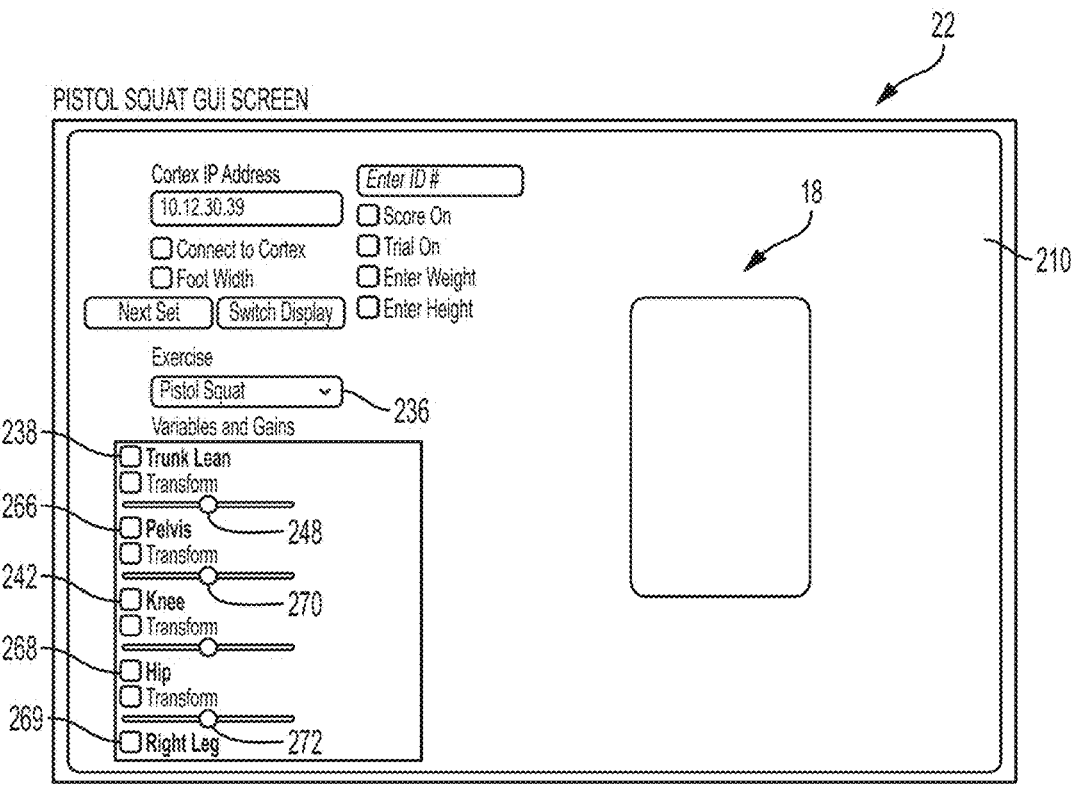
FIG. 19A is a plan view of the illustrative graphical user interface (GUI) screen of the operator interface of FIG. 11 in a pistol squat exercise configuration.
Figure 19B:
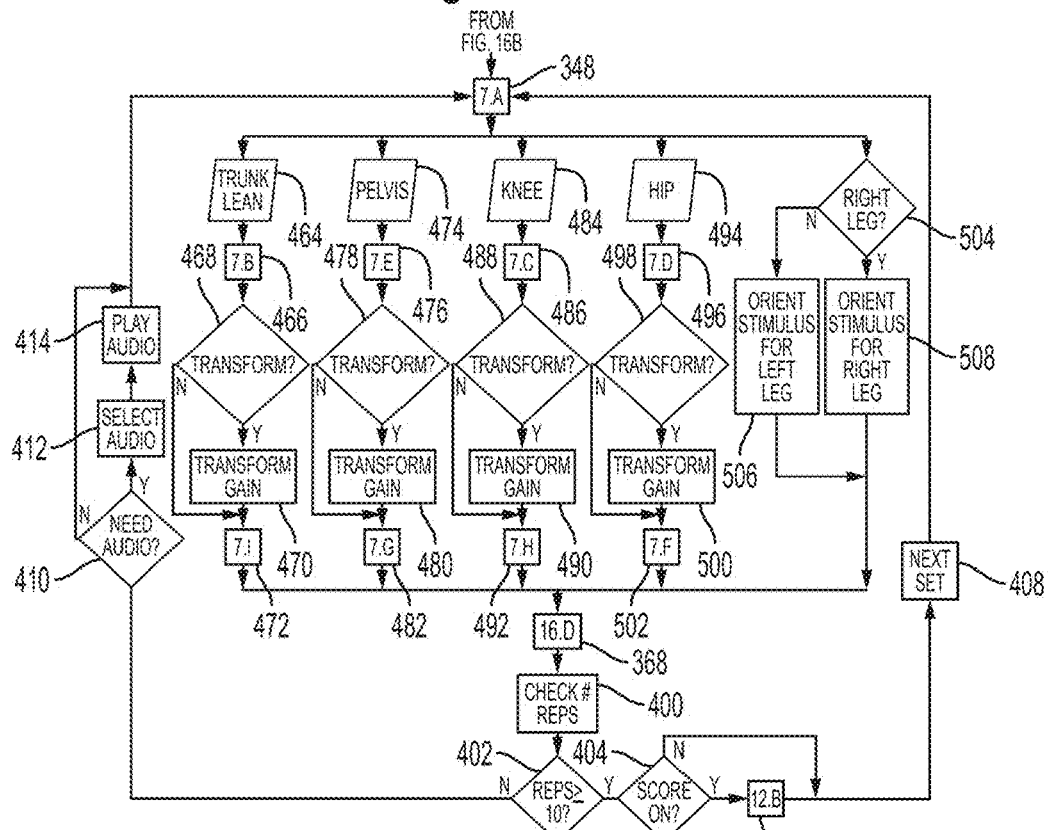
FIG. 19B is a flowchart representing operation of the illustrative GUI screen of FIG. 18A in the pistol squat exercise configuration.

Turning now to FIGS. 19A and 19B, if the pistol squat is selected as an exercise, then the controller 30 continues to function call 7.*a* at block 348. The controller 30 then looks for input from the operator interface 22 in a manner similar to that detailed above in connection with the flow chart of FIG. 16B. If trunk lean button 238 is activated at input 464, then a new function 7.*b* is executed at block 466. The controller 30 then inquires at block 468 if the transform button 248 has been activated. If not, the process continued to function call 7.*i* at block 472. If the transform button 248 has been activated, then the gain is transformed at block 470. The process continues to function 7.*i* at block 472.

If the pelvis button 266 is activated at input 474, then the controller 30 continues to function call 7.*e* at block 476. Again, the controller 30 then asks at block 474 if the transform function has been activated at input 270. If not, the controller 30 continues to function call 7.*g* at block 482. If the transform function has been activated, then the gain is transformed at block 480. The process continues to function 7.*g* at block 482.

If the knee button 242 is activated at input 484, then the controller 30 continues to function 7.*c* at block 486. Again, the controller 30 then asks at block 488 if the transform function has been activated. If not, the controller 30 continues to function call 7.*h* at block 492. If the transform function has been activated, then the gain is transformed at block 490. The process continues to function 7.*h* at block 492.

If the hip button 268 is activated at block 494, then the process continues to function 7.*d* at block 496. Again, the controller 30 then asks at block 498 if the transform function has been activated. If not, the controller 30 continues to function 7.*f* at block 502. If the transform function has been activated, then the gain is transformed at block 500. The process continues to function 7.*f* at block 502.

If a right leg input button 269 is activated, then based upon input from the force sensors 38, the controller 30 decides at block 504 whether the participant 14 is standing on her right leg. If not, then the process continues to block 506 where the controller 30 orients the stimulus 18 for the participant's left leg. If so, then the process continues to block 508 where the controller 30 orients the stimulus 18 for the participant's right leg.

Following blocks 472, 482, 492 and 502, the process continues, as detailed above in connection with FIG. 17B, to block 368 for executing function 16.*d*.

Figure 20A:
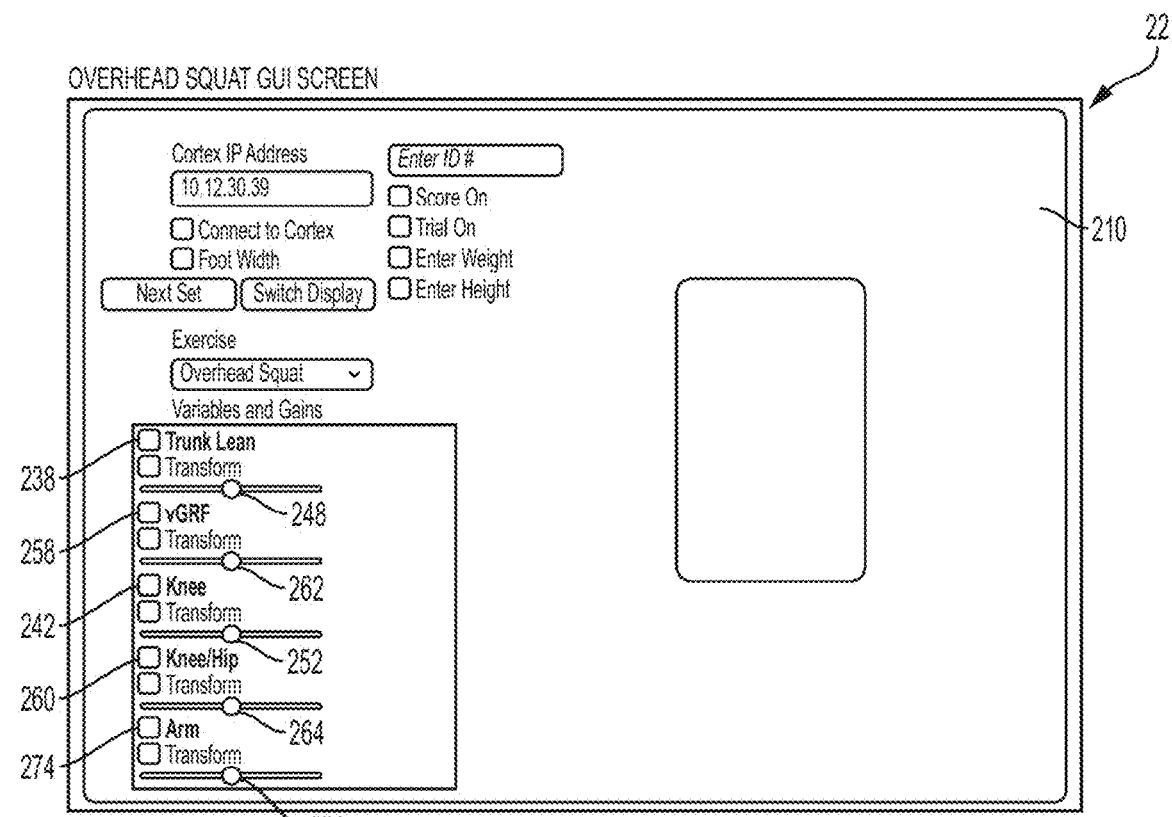
FIG. 20A is a plan view of the illustrative graphical user interface (GUI) screen of the operator interface of FIG. 11 in an overhead squat exercise configuration.
Figure 20B:
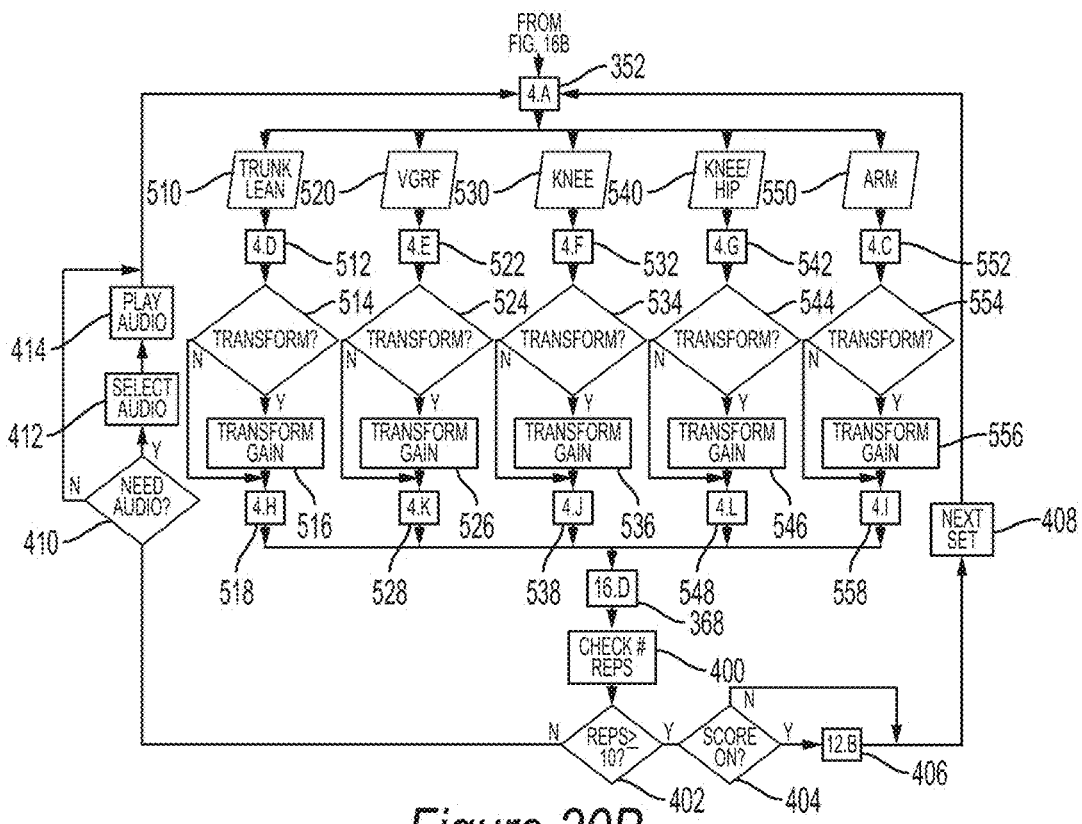
FIG. 20B is a flowchart representing operation of the illustrative GUI screen of FIG. 19A in the overhead squat exercise configuration.

Turning now to FIGS. 20A and 20B, if the overhead squat exercise is selected at the GUI, then the controller 30 continues to function 4.*a* at block 352. The controller 30 then looks for input from the operator interface 22 in a manner similar to that detailed above in connection with the flow chart of FIG. 16B. If trunk lean button 238 is activated at input 510, then a new function 4.*d* is executed at block 512. The controller 30 then inquires at block 514 if the transform button 248 has been activated. If not, the process continued to function call 4.*h* at block 518. If the transform button 248 has been activated, then the gain is transformed at block 516. The process continues to function 4.*h* at block 518.

If the VGRF button 258 is activated at input 520, then the controller 30 continues to function call 4.*e* at block 522. Again, the controller 30 then asks at block 524 if the transform function has been activated at input 262. If not, the controller 30 continues to function call 4.*k* at block 528. If the transform function has been activated, then the gain is transformed at block 524. The process continues to function call 4.*k* at block 528.

If the knee button 242 is activated at input 438, then the controller 30 continues to function 4.*f* at block 532. Again, the controller 30 then asks at block 534 if the transform function has been activated. If not, the controller 30 continues to function call 4.*j* at block 538. If the transform function has been activated, then the gain is transformed at block 536. The process continues to function 4.*j* at block 538.

If the knee/hip button 260 is activated at block 540, then the process continues to function 4.*g* at block 542. Again, the controller 30 then asks at block 544 if the transform function has been activated. If not, the controller 30 continues to function 4.1 at block 548. If the transform function has been activated, then the gain is transformed at block 546. The process continues to function call 4.*i* at block 548.

If the arm button 274 is activated at block 550, then the process continues to function 4.*c* at block 552. Again, the controller 30 then asks at block 554 if the transform function has been activated. If not, the controller 30 continues to function 4.*i* at block 558. If the transform function has been activated, then the gain is transformed at block 556. The process continues to function call 4.*i* at block 558.

Following blocks 518, 528, 538, 548 and 558, the process continues, as detailed above in connection with FIG. 17B, to block 368 for executing function 16.*d*.

Figure 21A:
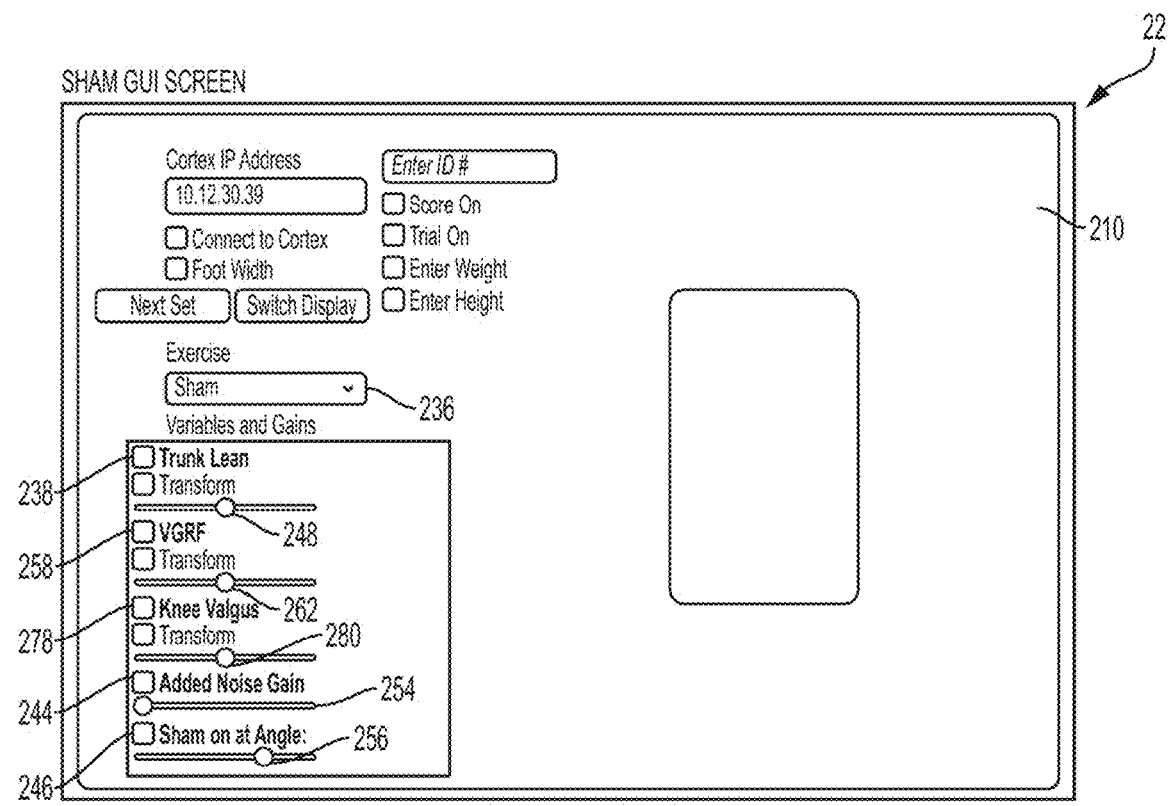
FIG. 21A is a plan view of the illustrative graphical user interface (GUI) screen of the operator interface of FIG. 11 in a sham configuration.
Figure 21B:
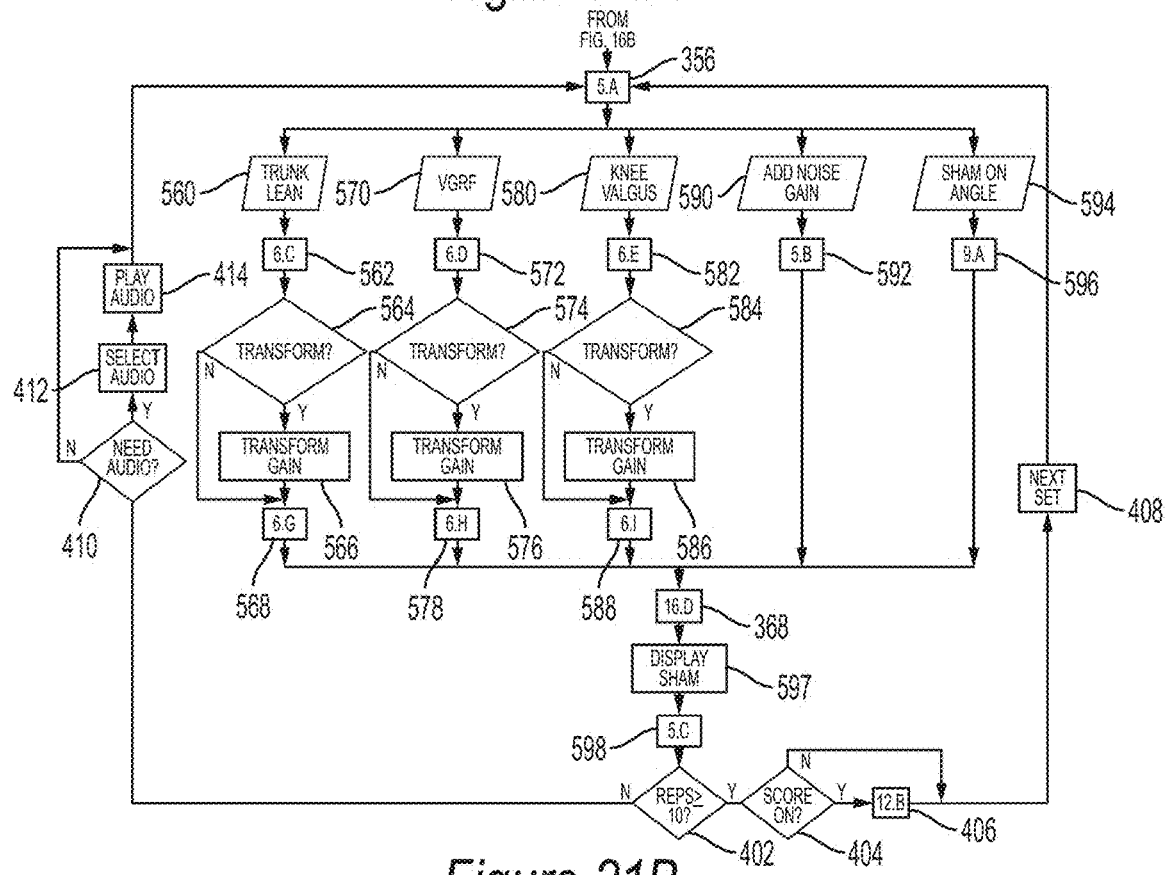
FIG. 21B is a flowchart representing operation of the illustrative GUI screen of FIG. 21A in the sham configuration.

If the sham function is selected, then the controller 30 continues to functions 5.*a*/5.*b* as shown in FIGS. 21A and 21B. The controller 30 looks for input from the operator interface 22 in a manner similar to that detailed above in connection with the flow chart of FIG. 16B. If trunk lean button 238 is activated at input 464, then a new function 6.*c* is executed at block 562. The controller 30 then inquires at block 564 if the transform button 248 has been activated. If not, the process continued to function call 6.*g* at block 568.

If the transform input 248 has been activated, then the gain is transformed at block 566. The process continues to function 6.g at block 568.

If the VGRF button 258 is activated at input 570, then the controller 30 continues to function call 6.d at block 572. Again, the controller 30 then asks at block 574 if the transform function has been activated at input 262. If not, the controller 30 continues to function 6.h at block 578. If the transform function has been activated, then the gain is transformed at block 576. The process continues to function 6.h at block 578.

If the knee valgus button 278 is activated at input 580, then the controller 30 continues to function 6.e at block 582. Again, the controller 30 then asks at block 584 if the transform function has been activated. If not, the controller 30 continues to function 6.i at block 588. If the transform function has been activated, then the gain is transformed at block 586. The process continues to function 6.i at block 588.

If added noise gain button 244 and slide bar 254 have been activated at block 590, then function 5.b is executed at block 592. Similarly, if the sham on angle button 246 and slide bar 256 have been activated at block 594, then function 9.a is executed at block 596.

The process continues to function 16.d at block 368. The sham is displayed at block 597, followed by execution of function 5.c at block 598. The process then continues to block 402 in the manner detailed above in connection with FIG. 17B.

Figure 22:
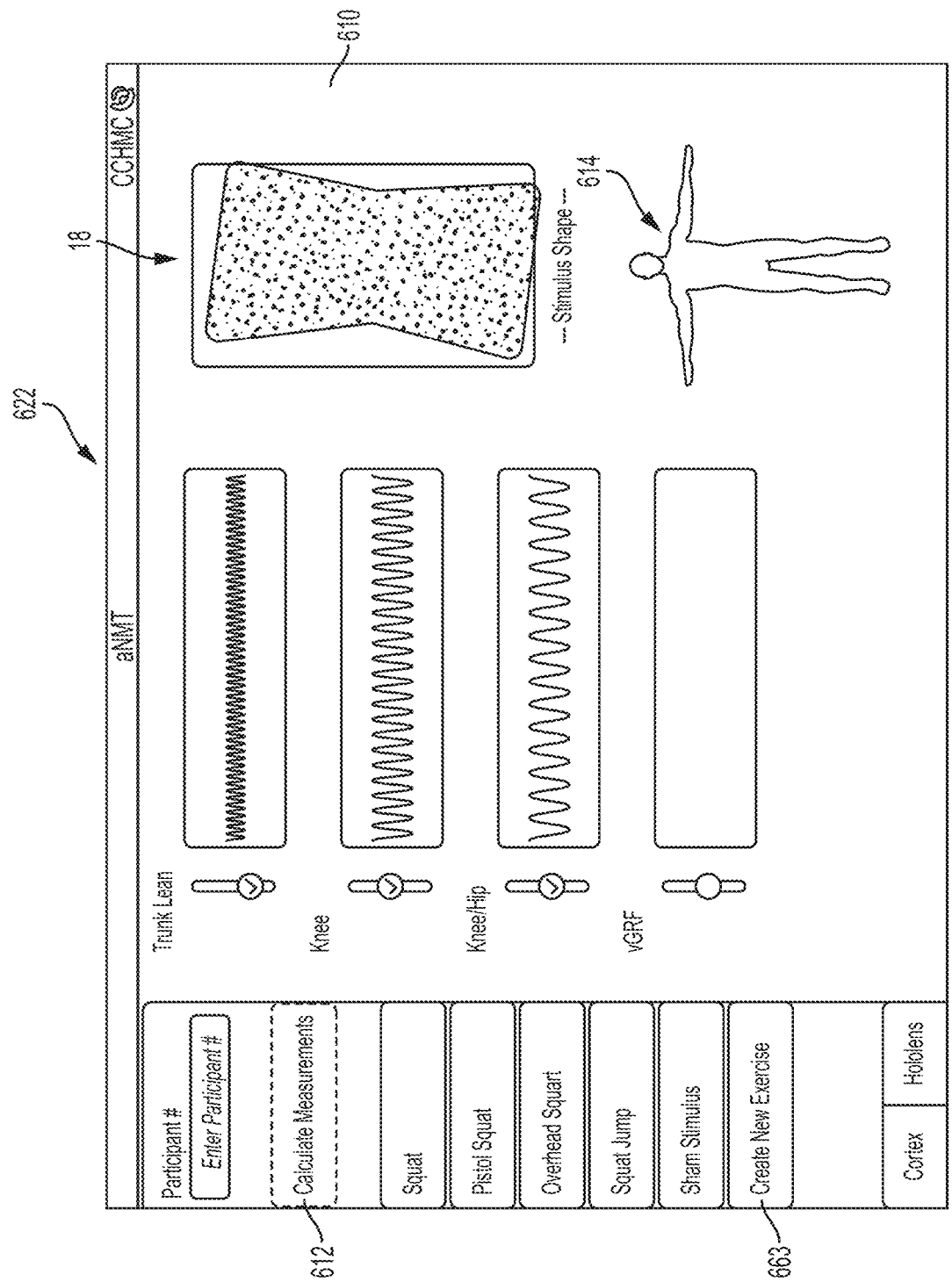
FIG. 22 is a plan view of another illustrative embodiment GUI screen of the operator interface of FIG. 1.
Figure 23A:
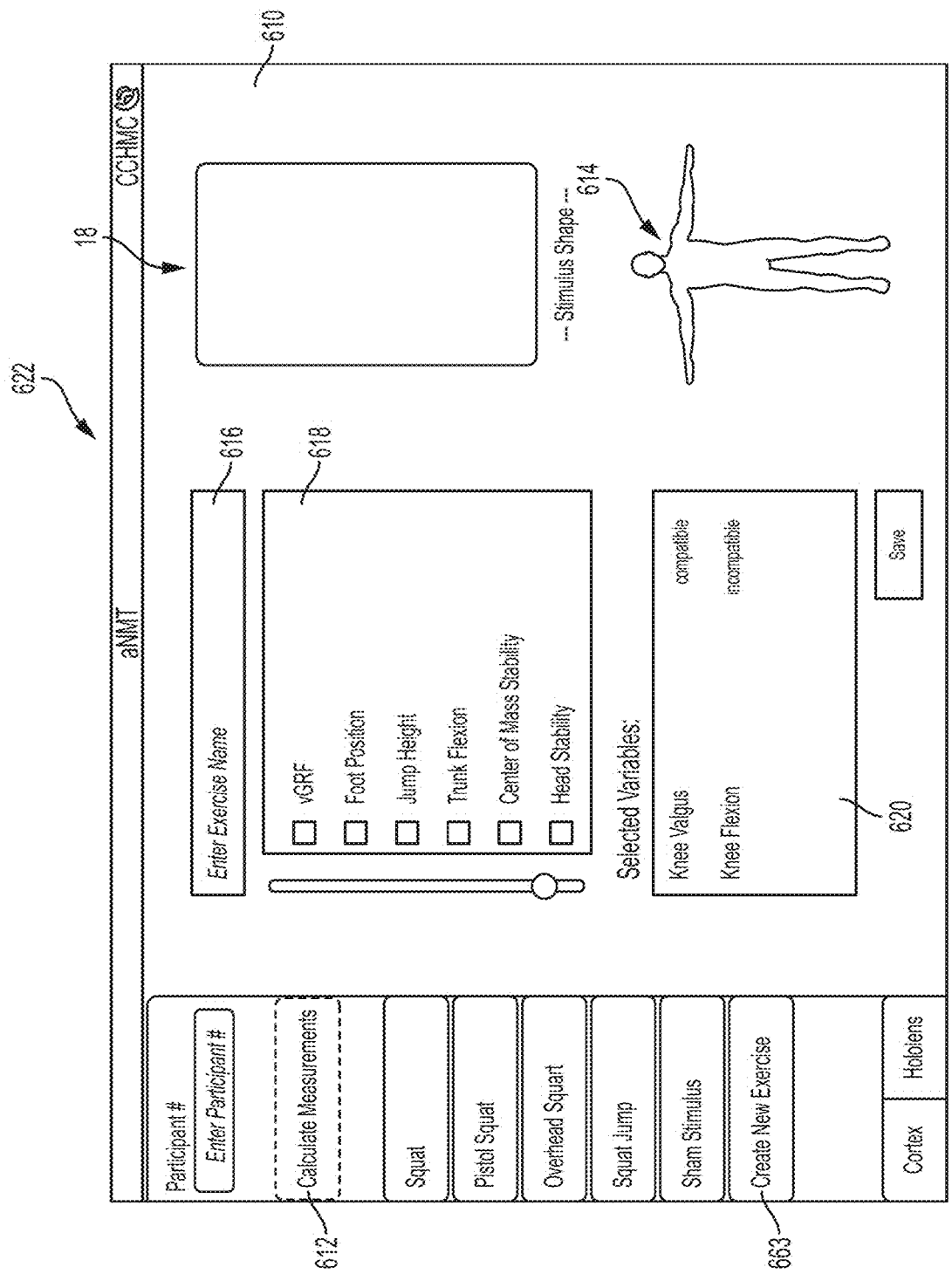
FIG. 23A is a plan view of another illustrative embodiment GUI screen of the operator interface of FIG. 1.

FIG. 22 is a plan view of another illustrative embodiment operator interface 622 including a GUI screen 610. The screen 610 is similar to screen 210 detailed above, but replaces individual demographic options (e.g., weight, height, and foot width) with a single "calculate measurements" button 612. It button 612 is selected, then a human figure image 614 will be displayed in green. With reference to FIG. 23A, the screen 610 permits an operator to create a new exercise. More particularly, the operator may name a new exercise at field 616 and then select from a library of biomechanical and other variables in section 618. The new exercise may then be exported. The controller 30 will also flag variables in section 620 that are not compatible with previously selected variables.

Figure 23B:
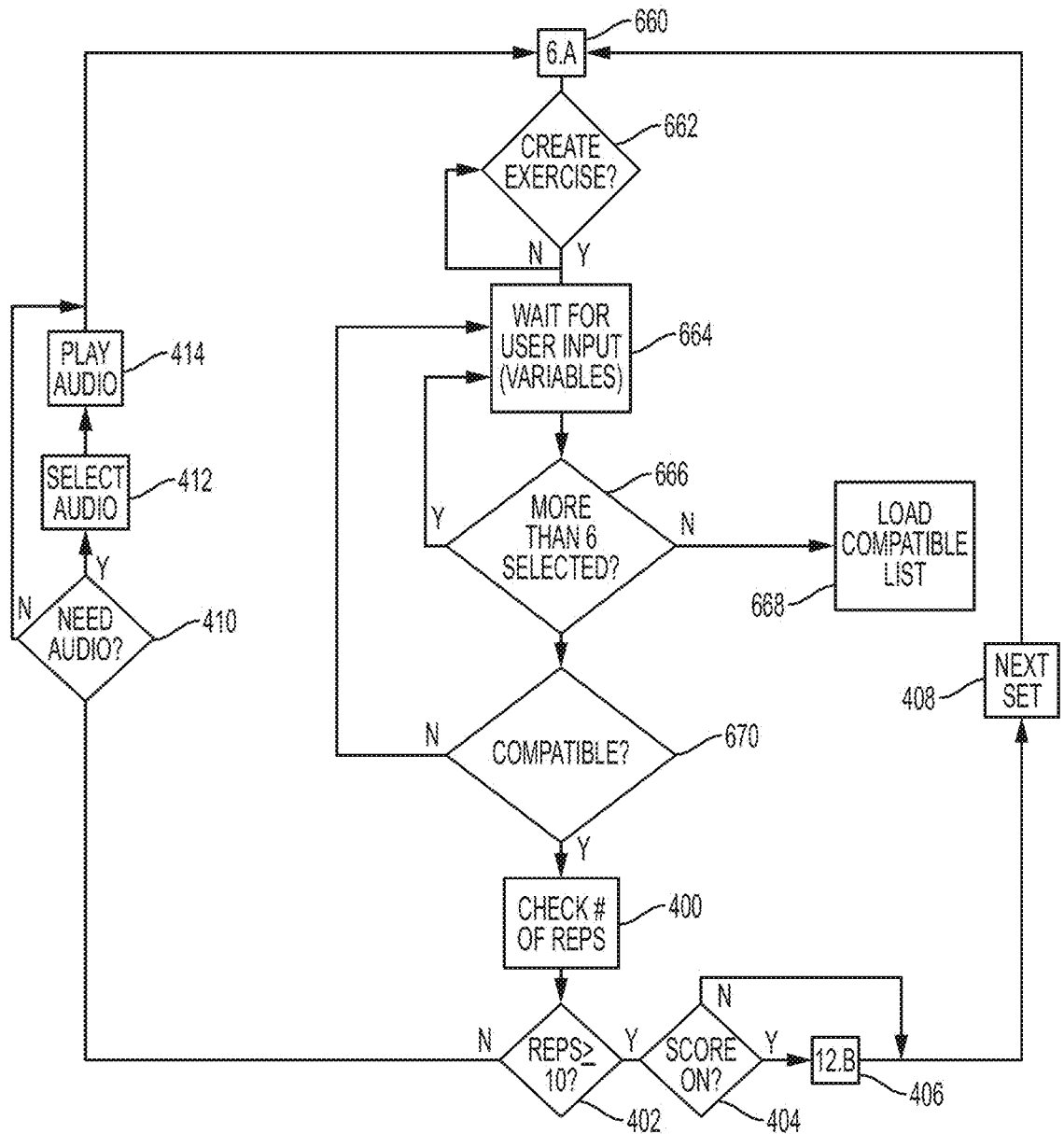
FIG. 23B is a flowchart representing operation of the illustrative GUI screen of FIG. 23A.

With reference to FIG. 23B, a method of flagging variables that are not compatible begins at block 660 where function 6.a is executed. Next, at decision block 662 the controller 30 asks whether the create new exercise button 663 on the screen 610 has been activated. If not, the process loops back to the decision block 662. If yes, then the process continues to block 664 where the controller 30 waits for user input of variables in section 618 of the screen 610. The process continues at decision block 666 where the controller asks whether more than six variables have been selected. If not, then the controller 30 loads the compatible list at block 668. If no, then the controller 30 returns to block 664 and waits for additional operator input. At block 670, the controller 30 inquires about the compatibility of the operator selected variables by comparing them to a table stored in memory 34. If they are not compatible, then the process returns to block 664 where a warning flag is provided to the user in section 620 of the screen 610. If the variables are compatible, the process continues at block 400 in the manner detailed above.

Figure 24A:
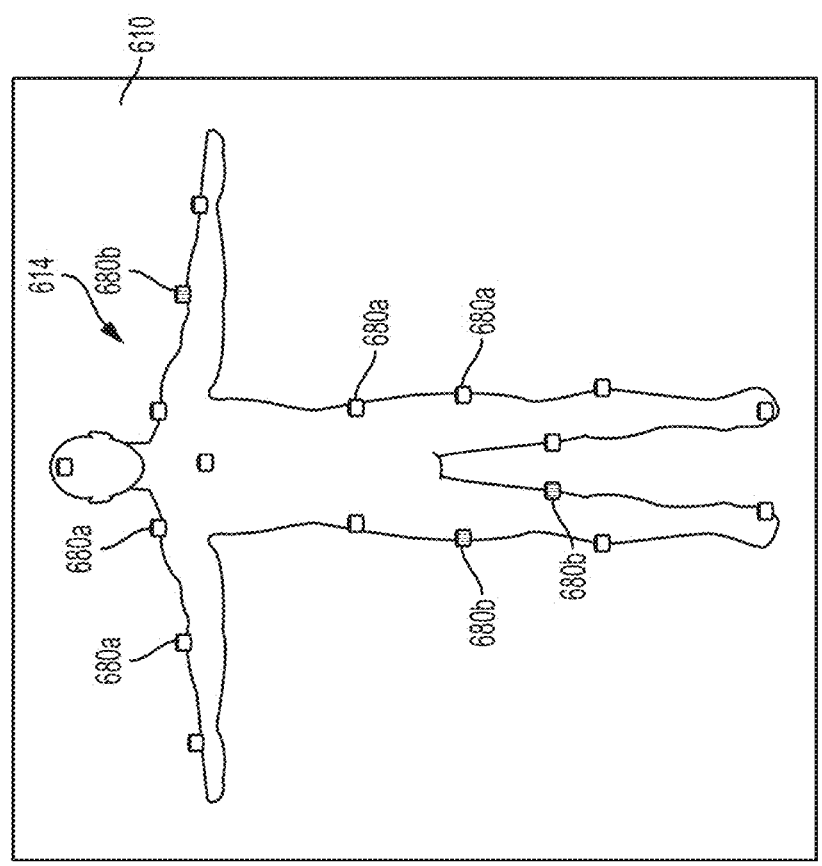
FIG. 24A is a representation of marker representations for use with the illustrative GUI screen of FIG. 23A.

FIG. 24A is a detailed view of the human figure image 614 of the screen 610. The human figure image 614 may show representations 680 of display markers 24 used to track human movement from the biomechanical acquisition system 12. User defined marker sets can be imported and linked to exercise variables, such as trunk lean. The marker representations 680 may be in one of two states: tracked 680a and untracked 680b. Tracked marker representations 680a may be shown in green, while untrack marker representations 680b may be shown in red.

Figure 24B:
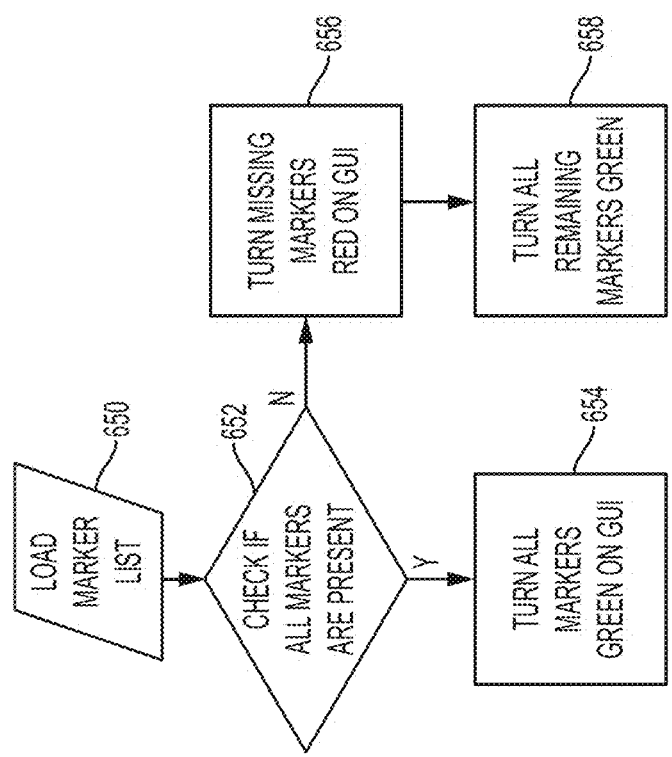
FIG. 24B is a flowchart representing operation of the marker representations of the illustrative GUI screen of FIG. 24A.

FIG. 24B is a flowchart representing operation of the marker representations 680 of illustrative GUI screen 610. Beginning a block 650, the list of markers 24 is loaded into the memory 34 of the motion analysis and feedback system 16. At block 652, the controller 30 checks to see if all markers 24 in the list are present. If yes, then all marker representations 680a are turned green on the display screen 610 at block 654. If no, then the missing markers 24 are indicated by red marker representations 680b at block 656, while all remaining markers 24 are indicated by green marker representations 680a at block 658.

Figure 25:
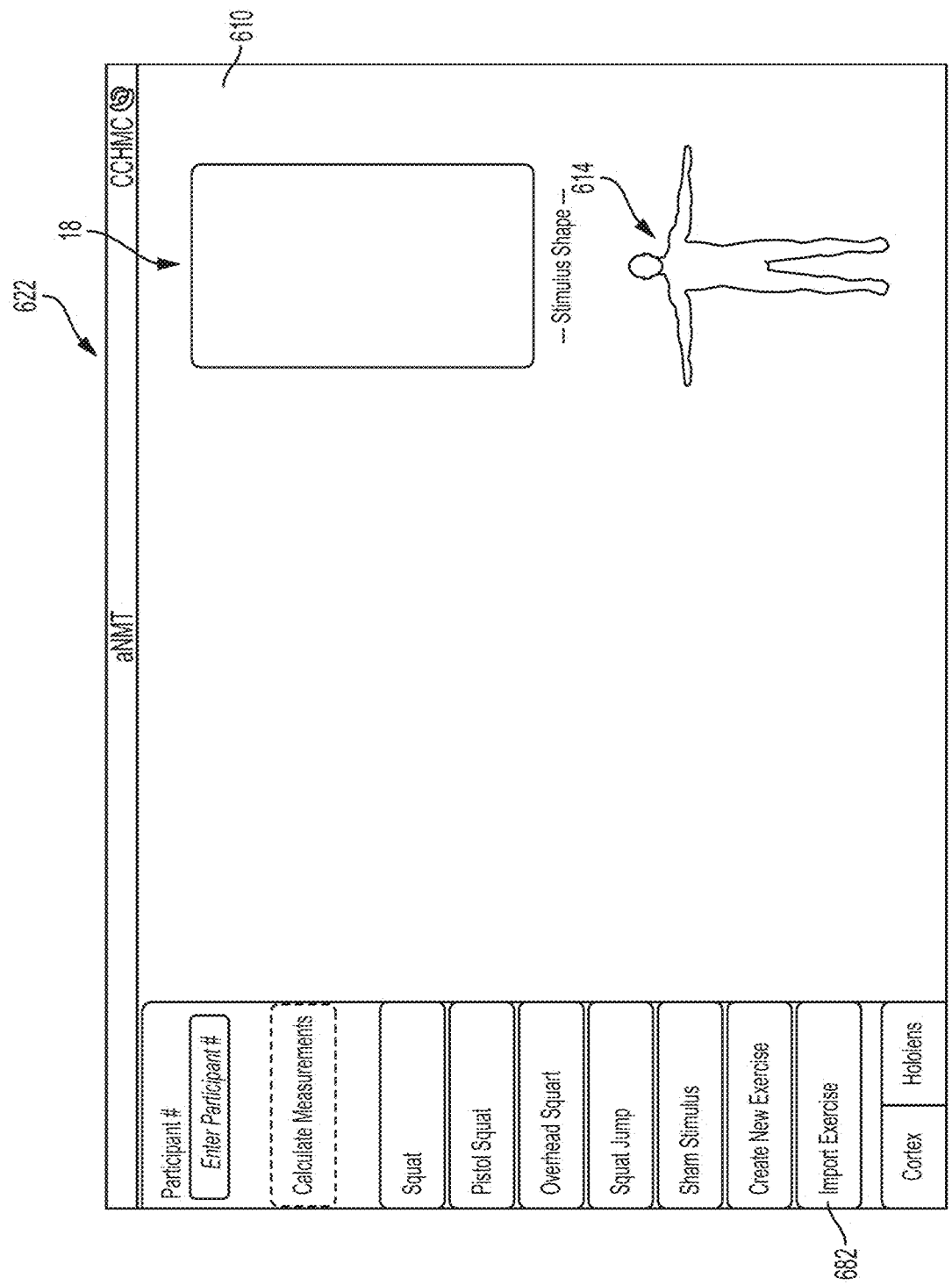
FIG. 25 is a plan view of another illustrative embodiment GUI screen of the operator interface of FIG. 1.

FIG. 25 is a plan view of another illustrative embodiment operator interface 622 including GUI screen 610. The screen 610 includes an added Import Exercise button 682 which allows a user to import locally stored user exercises and from user provided URLs.

An advantage of creating individualized feedback gains in the manner detailed above is that participants who perform atypically (e.g., below or above an average level of performance) could interact with a stimulus display that is tailored to her own needs. Effectively the gains could be used to increase or decrease the sensitivity of the display and, therefore, make it easier or more difficult to maintain the goal feedback shape and size. The gains could then be adjusted over the course of training to introduce a progression of exercise difficulty as appropriate to a given individual's performance—as the participant masters exercise form at one gain setting, the exercise could be progressed to further challenge the participant to improve more. The initial individual gains could be determined from a statistical distribution of participant pre-test performances, where the location of the participant's performance relative to the distribution determines the feedback gains used to generate the feedback display. From the same distribution it would also be possible to determine acceptable ranges for the biomechanical variables. For example, it may be counterproductive to provide feedback on trunk lean values that are within ±1.0° of 0.0° (the trunk is almost negligible). Lastly, additional exercises could be programmed that target complementary biomechanical variables, such as the single-leg Romanian deadlift. The exercise is performed on a single leg, requiring that the person essentially bends over (at the waist) and touches the ground with their fingers. This exercise may lead to greater trunk control, more stable hip joint dynamics, and improved balance beyond the effects of the unweighted squat.

The current interactive, real-time biofeedback system effectively engages implicit motor learning mechanisms and promotes an external focus of attention. The heat map results revealed a positive change in participants' squatting performance from the pre- to posttest period. It is envisioned that the system of the present disclosure may provide a more efficient method for reducing ACL injury risk in high-risk athlete populations.

Although the invention has been described in detail with reference to certain preferred embodiments, variations and modifications exist within the spirit and scope of the invention as described and defined in the following claims.

The invention claimed is:

1. An augmented neuromuscular training system for providing real-time feedback to a participant performing exercises, the training system comprising:
- a biomechanical acquisition system comprising a sensor for tracking movement of the participant and generating a biomechanical data structure based on data obtained from the sensor including position data indicative of the movement of the participant;
- a motion analysis and feedback system in communication with the biomechanical acquisition system, the motion analysis and feedback system including a controller configured to receive the biomechanical data structure from the biomechanical acquisition system, the controller including an exercise processing sequence for generating a stimulus data structure in response to the biomechanical data structure, wherein the stimulus data structure includes a plurality of biomechanical variables;
- a user interface in communication with the motion analysis and feedback system and including a display visible to the participant, the display presenting a goal reference and a graphical stimulus defined by a plurality of stimulus coordinate points and that is a closed geometric shape in an initial configuration; and
- wherein the plurality of stimulus coordinate points are defined by the stimulus data structure and positions of the plurality of stimulus coordinate points are configured to vary relative to the goal reference in response to the plurality of biomechanical variables.

2. The training system of claim 1, wherein:
- the plurality of biomechanical variables are identified as movement deficits; and
- the graphical stimulus is defined by at least six stimulus coordinate points, and the closed geometric shape is a rectangle in the initial configuration.

3. The training system of claim 2, wherein the plurality of biomechanical variables include trunk lean, knee-to-hip moment ratio (KHMr), knee abduction moment (KAM), and vertical ground reaction force ratio (vGRF).

4. The training system of claim 2, wherein a size and a shape of the graphical stimulus varies in response to the plurality of biomechanical variables.

5. The training system of claim 2, wherein the user interface includes a headset configured to be worn by the participant and supporting the display, the headset including a wireless receiver for communication with the motion analysis and feedback system.

6. The training system of claim 5, wherein the headset further includes a speaker to transmit audible instructions from the motion analysis and feedback system to the participant.

7. The training system of claim 2, wherein the motion analysis and feedback system further includes an operator interface in communication with the controller, the operator interface including an input for adjusting gain for at least one of the plurality of biomechanical variables.

8. The training system of claim 1, wherein the biomechanical acquisition system includes a plurality of markers configured to be worn by the participant, and further comprises an image acquisition device comprising the sensor and configured to track relative positions of the plurality of markers, and wherein the controller is in communication with the image acquisition device for generating the biomechanical data structure.

9. The training system of claim 1, wherein the controller includes a plurality of different exercise processing sequences for generating respective stimulus data structures in response to different exercises performed by the participant.

10. The training system of claim 9, wherein the motion analysis and feedback system further includes an operator interface in communication with the controller, the operator interface including the display including the graphical stimulus and an operator input for selecting one of the different exercises.

11. The training system of claim 1, wherein the biomechanical acquisition system includes a plurality of markers that are virtual markers.

12. The training system of claim 11, wherein the biomechanical acquisition system further comprises an image acquisition device comprising the sensor and configured to track relative positions of the plurality of markers, and wherein the controller is in communication with the image acquisition device for generating the biomechanical data structure.

13. A motion analysis and feedback system in communication with a biomechanical acquisition system, the motion analysis and feedback system comprising:
- a controller configured to receive a biomechanical data structure including sensor data from a biomechanical acquisition system, the controller including an exercise processing sequence configured to convert the sensor data in the biomechanical data structure to a stimulus data structure, and for defining a plurality of stimulus coordinate points based on the stimulus data structure, wherein the stimulus data structure includes a plurality of biomechanical variables; and
- a user interface in communication with the controller, the user interface including a display visible to the participant, the display presenting a goal reference and a graphical stimulus defined by a plurality of stimulus coordinate points and that is a closed geometric shape in an initial configuration, wherein positions of the plurality of stimulus coordinate points are configured to vary relative to the goal reference in response to the plurality of biomechanical variables.

14. The motion analysis and feedback system of claim 13, wherein:
- the plurality of biomechanical variables are identified as anterior cruciate ligament (ACL) risk factors; and
- the graphical stimulus is defined by at least six stimulus coordinate points, and the closed geometric shape is a rectangle in the initial configuration.

15. The motion analysis and feedback system of claim 14, wherein the plurality of biomechanical variables include trunk lean, knee-to-hip moment ratio (KHMr), knee abduction moment (KAM), and vertical ground reaction force ration (vGRF).

16. The motion analysis and feedback system of claim 14, wherein a size and a shape of the graphical stimulus varies in response to the plurality of biomechanical variables.

17. The motion analysis and feedback system of claim 14, wherein the user interface includes a headset configured to be worn by the participant and supporting the display, the headset including a wireless receiver for communication with the motion analysis and feedback system.

18. The motion analysis and feedback system of claim 17, wherein the headset further includes a speaker to transmit audible instructions from the motion analysis and feedback system to the participant.

19. The motion analysis and feedback system of claim 14, wherein the motion analysis and feedback system further includes an operator interface in communication with the controller, the operator interface including an operator input for adjusting gain for at least one of the plurality of biomechanical variables.

20. The motion analysis and feedback system of claim 13, wherein the controller includes a plurality of different exercise processing sequences for generating respective stimulus data structures in response to different exercises performed by the participant.

21. The motion analysis and feedback system of claim 20, wherein the motion analysis and feedback system further includes an operator interface in communication with the controller, the operator interface including the display including the graphical stimulus and an operator input for selecting one of the different exercises.

22. A user interface for use with a motion analysis and feedback system, the user interface comprising:
   a display visible to a participant, the display presenting a goal reference and a graphical stimulus having a boundary that is defined by at least six stimulus coordinate points;
   a stimulus data structure including a plurality of biomechanical variables identified as anterior cruciate ligament (ACL) risk factors;
   wherein the graphical stimulus is a rectangle in an initial configuration; and
   wherein relative positions of the at least six stimulus coordinate points are configured to vary relative to the goal reference in response to the plurality of biomechanical variables and sensor data obtained from a biomechanical acquisition system that indicates a position of the participant, such that a size and a shape of the graphical stimulus varies in response to the plurality of biomechanical variables and the sensor data.

23. The user interface of claim 22, wherein the plurality of biomechanical variables include trunk lean, knee-to-hip moment ratio (KHMr), knee abduction moment (KAM), and vertical ground reaction force ration (vGRF).

24. The user interface of claim 22, wherein the user interface includes a headset configured to be worn by the participant and supporting the display, the headset including a wireless receiver for communication with a motion analysis and feedback system.

* * * * *